United States Patent
Lande et al.

(10) Patent No.: US 11,951,154 B2
(45) Date of Patent: *Apr. 9, 2024

(54) COMPOSITIONS AND METHODS FOR CELL DELIVERY

(71) Applicant: Flagship Pioneering Innovations V, Inc., Cambridge, MA (US)

(72) Inventors: Laura Gabriela Lande, Chestnut Hill, MA (US); David Arthur Berry, Newton, MA (US)

(73) Assignee: FLAGSHIP PIONEERING INNOVATIONS V, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/835,659

(22) Filed: Jun. 8, 2022

(65) Prior Publication Data

US 2023/0024896 A1 Jan. 26, 2023

Related U.S. Application Data

(63) Continuation of application No. 16/346,684, filed as application No. PCT/US2017/059610 on Nov. 1, 2017, now Pat. No. 11,382,950.

(60) Provisional application No. 62/416,378, filed on Nov. 2, 2016, provisional application No. 62/416,372, filed on Nov. 2, 2016, provisional application No. 62/416,367, filed on Nov. 2, 2016.

(51) Int. Cl.
| | |
|---|---|
| *A61K 38/00* | (2006.01) |
| *A61K 38/16* | (2006.01) |
| *A61K 47/64* | (2017.01) |
| *A61K 47/65* | (2017.01) |
| *C07K 7/08* | (2006.01) |
| *C07K 9/00* | (2006.01) |

(52) U.S. Cl.
CPC ............ *A61K 38/16* (2013.01); *A61K 47/64* (2017.08); *A61K 47/65* (2017.08); *C07K 7/08* (2013.01); *C07K 9/00* (2013.01)

(58) Field of Classification Search
CPC ........ A61K 38/16; A61K 47/64; A61K 47/65; C07K 7/08; C07K 9/00
See application file for complete search history.

(56) References Cited

U.S. PATENT DOCUMENTS

| | | | |
|---|---|---|---|
| 5,955,343 | A | 9/1999 | Holmes et al. |
| 2003/0073630 | A1 | 4/2003 | Bridon et al. |
| 2016/0175456 | A1 | 6/2016 | Chen et al. |

FOREIGN PATENT DOCUMENTS

| | | |
|---|---|---|
| CA | 2800650 A1 | 12/2011 |
| WO | 2015/113922 A1 | 8/2015 |
| WO | 2018/085460 A2 | 5/2018 |

OTHER PUBLICATIONS

International Search Report and Written Opinion of application No. PCTUS2017059610 dated Apr. 19, 2018
Rafie et al., "Thio-Linked UDP-Peptide Conjugates as O-GlcNAc Transderase Inhibitors," Bioconjugate Chemistry (2018) vol. 29, No. 6, pp. 1834-1840.
Takahashi et al., "Construction of Peptides with Nucleobase Amino Acids: Design and Synthesis of the Nucleobase-Conjugated Peptides Derived from HIV-1 Rev and their Binding Properties to HIV-1 RRE RNA," Bioorganic & Medicinal Chemistry (2001), vol. 9, Issue 4, pp. 991-1000.

*Primary Examiner* — Aradhana Sasan
*Assistant Examiner* — Mercy H Sabila
(74) *Attorney, Agent, or Firm* — K&L Gates LLP

(57) ABSTRACT

The present disclosure described herein provides compositions with a membrane-penetrating properties and methods for allowing translocation across a membrane without disruption.

19 Claims, 15 Drawing Sheets

Specification includes a Sequence Listing.

COMPOSITIONS AND METHODS FOR CELL DELIVERY

CROSS-REFERENCE TO RELATED APPLICATIONS

The present application is a continuation of U.S. patent application Ser. No. 16/346,684, filed May 1, 2019, which is a U.S. national phase application and claims the benefit of priority under 35 U.S.C. § 371 of International Patent Application No. PCT/US2017/059610, filed Nov. 1, 2017, which claims priority to and benefit from U.S. provisional applications U.S. Ser. No. 62/416,367 (filed Nov. 2, 2016), U.S. Ser. No. 62/416,372 (filed Nov. 2, 2016), and U.S. Ser. No. 62/416,378 (filed Nov. 2, 2016), the contents of each of which are herein incorporated by reference.

SEQUENCE LISTING

The instant application contains a Sequence Listing which has been submitted electronically in ASCII format and is hereby incorporated by reference in its entirety. Said ASCII copy, created on Sep. 21, 2022, is named 02057-700620 SL.txt and is 9,562 bytes in size.

BACKGROUND

Plasma and nuclear cellular membranes present major challenges for efficient delivery of drug therapies and modulating gene expression, especially for biologics such as peptides, proteins, and nucleic acids.

SUMMARY

The present disclosure provides certain therapeutic compositions and methods useful to modulate cell or tissue function, e.g., to treat a subject in need thereof. Compositions and methods described herein allow delivery of an effector (such as, e.g. a therapeutic agent) to a target location within a cell, e.g., allow delivery of a therapeutic agent across a cellular membrane (e.g., across a plasma membrane, a nuclear membrane, or another organellar membrane).

In some aspects, the present disclosure provides one or more pharmaceutical compositions comprising at least one polypeptide with each comprising a sequence of $ABX^nC$ and at least one heterologous moiety (e.g. cargo). In some embodiments, A is a hydrophobic amino acid; B and C may be the same or different, and are independently selected from arginine (Arg, R), asparagine (Asn, N), glutamine (Gln, Q), lysine (Lys, K), and analogs thereof; X is each independently a hydrophobic amino acid; and n is an integer from 1 to 4;

Compositions as described in various embodiments of any above aspects (Ala, A), glycine (Gly, G), valine (Val, V), isoleucine (Ile, I), leucine (Leu, L), methionine (Met, M), phenylalanine (Phe, F), tyrosine (Tyr, Y), tryptophan (Trp, W), and analogs thereof. In some embodiments, a hydrophobic amino acid does not include glycine. In some embodiments, B is selected from arginine or glutamine. In some embodiments, C is arginine. In some embodiments, n is 2.

In some embodiments, one or more polypeptides have sizes in a range of about 5 to about 50 amino acid units in length.

In some embodiments, a provided composition comprises two or more polypeptides that are linked to one another. In some embodiments, the polypeptides are linked to one another, e.g., amino acids on one polypeptide are linked with one or more amino acids or a carboxy or amino terminal on another polypeptide (e.g., a branched polypeptide), or through new peptide bonds, (e.g. a linear polypeptide). In some embodiments, the polypeptides are linked by a linker as described herein.

In some embodiments, the heterologous moiety is selected from the group consisting of a small molecule (e.g., a drug), a peptide (e.g., ligand), a peptide nucleic acid (PNA), and a nucleic acid (e.g., siRNA, DNA, mRNA, tRNA, etc.).

In some embodiments, the heterologous moiety possesses at least one effector activity selected from the group consisting of modulates a biological activity, binds a regulatory protein, modulates enzymatic activity, modulates substrate binding, modulates receptor activation, modulates protein stability/degradation, and modulates transcript stability/degradation.

In some embodiments, the heterologous moiety possesses at least one targeted function selected from the group consisting of modulates a function, modulates a molecule (e.g., enzyme, protein, nucleic acid), and is localized to a specific location.

In some embodiments, the heterologous moiety is or comprises a tag or a label. In some embodiments, a tag or a label may be cleaved from the polypeptide.

In some embodiments, the heterologous moiety is selected from the group consisting of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR system or component thereof, DNA, RNA, artificial nucleic acids, a nanoparticle, an oligonucleotide aptamer, a peptide aptamer, and an agent with poor pharmacokinetics or pharmacodynamics (PK/PD).

In some embodiments, the heterologous moiety is cleavable.

In some embodiments, the heterologous moiety is linked, e.g., via a linker or directly, to the polypeptide on an amino terminus, a carboxy terminus, both termini, or one or more amino acids of the polypeptide. In some embodiments, a provided composition further comprises a linker, e.g., between polypeptides or between the polypeptide and the heterologous moiety. In some embodiments, a linker may be a chemical bond, e.g., one or more covalent bonds or non-covalent bonds. In some embodiments, a linker is a peptide linker (e.g., a nonABX"C polypeptide). In some embodiments, a peptide linker may be between about 2 to about 30 amino acids, or longer. A linker may include, e.g., flexible, rigid, or cleavable linkers, as described herein.

In some embodiments, two or more heterologous moieties may be linked (e.g., via a linker or directly), to two or more polypeptides on amino termini, on carboxy termini, all termini, a combination of some carboxy and some amino termini of the polypeptides, one or more amino acids of the polypeptide, or any combination thereof.

In some embodiments, a provided polypeptide as described herein has a capacity to form linkages, e.g., after administration to a subject, to other polypeptides, to a heterologous moiety as described herein, e.g., an effector molecule, e.g., a nucleic acid, protein, peptide or other molecule, or other agent, e.g., intracellular molecules, such as through covalent bonds or non-covalent bonds.

In some aspects, the present disclosure provides methods of delivering a therapeutic comprising administering a provided composition, which composition is or comprises at least one polypeptide, wherein a sequence of a given polypeptide comprises $ABX_nC$, wherein A is a hydrophobic amino acid; B and C may be the same or different, and are each independently selected from arginine (Arg, R), asparagine (Asp, N), glutamine (Glu, Q), lysine (Lys, K), and analogs thereof; X is each independently a hydrophobic amino acid; and n is an integer from 1 to 4, or one or more provided compositions as described herein to a subject, wherein the heterologous moiety is a therapeutic, and wherein a provided composition increases intracellular delivery of a therapeutic as compared to a therapeutic alone.

In some embodiments, for example, a provided composition may increase intracellular delivery of a therapeutic at least 5%, 10%, 15%, 20%, 30%, 40%, 50%, 60%, 75%, 80%, 90% or more, as compared to the therapeutic alone.

Methods as described in various embodiments of any above aspects may be utilized in any other aspects delineated herein.

In some embodiments, a composition as provided herein is targeted to one or more specific tissues and/or cells. In some embodiments, for example, a composition is targeted to an epithelial, connective, muscular, or nervous tissue or cells, or combinations thereof. In some embodiments, for example, a composition may be targeted to a cell or tissue of a particular organ system, e.g., the cardiovascular system (heart, vasculature); digestive system (esophagus, stomach, liver, gallbladder, pancreas, intestines, colon, rectum and anus); endocrine system (hypothalamus, pituitary gland, pineal body or pineal gland, thyroid, parathyroid, adrenal glands); excretory system (kidneys, ureters, bladder); lymphatic system (lymph, lymph nodes, lymph vessels, tonsils, adenoids, thymus, spleen);

integumentary system (skin, hair, nails); muscular system (e.g., skeletal muscle); nervous system (brain, spinal cord, nerves); reproductive system (ovaries, uterus, mammary glands, testes, vas deferens, seminal vesicles, prostate); respiratory system (pharynx, larynx, trachea, bronchi, lungs, diaphragm); skeletal system (bone, cartilage), and combinations thereof. In some embodiments, a composition crosses a blood-brain-barrier, a placental membrane, or a blood-testis barrier.

In some embodiments, a composition as provided herein may be administered systemically. In some embodiments, administration is non-parenteral and a therapeutic is a parenteral therapeutic.

In some embodiments, a composition as provided herein (which composition comprises a therapeutic) has improved PK/PD, e.g., increased pharmacokinetics or pharmacodynamics, such as improved targeting, absorption, or transport (e.g., at least about 5%, 10%, 15%, 20%, 30%, 40%, 50%, 60%, 75%, 80%, 90% improved or more) as compared to a therapeutic alone. In some embodiments, a provided composition has reduced undesirable effects, such as reduced diffusion to non-target location, off-target activity, or toxic metabolism, as compared to a therapeutic alone (e.g., at least about 5%, 10%, 15%, 20%, 30%, 40%, 50%, 60%, 75%, 80%, 90% or more reduced, as compared to the therapeutic alone). In some embodiments, a composition increases efficacy and/or decreases toxicity of a therapeutic (e.g., at least about 5%, 10%, 15%, 20%, 30%, 40%, 50%, 60%, 75%, 80%, 90% or more) as compared to a therapeutic alone.

In some aspects, the present disclosure provides methods of intracellular delivery of a therapeutic comprising contacting a cell with at least one polypeptide comprising a sequence of $ABX_nC$, wherein A is a hydrophobic amino acid; B and C may be the same or different, and are each independently selected from arginine (Arg, R), asparagine (Asn, N), glutamine (Glu, Q), lysine (Lys, K), and analogs thereof; X is each independently a hydrophobic amino acid; and n is an integer from 1 to 4, or a composition as described herein, wherein the heterologous moiety is a therapeutic, and wherein a composition increases intracellular delivery of a therapeutic as compared to a therapeutic alone.

Methods as described in various embodiments of any above aspects may be utilized in any other aspects delineated herein.

In some embodiments, a composition (comprising a therapeutic) as provided herein has differential PK/PD as compared to a therapeutic alone. For example, a provided composition (comprising a therapeutic) may exhibit increased or decreased absorption or distribution, metabolism or excretion (e.g., at least about 5%, 10%, 15%, 20%, 30%, 40%, 50%, 60%, 75%, 80%, 90% or more increased or decreased), as compared to a therapeutic alone.

In some embodiments, a composition as provided herein is administered at a dose sufficient to increase intracellular delivery of a therapeutic without significantly increasing endocytosis, e.g., less than at least about 50%, 40%, 20%, 15%, 10%, 5%, 4%, 3%, 2%, 1%, or any percentage therebetween. In some embodiments, a provided composition is administered at a dose sufficient to increase intracellular delivery of the therapeutic without significantly increasing calcium influx, e.g., less than at least about 50%, 40%, 20%, 15%, 10%, 5%, 4%, 3%, 2%, 1%, or any percentage therebetween. In some embodiments, a provided composition is administered at a dose sufficient to increase intracellular delivery of the therapeutic without significantly increasing endosomal activity, e.g., less than at least about 50%, 40%, 20%, 15%, 10%, 5%, 4%, 3%, 2%, 1%, or any percentage therebetween.

In some aspects, the present disclosure provides methods of modulating transcription of a gene in a cell comprising contacting a cell with at least one polypeptide comprising a sequence of $ABX_nC$, wherein A is a hydrophobic amino acid; B and C may be the same or different, and are each independently selected from arginine (Arg, R), asparagine (Asn, N), glutamine (Gln, Q), lysine (Lys, K), and analogs thereof; X is each independently a hydrophobic amino acid; and n is an integer from 1 to 4, or a composition described herein, wherein a provided composition targets a gene and modulates its transcription.

Methods as described in various embodiments of any above aspects may be utilized in any other aspects delineated herein.

In some embodiments, a composition as provided herein is administered in an amount and for a time sufficient to effect intracellular delivery of a therapeutic with decreased off target transcriptional activity compared to a heterologous moiety alone, e.g., without significantly altering off-target transcriptional activity.

In some aspects the present disclosure provides methods of modulating a membrane protein, e.g., such as an ion channel, a cell surface receptor and a synaptic receptor, on a cell comprising contacting the cell with at least one polypeptide with each comprising a sequence of $ABX_nC$, wherein A is a hydrophobic amino acid; B and C may be the same or different, and are each independently selected from arginine (Arg, R), asparagine (Asn, N), glutamine (Gln, Q), lysine (Lys, K), and analogs thereof; X is each independently a hydrophobic amino acid; and n is an integer from 1 to 4, or a composition described herein, wherein a provided composition targets the cell and modulates a membrane protein.

In some aspects, the present disclosure provides methods of inducing cell death comprising contacting a cell with at least one polypeptide with each comprising a sequence of $ABX^nC$, wherein A is a hydrophobic amino acid; B and C may be the same or different, and are each independently selected from arginine (Arg, R), asparagine (Asn, N), glutamine (Gln, Q), lysine (Lys, K), and analogs thereof; X is each independently a hydrophobic amino acid; and n is an integer from 1 to 4, or a composition as described herein, wherein a provided composition targets a cell and induces apoptosis.

Methods described in various embodiments of any above aspects may be utilized in any other aspects delineated herein.

In some embodiments, a composition as provided herein targets a cell harboring a viral DNA sequence or a mutation in a gene.

In some embodiments, the cell is virally infected.

In some embodiments, the cell harbors a genetic mutation.

In some embodiments, a composition targets a cell in early stages of necrosis, e.g., binding a necrotic cell marker.

In some aspects, the present disclosure provides methods of increasing bioavailability of a therapeutic comprising administering at least one polypeptide wherein each polypeptide comprises a sequence of $ABX^nC$, wherein A is a hydrophobic amino acid; B and C may be the same or different, and are each independently selected from arginine (R, Arg), asparagine (Asn, N), glutamine (Gln, Q), lysine, and analogs thereof; X is each independently a hydrophobic amino acid; and n is an integer from 1 to 4, or a composition described herein, wherein the therapeutic is a heterologous moiety.

Methods as described in various embodiments of any above aspects may be utilized in any other aspects delineated herein.

In some embodiments, a provided composition (comprising a therapeutic) improves (e.g., by at least 5%, 10%, 15%, 20%, 30%, 40%, 50%, 60%, 75%, 80%, 90% or more) at least one PK/PD parameter, such as improved targeting, absorption, or transport, as compared to a therapeutic alone. In some embodiments, a composition (comprising a therapeutic) reduces (e.g., by at least 5%, 10%, 15%, 20%, 30%, 40%, 50%, 60%, 75%, 80%, 90% or more) at least one unwanted parameter, such as reduced diffusion to non-target location, off-target activity, or toxic metabolism, as compared to a therapeutic alone. In some embodiments, a composition (comprising a therapeutic) increases efficacy and/or decreases toxicity of a therapeutic as compared to a therapeutic alone.

In some aspects, the present disclosure provides methods of treating an acute or chronic infection comprising administering at least one polypeptide with each polypeptide comprising a sequence of $ABX^nC$, wherein A is a hydrophobic amino acid; B and C may be the same or different, and are each independently selected from arginine (Arg, R), asparagine (Asn, N), glutamine (Gln, G), lysine (Lys, K), and analogs thereof; X is each independently a hydrophobic amino acid; and n is an integer from 1 to 4, or a composition described herein.

Methods as described in various embodiments of any above aspects may be utilized in any other aspects delineated herein.

In some embodiments, a composition of the present disclosure targets an infected cell harboring a pathogen. In some embodiments, the infection is caused by a pathogen selected from the group consisting of a virus, bacteria, parasite, and a prion. In some embodiments, a composition induces cell death in the infected cell, e.g., the heterologous moiety is an antibacterial, an antiviral, or an antiparasitic therapeutic.

In some aspects, the present disclosure provides methods of treating a cancer comprising administering at least one polypeptide with each comprising a sequence of $ABX^nC$, wherein A is a hydrophobic amino acid; B and C may be the same or different, and are each independently selected from arginine (Arg, R), asparagine (Asn, N), glutamine (Gln, Q), lysine (Lys, K), and analogs thereof; X is each independently a hydrophobic amino acid; and n is an integer from 1 to 4, or a composition described herein.

Methods as described in various embodiments of any above aspects may be utilized in any other aspects delineated herein.

In some embodiments, the heterologous moiety is a therapeutic that modulates gene expression of one or more genes.

In some embodiments, a composition targets a cancer cell harboring a mutation in a gene. In some embodiments, a composition induces cell death in the cancer cell, e.g., the heterologous moiety is a chemotherapeutic agent.

In some aspects, the present disclosure provides methods of treating a neurological disease or disorder comprising administering at least one polypeptide with each comprising a sequence of $ABX^nC$, wherein A is a hydrophobic amino acid; B and C may be the same or different, and are each independently selected from arginine (Arg, R), asparagine (Asn, N), glutamine (Gln, Q), lysine (Lys, K), and analogs thereof; X is each independently a hydrophobic amino acid; and n is an integer from 1 to 4, or a composition described herein.

Methods as described in various embodiments of any above aspects may be utilized in any other aspects delineated herein.

In some embodiments, a composition modulates neuroreceptor activity or activation of a neurotransmitter, neuropeptide, or neuroreceptor.

In some aspects, the present disclosure provides methods of treating a disease/disorder/condition in a subject comprising administering at least one polypeptide with each comprising a sequence of $ABX^nC$, wherein A is a hydrophobic amino acid; B and C may be the same or different, and are each independently selected from arginine (Arg, R), asparagine (Asn, N), glutamine (Gln, Q), lysine (Lys, K), and analogs thereof; X is each independently a hydrophobic amino acid; and n is an integer from 1 to 4, or a composition described herein, wherein a composition modulates transcription to treat the disease/disorder/condition.

Methods as described in various embodiments of any above aspects may be utilized in any other aspects delineated herein.

In some embodiments, the disease/disorder/condition is a genetic disease.

In some aspects, the present disclosure provides methods of inducing immune tolerance comprising providing at least one polypeptide with each comprising a sequence of $ABX^nC$, wherein A is a hydrophobic amino acid; B and C may be the same or different, and are each independently selected from arginine (Arg, R), asparagine (Asn, N), glutamine (Gln, Q), lysine (Lys, K), and analogs thereof; X is each independently a hydrophobic amino acid; and n is an integer from 1 to 4, or a composition described herein, e.g., the heterologous moiety is an antigen.

In some aspects, the present disclosure provides methods of delivering a therapeutic comprising administering a composition to a subject, a composition comprising a polypeptide comprising at least one sequence of $ABX^nC$, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo, wherein the heterologous moiety is the therapeutic, and wherein a composition (comprising a therapeutic) increases intracellular delivery of a therapeutic as compared to a therapeutic alone.

In some embodiments, a hydrophobic amino acid is selected from alanine (Ala, A), glycine (Gly, G), valine (Val, V), isoleucine (Ile, I), leucine (Leu, L), methionine (Met, M), phenylalanine (Phe, F), tyrosine (Tyr, Y), tryptophan (Trp, W), and analogs thereof. In some embodiments, a hydrophobic amino acid does not include glycine. In some embodiments, B is selected from arginine or glutamine. In some embodiments, C is arginine. In some embodiments, n is 2.

In some embodiments, a nucleic acid side chain is independently selected from the group consisting of a purine side chain, a pyrimidine side chain, and a nucleic acid analog side chain. In some embodiments, the nucleic acid side chain hybridizes to the heterologous moiety, wherein the heterologous moiety comprises a nucleic acid side chain, e.g., a PNA, or nucleic acid, and wherein a nucleic acid may be a synthetic nucleic acid.

In some embodiments, the polypeptides comprise at least two $ABX^nC$ sequences. In some embodiments, the polypeptides have sizes in the range of about 5 to about 50 amino acid units in length.

In some embodiments, the heterologous moiety is selected from the group consisting of a small molecule (e.g., a drug), a peptide (e.g., ligand), a peptide nucleic acid (PNA), and a nucleic acid (e.g., siRNA, DNA, mRNA, tRNA, etc.).

In some embodiments, the heterologous moiety possesses at least one effector activity selected from the group consisting of modulates a biological activity, binds a regulatory protein, modulates enzymatic activity, modulates substrate binding, modulates receptor activation, modulates protein stability/degradation, and modulates transcript stability/degradation.

In some embodiments, the heterologous moiety possesses at least one targeted function selected from the group consisting of modulates a function, modulates a molecule (e.g., enzyme, protein or nucleic acid), and is localized to a specific location.

In some embodiments, the heterologous moiety is or comprises a tag or label, e.g., cleavable.

In some embodiments, the heterologous moiety is selected from the group consisting of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR system or component thereof, DNA, RNA, artificial nucleic acids, a nanoparticle, an oligonucleotide aptamer, a peptide aptamer, and an agent with poor pharmacokinetics or pharmacodynamics (PK/PD).

In some embodiments, the heterologous moiety is cleavable.

In some embodiments, the heterologous moiety is linked, e.g., via a linker or directly, to the polypeptide on an amino terminus, a carboxy terminus, both termini, or one or more amino acids of the polypeptide. In some embodiments, two or more heterologous moieties are linked. The linker may be a chemical bond, e.g., one or more covalent bonds or non-covalent bonds. In some embodiments, the linker is a peptide linker (e.g., a non $ABX^nC$ polypeptide). Such a linker may be between 2-30 amino acids, or longer. The linker includes flexible, rigid or cleavable linkers described herein.

Methods as described in various embodiments of any above aspects may be utilized in any other aspects delineated herein.

In some embodiments, provided compositions are targeted to one or more specific tissues and/or cells. In some embodiments, for example, a composition may be targeted to an epithelial, connective, muscular, or nervous tissue or cells, or combinations thereof. In some embodiments, for example, a composition may be targeted to a cell or tissue of a particular organ system, e.g., the cardiovascular system (heart, vasculature); digestive system (esophagus, stomach, liver, gallbladder, pancreas, intestines, colon, rectum and anus); endocrine system (hypothalamus, pituitary gland, pineal body or pineal gland, thyroid, parathyroid, adrenal glands); excretory system (kidneys, ureters, bladder); lymphatic system (lymph, lymph nodes, lymph vessels, tonsils, adenoids, thymus, spleen); integumentary system (skin, hair, nails); muscular system (e.g., skeletal muscle); nervous system (brain, spinal cord, nerves); reproductive system (ovaries, uterus, mammary glands, testes, vas deferens, seminal vesicles, prostate); respiratory system (pharynx, larynx, trachea, bronchi, lungs, diaphragm); skeletal system (bone, cartilage), and combinations thereof. In some embodiments, a provided composition crosses a blood-brain-barrier, a placental membrane, or a blood-testis barrier.

In some embodiments, a composition is administered systemically. In some embodiments, administration is non-parenteral and a therapeutic is a parenteral therapeutic.

In some embodiments, provided compositions (comprising a therapeutic) have improved PK/PD, e.g., increased pharmacokinetics or pharmacodynamics, such as improved targeting, absorption, or transport (e.g., at least 5%, 10%, 15%, 20%, 30%, 40%, 50%, 60%, 75%, 80%, 90% improved or more) as compared to a therapeutic alone. In some embodiments, provided compositions (comprising a therapeutic) have reduced undesirable effects, such as reduced diffusion to non-target location, off-target activity, or toxic metabolism, as compared to a therapeutic alone (e.g., at least 5%, 10%, 15%, 20%, 30%, 40%, 50%, 60%, 75%, 80%, 90% or more reduced, as compared to the therapeutic alone). In some embodiments, compositions (comprising a therapeutic) increase efficacy and/or decreases toxicity of a therapeutic (e.g., at least 5%, 10%, 15%, 20%, 30%, 40%, 50%, 60%, 75%, 80%, 90% or more) as compared to a therapeutic alone.

In some aspects, the present disclosure provides methods of intracellular delivery of a therapeutic comprising contacting a cell with a composition comprising a polypeptide comprising at least one sequence of $ABX^nC$, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo, wherein the heterologous moiety is a therapeutic, and wherein a composition (comprising a therapeutic) increases intracellular delivery of a therapeutic as compared to a therapeutic alone.

Methods as described in various embodiments of any above aspects may be utilized in any other aspects delineated herein.

In some embodiments, a composition (comprising a therapeutic) has differential PK/PD as compared to the therapeutic alone. In some embodiments, f example, a composition (comprising a therapeutic) exhibits increased or decreased absorption or distribution, metabolism or excretion (e.g., at least 5% 10% 15% 20% 30% 40% 50% 60% 75% 80% 90% or more increased or decreased) as, compared to a therapeutic alone.

In some embodiments, a composition may be administered at a dose sufficient to increase intracellular delivery of the therapeutic without significantly increasing endocytosis, e.g., less than about 50%, 40%, 20%, 15%, 10%, 5%, 4%, 3%, 2%, 1%, or any percentage therebetween. In some embodiments, a composition (comprising a therapeutic) may be administered at a dose sufficient to increase intracellular delivery of a therapeutic without significantly increasing calcium influx, e.g., less than about 50%, 40%, 20%, 15%, 10%, 5%, 4%, 3%, 2%, 1%, or any percentage therebetween. In some embodiments, composition (comprising a therapeutic) may be administered at a dose sufficient to increase intracellular delivery of a therapeutic without significantly increasing endosomal activity, e.g., less than about 50%, 40%, 20%, 15%, 10%, 5%, 4%, 3%, 2%, 1%, or any percentage therebetween.

In some aspects, the present disclosure provides methods of modulating transcription of a gene in a cell comprising contacting a cell with a composition comprising a polypeptide, which polypeptide comprises at least one sequence of $ABX^nC$, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., a targeting cargo, wherein a provided composition targets a gene and modulates its transcription.

Methods as described in various embodiments of any above aspects may be utilized in any other aspects delineated herein.

In some embodiments, a composition (comprising a therapeutic) is administered in an amount and for a time sufficient to effect intracellular delivery of a therapeutic with decreased off target transcriptional activity compared to a heterologous moiety alone, e.g., without significantly altering off-target transcriptional activity.

In some aspects, the present disclosure provides methods of modulating gene expression comprising providing a composition comprising a polypeptide comprising at least one sequence of $ABX^nC$, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo, is or comprises an endogenous effector, is or comprises an exogenous effector, is or comprises an agonist or is or comprises an antagonist thereof.

Methods as described in various embodiments of any above aspects may be utilized in any other aspects delineated herein.

In some aspects, the present disclosure provides methods of modulating a membrane protein, e.g., such as an ion channel, a cell surface receptor and a synaptic receptor, on a cell comprising contacting the cell with a composition comprising a polypeptide comprising at least one sequence of $ABX^nC$, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo, wherein a provided composition targets a cell and modulates a membrane protein.

Methods as described in various embodiments of any above aspects may be utilized in any other aspects delineated herein.

In some aspects, the present disclosure provides methods of inducing cell death comprising contacting a cell with a composition comprising a polypeptide comprising at least one sequence of $ABX^nC$, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo, e.g., the heterologous moiety is a nucleic acid that specifically binds a mutation sequence, wherein a composition targets a cell and may induce apoptosis.

Methods as described in various embodiments of any above aspects may be utilized in any other aspects delineated herein.

In some embodiments, a provided composition further comprises a heterologous moiety that induces apoptosis.

In some embodiments, a provided composition may target a cell harboring a viral DNA sequence or a mutation in a gene.

In some embodiments, a cell is virally infected.

In some embodiments, a cell harbors a genetic mutation.

In some embodiments, a composition targets a cell in the early stages of necrosis, e.g., binding necrotic cell marker.

In some aspects, the present disclosure provides methods of increasing bioavailability of a therapeutic comprising administering a composition comprising a polypeptide comprising at least one sequence of ABX"C, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo, wherein a therapeutic is the heterologous moiety.

Methods as described in various embodiments of any above aspects may be utilized in any other aspects delineated herein.

In some embodiments, a provided composition improves (e.g., by at least 5%, 10%, 15%, 20%, 30%, 40%, 50%, 60%, 75%, 80%, 90% or more) at least one PK/PD parameter, such as improved targeting, absorption, or transport, as compared to the therapeutic alone. In some embodiments, a composition reduces (e.g., by at least 5%, 10%, 15%, 20%, 30%, 40%, 50%, 60%, 75%, 80%, 90% or more) at least one unwanted parameter, such as reduced diffusion to non-target location, off-target activity, or toxic metabolism, as compared to the therapeutic alone. In some embodiments, a composition (comprising a therapeutic) increases efficacy and/or decreases toxicity of a therapeutic as compared to a therapeutic alone.

In some aspects, the present disclosure provides methods of treating an acute or chronic infection comprising administering a composition comprising a polypeptide comprising at least sequence of ABX"C, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo.

Methods as described in various embodiments of any above aspects may be utilized in any other aspects delineated herein.

In some embodiments, a composition targets an infected cell harboring a pathogen. In some embodiments, an infection is caused by a pathogen selected from the group consisting of a virus, bacteria, parasite, and a prion. In some embodiments, a provided composition may induce cell death in an infected cell, e.g., the heterologous moiety is, e.g. an antibacterial, an antiviral, or an antiparasitic therapeutic.

In some aspects, the present disclosure provides methods of treating a cancer comprising administering a composition comprising a polypeptide comprising at least one sequence of ABX"C, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to; and at least one heterologous moiety, e.g., cargo.

Methods as described in various embodiments of any above aspects may be utilized in any other aspects delineated herein.

In some embodiments, the heterologous moiety is a therapeutic that may modulate gene expression of one or more genes.

In some embodiments, a provided composition may target a cancer cell harboring a mutation in a gene. In some embodiments, a composition induces cell death in a cancer cell, e.g., the heterologous moiety is, e.g. a chemotherapeutic agent.

In some aspects, the present disclosure provides methods of treating a neurological disease or disorder comprising administering composition comprising a polypeptide comprising at least one sequence of ABX"C, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo.

Methods as described in various embodiments of any above aspects may be utilized in any other aspects delineated herein.

In some embodiments, a composition modulates neuroreceptor activity or activation of a, e.g. neurotransmitter, neuropeptide, or neuroreceptor.

In some aspects, the present disclosure provides methods of treating a disease/disorder/condition in a subject comprising administering a composition comprising a polypeptide comprising at least one sequence of ABX"C, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo, wherein a composition modulates transcription to treat the disease/disorder/condition.

Methods as described in various embodiments of any above aspects may be utilized in any other aspects delineated herein.

In some embodiments, the disease/disorder/condition is a genetic disease.

In some aspects, the present disclosure provides methods of inducing immune tolerance comprising providing a composition comprising a polypeptide comprising at least one sequence of ABX"C, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo, e.g., the heterologous moiety is an antigen.

Methods as described in various embodiments of any above aspects may be utilized in any other aspects delineated herein.

In some aspects, the present disclosure includes a pharmaceutical composition comprising a polypeptide comprising at least one sequence of ABX"C, wherein A is selected from a hydrophobic amino acid or an amide containing backbone, e.g., aminoethyl-glycine, with a nucleic acid side chain; B and C may be the same or different, and are independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4; and at least one heterologous moiety, e.g., cargo.

Composition as described in various embodiments of any above aspects may be utilized in any other aspects delineated herein.

In some embodiments, the hydrophobic amino acid is selected from In some embodiments, a hydrophobic amino acid is selected from alanine (Ala, A), glycine (Gly, G), valine (Val, V), isoleucine (Ile, I), leucine (Leu, L), methionine (Met, M), phenylalanine (Phe, F), tyrosine (Tyr, Y), tryptophan (Trp, W), and analogs thereof. In some embodiments, a hydrophobic amino acid does not include glycine. In some embodiments, B is selected from arginine or glutamine. In some embodiments, C is arginine. In some embodiments, n is 2.

In some embodiments, the polypeptide comprises at least two ABX"C sequences. In some embodiments, the polypeptides have sizes in the range of about 5 to about 50 amino acid units in length.

In some embodiments, a nucleic acid side chain is independently selected from the group consisting of a purine side chain, a pyrimidine side chain, and a nucleic acid analog side chain. In some embodiments, the nucleic acid side chain hybridizes to the heterologous moiety, wherein the heterologous moiety comprises a nucleic acid side chain, e.g., a PNA, or nucleic acid.

In some embodiments, the heterologous moiety is selected from the group consisting of a small molecule (e.g., a drug), a peptide (e.g., ligand), a peptide nucleic acid (PNA), and a nucleic acid (e.g., siRNA, DNA, modified RNA, RNA).

In some embodiments, the heterologous moiety possesses at least one effector activity selected from the group consisting of modulates a biological activity, binds a regulatory protein, modulates enzymatic activity, modulates substrate binding, modulates receptor activation, modulates protein stability/degradation, and modulates transcript stability/degradation.

In some embodiments, the heterologous moiety possesses at least one targeted function selected from the group consisting of modulates a function, modulates a molecule (e.g., enzyme, protein or nucleic acid), and is localized to a specific location.

In some embodiments, the heterologous moiety is or comprises a tag or label, e.g., cleavable.

In some embodiments, the heterologous moiety is selected from the group consisting of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR system or component thereof, DNA, RNA, artificial nucleic acids, a nanoparticle, an oligonucleotide aptamer, a peptide aptamer, and an agent with poor pharmacokinetics or pharmacodynamics (PK/PD).

In some embodiments, the heterologous moiety is cleavable.

In some embodiments, the heterologous moiety is linked (e.g., via a linker or directly), to the polypeptide on an amino terminus, a carboxy terminus, both termini, or one or more amino acids of the polypeptide. In some embodiments, a provided composition further comprises a linker, e.g., between polypeptides or between the polypeptide and the heterologous moiety. A linker may be a chemical bond, e.g., one or more covalent bonds or non-covalent bonds. In some embodiments, a linker is a peptide linker (e.g., a non ABX"C polypeptide). Such a linker may be between 2-30 amino acids, or longer. A linker may be or comprise flexible, rigid or cleavable linkers as described herein.

In some embodiments, the polypeptide as described herein has the capacity to form linkages, e.g., after administration, to a heterologous moiety as described herein, e.g., an effector molecule, e.g., a nucleic acid, protein, peptide or other molecule, or other agent, e.g., intracellular molecules, such as through covalent bonds or non-covalent bonds.

Methods as described in various embodiments of any above aspects may be utilized in any other aspects delineated herein.

In some aspects, the present disclosure provides pharmaceutical compositions comprising two or more polypeptides with each comprising at least one sequence of AMT. A is selected from a hydrophobic amino acid or an amide containing backbone, e.g., aminoethyl-glycine, with a nucleic acid side chain. B and C may be the same or different, and are each independently selected from arginine (Arg, R), asparagine (Asn, N), glutamine (Gln, Q), lysine (Lys, K), and analogs thereof. X is each independently an amide containing backbone, e.g., aminoethyl-glycine, with a nucleic acid side chain. N is an integer from 1 to 4.

A composition as described in various embodiments of any above aspects may be utilized in any other aspects delineated herein.

In some embodiments, a hydrophobic amino acid is selected from alanine (Ala, A), glycine (Gly, G), valine (Val, V), isoleucine (Ile, I), leucine (Leu, L), methionine (Met, M), phenylalanine (Phe, F), tyrosine (Tyr, Y), tryptophan (Trp, W), and analogs thereof. In some embodiments, a hydrophobic amino acid does not include glycine. In some embodiments, B is selected from arginine or glutamine. In some embodiments, C is arginine. In some embodiments, n is 2.

In some embodiments, the polypeptides have sizes in the range of about 5 to about 50 amino acid units in length.

In some embodiments, the polypeptides are linked to one another, e.g., amino acids on one polypeptide are linked with one or more amino acids or a carboxy or amino terminal on another polypeptide, branched polypeptide, or through new peptide bonds, linear polypeptide. In some embodiments, the polypeptides are linked by a linker as described herein.

In some embodiments, a nucleic acid side chain is independently selected from the group consisting of a purine side chain, a pyrimidine side chain, and a nucleic acid analog side chain. In some embodiments, a nucleic acid side chain hybridizes to the heterologous moiety, wherein the heterologous moiety comprises a nucleic acid side chain, e.g., a PNA, or nucleic acid.

In some embodiments, a provided composition further comprises at least one heterologous moiety. In some embodiments, the heterologous moiety is selected from the group consisting of a small molecule (e.g., a drug), a peptide (e.g., ligand), a peptide nucleic acid (PNA), and a nucleic acid (e.g., siRNA, DNA, modified RNA, RNA).

In some embodiments, the heterologous moiety possesses at least one effector activity selected from the group consisting of modulates a biological activity, binds a regulatory protein, modulates enzymatic activity, modulates substrate binding, modulates receptor activation, modulates protein stability/degradation, and modulates transcript stability/degradation.

In some embodiments, the heterologous moiety possesses at least one targeted function selected from the group consisting of modulates a function, modulates a molecule (e.g., enzyme, protein or nucleic acid), and is localized to a specific location.

In some embodiments, the heterologous moiety is or comprises a tag or label, e.g., cleavable.

In some embodiments, the heterologous moiety is selected from the group consisting of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR system or component thereof, DNA, RNA, artificial nucleic acids, a nanoparticle, an oligonucleotide aptamer, a peptide aptamer, and an agent with poor pharmacokinetics or pharmacodynamics (PK/PD).

In some embodiments, the heterologous moiety is cleavable.

In some embodiments, a provided composition further comprises two or more heterologous moieties linked, e.g., via a linker or directly, to the polypeptide on amino termini, on carboxy termini, all termini, a combination of some carboxy and some amino termini of the polypeptides, one or more amino acids of the polypeptide, or any combination thereof. In some embodiments, the heterologous moiety is linked, e.g., via a linker or directly, to one of the polypeptides on an amino terminus, a carboxy terminus, both termini, or one or more amino acids of the polypeptide.

In some embodiments, a composition further comprises a linker, e.g., between polypeptides or between the polypeptide and the heterologous moiety. A linker may be a chemical bond, e.g., one or more covalent bonds or non-covalent bonds. In some embodiments, a linker is a peptide linker (e.g., a non ABX"C polypeptide). Such a linker may be between 2-30 amino acids, or longer. A linker may be or comprise flexible, rigid, or cleavable linkers described herein.

In some embodiments, the polypeptides described herein (e.g., two or more polypeptides) have the capacity to form linkages, e.g., after administration, to other polypeptides, to a heterologous moiety as described herein, e.g., an effector molecule, e.g., a nucleic acid, protein, peptide or other molecule, or other agent, e.g., intracellular molecules, such as through covalent bonds or non-covalent bonds.

In some aspects, the present disclosure provides methods of delivering a therapeutic comprising administering two or more polypeptides with each comprising at least one sequence of ABX"C, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein to a subject. In some embodiments, the heterologous moiety is a therapeutic, and a composition increases intracellular delivery of the therapeutic as compared to a therapeutic alone. In some embodiments, for example, a composition (comprising a therapeutic) increases intracellular delivery of a therapeutic at least 5%, 10%, 15%, 20%, 30%, 40%, 50%, 60%, 75%, 80%, 90% or more, as compared to the therapeutic alone.

Methods as described in various embodiments of any above aspects may be utilized in any other aspects delineated herein.

In some embodiments, a composition is targeted to one or more specific tissues and/or cells. In some embodiments, for example, a composition is targeted to an epithelial, connective, muscular, or nervous tissue or cells, or combinations thereof. In some embodiments, a composition is targeted one or more tissues or cells of a particular organ system, e.g., cardiovascular system (heart, vasculature); digestive system (esophagus, stomach, liver, gallbladder, pancreas, intestines, colon, rectum and anus); endocrine system (hypothalamus, pituitary gland, pineal body or pineal gland, thyroid, parathyroid, adrenal glands); excretory system (kidneys, ureters, bladder); lymphatic system (lymph, lymph nodes, lymph vessels, tonsils, adenoids, thymus, spleen); integumentary system (skin, hair, nails); muscular system (e.g., skeletal muscle); nervous system (brain, spinal cord, nerves); reproductive system (ovaries, uterus, mammary glands, testes, vas deferens, seminal vesicles, prostate); respiratory system (pharynx, larynx, trachea, bronchi, lungs, diaphragm); skeletal system (bone, cartilage), and combinations thereof. In some embodiments, a composition crosses a blood-brain-barrier, a placental membrane, or a blood-testis barrier.

In some embodiments, a composition is administered systemically. In some embodiments, administration is non-parenteral and a therapeutic is a parenteral therapeutic.

In some embodiments, a composition has improved PK/PD, e.g., increased pharmacokinetics or pharmacodynamics, such as improved targeting, absorption, or transport (e.g., at least 5%, 10%, 15%, 20%, 30%, 40%, 50%, 60%, 75%, 80%, 90% improved or more) as compared to a therapeutic alone. In some embodiments, a composition has reduced undesirable effects, such as reduced diffusion to non-target location, off-target activity, or toxic metabolism, as compared to the therapeutic alone (e.g., at least 5%, 10%, 15%, 20%, 30%, 40%, 50%, 60%, 75%, 80%, 90% or more reduced, as compared to the therapeutic alone). In some embodiments, a composition (comprising a therapeutic) increases efficacy and/or decreases toxicity of a therapeutic (e.g., at least 5%, 10%, 15%, 20%, 30%, 40%, 50%, 60%, 75%, 80%, 90% or more) as compared to a therapeutic alone.

In some aspects, the present disclosure provides methods of intracellular delivery of a therapeutic comprising contacting a cell with two or more polypeptides with each comprising at least one sequence of $ABX^nC$, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein. The heterologous moiety is a therapeutic, and a provided composition (comprising a therapeutic) increases intracellular delivery of a therapeutic as compared to a therapeutic alone.

Methods as described in various embodiments of any above aspects may be utilized in any other aspects delineated herein.

In some embodiments, a composition (comprising a therapeutic) has differential PK/PD as compared to the therapeutic alone. In some embodiments, for example, a composition exhibits increased or decreased absorption or distribution, metabolism or excretion (e.g., at least 5%, 10%, 15%, 20%, 30%, 40%, 50%, 60%, 75%, 80%, 90% or more increased or decreased), as compared to a therapeutic alone.

In some embodiments, a composition (comprising a therapeutic) is administered at a dose sufficient to increase intracellular delivery of a therapeutic without significantly increasing endocytosis, e.g., less than about 50%, 40%, 20%, 15%, 10%, 5%, 4%, 3%, 2%, 1%, or any percentage therebetween. In some embodiments, a composition is administered at a dose sufficient to increase intracellular delivery of a therapeutic without significantly increasing calcium influx, e.g., less than about 50%, 40%, 20%, 15%, 10%, 5%, 4%, 3%, 2%, 1%, or any percentage therebetween. In some embodiments, a composition (comprising a therapeutic) is administered at a dose sufficient to increase intracellular delivery of a therapeutic without significantly increasing endosomal activity, e.g., less than about 50%, 40%, 20%, 15%, 10%, 5%, 4%, 3%, 2%, 1%, or any percentage therebetween.

In some aspects, the present disclosure provides methods of modulating transcription of a gene in a cell comprising contacting the cell with two or more polypeptides with each comprising at least one sequence of $ABX"C$, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein. A composition as described herein may target a gene and modulates its transcription.

Methods as described in various embodiments of any above aspects may be utilized in any other aspects delineated herein.

In some embodiments, a composition is administered in an amount and for a time sufficient to effect intracellular delivery of the therapeutic with decreased off target transcriptional activity compared to the heterologous moiety alone, e.g., without significantly altering off-target transcriptional activity.

In some aspects, the present disclosure provides methods of modulating a membrane protein, e.g., such as an ion channel, a cell surface receptor and a synaptic receptor, on a cell comprising contacting the cell with two or more polypeptides with each comprising at least one sequence of $ABX"C$, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein. A composition targets a cell and modulates a membrane protein.

Methods as described in various embodiments of any above aspects may be utilized in any other aspects delineated herein.

In some aspects, the present disclosure provides methods of inducing cell death comprising contacting a cell with two or more polypeptides with each comprising at least one sequence of $ABX"C$, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently amide containing backbone, e.g., aminoethyl-glycine, with a nucleic acid side chain; and n is an integer from 1 to 4, or a composition as described herein, wherein a composition targets the cell and induces apoptosis.

Methods as described in various embodiments of any above aspects may be utilized in any other aspects delineated herein.

In some embodiments, a composition targets a cell harboring a viral DNA sequence or a mutation in a gene.

In some embodiments, the cell is virally infected.

In some embodiments, the cell harbors a genetic mutation.

In some embodiments, a composition targets a cell in the early stages of necrosis, e.g., binding a necrotic cell marker.

In some aspects, the present disclosure provides methods of increasing bioavailability of a therapeutic comprising administering two or more polypeptides with each comprising at least one sequence of $ABX"C$, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition described herein and the therapeutic is the heterologous moiety.

Methods as described in various embodiments of any above aspects may be utilized in any other aspects delineated herein.

In some embodiments, a composition improves (comprising a therapeutic) (e.g., by at least 5%, 10%, 15%, 20%, 30%, 40%, 50%, 60%, 75%, 80%, 90% or more) at least one PK/PD parameter, such as improved targeting, absorption, or transport, as compared to a therapeutic alone. In some embodiments, to composition (comprising a therapeutic) reduces (e.g., by at least 5%, 10%, 15%, 20%, 30%, 40%, 50%, 60%, 75%, 80%, 90% or more) at least one unwanted parameter, such as reduced diffusion to non-target location, off-target activity, or toxic metabolism, as compared to a therapeutic alone. In some embodiments, a composition (comprising a therapeutic) increases efficacy and/or decreases toxicity of a therapeutic as compared to a therapeutic alone.

In some aspects, the present disclosure provides methods of treating an acute or chronic infection comprising administering two or more polypeptides with each comprising at least one sequence of ABX"C, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein.

Methods as described in various embodiments of any above aspects may be utilized in any other aspects delineated herein.

In some embodiments, a composition targets an infected cell harboring a pathogen. In some embodiments, an infection is caused by a pathogen selected from the group consisting of a virus, bacteria, parasite, and a prion. In some embodiments, a composition induces cell death in an infected cell, e.g., the heterologous moiety is, e.g., an antibacterial, an antiviral, or an antiparasitic therapeutic.

In some aspects, the present disclosure provides methods of treating a cancer comprising administering two or more polypeptides with each comprising at least one sequence of ABX"C, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein.

Methods as described in various embodiments of any above aspects may be utilized in any other aspects delineated herein.

In some embodiments, the heterologous moiety is a therapeutic that modulates gene expression of one or more genes.

In some embodiments, a composition may target a cancer cell harboring a mutation in a gene. In some embodiments, a composition induces cell death in the cancer cell, e.g., the heterologous moiety is e.g., a chemotherapeutic agent.

In some aspects, the present disclosure provides methods of treating a neurological disease or disorder comprising administering two or more polypeptides with each comprising at least one sequence of ABX"C, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein.

Methods as described in various embodiments of any above aspects may be utilized in any other aspects delineated herein.

In some embodiments, a composition modulates neuroreceptor activity or activation of, e.g., a neurotransmitter, neuropeptide, or neuroreceptor.

In some aspects, the present disclosure provides methods of treating a disease/disorder/condition in a subject comprising administering two or more polypeptides with each comprising at least one sequence of ABX"C, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein and a composition modulates transcription to treat a disease/disorder/condition.

Methods as described in various embodiments of any above aspects may be utilized in any other aspects delineated herein.

In some embodiments, a disease/disorder/condition is a genetic disease.

In some aspects, the present disclosure provides methods of inducing immune tolerance comprising providing two or more polypeptides with each comprising at least one sequence of ABX"C, wherein A is selected from a hydrophobic amino acid or an amide containing backbone, e.g., aminoethyl-glycine, with a nucleic acid side chain; B and C may be the same or different, and are each independently selected from arginine (Arg, R), asparagine (Asn, N), glutamine (Gln, Q), lysine (Lys, K), and analogs thereof; X is each independently an amide containing backbone, e.g., aminoethyl-glycine, with a nucleic acid side chain; and n is an integer from 1 to 4, or a composition as described herein, e.g., the heterologous moiety is an antigen.

Methods as described in various embodiments of any above aspects may be utilized in any other aspects delineated herein.

Definitions

As used herein, "amino acid unit" is unit encompassing an amide bond and a corresponding side chain.

As used herein, a "heterologous moiety" is an entity other than a ABX"C polypeptide, which is linked to a ABX"C polypeptide described herein. The heterologous moiety may be or comprise, e.g., a targeting moiety or an effector moiety (e.g., a moiety that is capable of modulating a cell function, e.g., a drug). The heterologous moiety may be, e.g., a small molecule, a peptide or protein, a nucleic acid, a nanoparticle, or a combination thereof).

As used herein, a "pseudo-5' to pseudo-3' nucleotide sequence" is a nucleotide sequence formed by sequential alignment of nucleic acid side chains from multiple polypeptides, e.g., the 5' sequence starts at the amino terminal nucleic acid side chain on a polypeptide through the carboxy terminal nucleic acid side chain on that polypeptide to the amino terminal nucleic acid side chain on a second polypeptide through the carboxy terminal nucleic acid side chains on the second polypeptide to the amino terminal nucleic acid side chain on a third polypeptide etc.

As used herein, "toxicity" is a harmful quality or adverse effect of an agent after administration.

DETAILED DESCRIPTION OF CERTAIN EMBODIMENTS

Compositions

Figure 1:
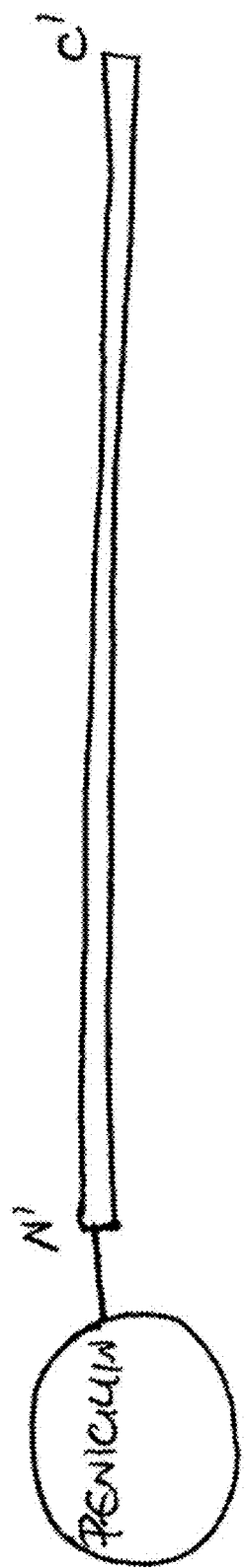
FIG. 1 is an illustration of a polypeptide alpha linked to penicillin.

The present disclosure provides compositions, e.g., therapeutic compositions, and related therapeutic methods. In some aspects, a provided composition comprises a polypeptide described herein and a heterologous moiety. Compositions described herein have properties that may allow translocation across a membrane, for example, independent of endosomes, such that a composition is delivered to a target location within a cell, e.g., within a subject. Target location may be intracellular, e.g., cytosolic or intra-organellar (e.g., intranuclear, such as a target DNA sequence or chromatin structure). Therapeutic compositions as described herein may have advantageous properties, such as improved targeting, absorption, or transport, or reduced off-target activity, toxic metabolism, or toxic excretion.

Polypeptide

In some embodiments, a provided composition includes at least one polypeptide, with each comprising a sequence:

AB$X^n$C, wherein:

A is a hydrophobic amino acid;

B and C may be the same or different, and are independently selected from arginine (Arg, R), asparagine (Asn, N), glutamine (Glu, Q), lysine (Lys, K), and analogs thereof; are independently selected from arginine (Arg, R), asparagine (Asn, N), glutamine (Gln, Q), lysine (Lys, K), and analogs thereof;

n is an integer from 1 to and in some embodiments (which may be referred to herein as "alpha polypeptide embodiments"), X is each independently a hydrophobic amino acid; or alternatively, in some embodiments (which may be referred to herein as "beta polypeptide embodiments"), X is each independently an amide containing backbone, e.g., aminoethyl-glycine, with a nucleic acid side chain (e.g., as in a peptide nucleic acid "PNA").

In some embodiments (which may be referred to herein as "gamma polypeptide" embodiments), a provided composition comprises two or more beta polypeptides.

Hydrophobic amino acids include amino acids having hydrophobic side chains and include, but are not limited to, alanine (Ala, A), glycine (Gly, G), valine (Val, V), isoleucine (Ile, I), leucine (Leu, L), methionine (Met, M), phenylalanine (Phe, F), tyrosine (Tyr, Y), tryptophan (Trp, W), and analogs thereof. In some embodiments, hydrophobic amino acids do not include glycine.

In many embodiments, a provided composition includes at least one alpha, beta, or gamma polypeptide as described herein, and further includes at least one heterologous moiety (e.g., cargo) associated with the polypeptide(s), e.g., by covalent association. In some embodiments, such covalent association may be direct linkage; in some embodiments, such covalent association may be by way of a linker. In some embodiments, covalent association between a heterologous moiety and a polypeptide as described herein is labile (e.g., cleavable or otherwise susceptible to disruption), for example when exposed to a condition such as an interior of a cell or organelle thereof.

arginine (Arg, R), asparagine (Asn, N), glutamine (Gln, Q), lysine (Lys, K) arginine (Arg, R), asparagine (Asn, N), glutamine (Gln, Q), lysine (Lys, K) arginine (Arg, R), asparagine (Asn, N), glutamine (Gln, Q), lysine (Lys, K) Amino acid analogs include, but are not limited to, D-amino acids, amino acids lacking a hydrogen on the α-carbon such as dehydroalanine, metabolic intermediates such as ornithine and citrulline, non-alpha amino acids such as β-alanine, γ-aminobutyric acid, and 4-aminobenzoic acid, twin α-carbon amino acids such as cystathionine, lanthionine, djenkolic acid and diaminopimelic acid, and any others known in the art.

Nucleic Acid Side Chains

In some embodiments, a "polypeptide" as described herein, is or comprises one or more peptide nucleic acids ("PNA"s). As is known in the art, a PNA includes one or more nucleic acid base side chains linked to an amide backbone.

Specifically, a canonical PNA has a backbone comprising repeating N-(2-aminoethyl)-glycine units that are linked to one another by peptide bonds. Purine or pyrimidine bases are linked to the nitrogen of the N-(2-aminoethyl)-glycine backbone units via a methylene bridge (—$CH_2$—) and a carbonyl group (—(C=O)—).

Peptide nucleic acids (PNA) are known to hybridize complementary DNA and RNA with higher affinity than their oligonucleotide counterparts. This character of PNA not only makes the polypeptide of the present disclosure a stable hybrid with the nucleic acid side chains, but at the same time, the neutral backbone and hydrophobic side chains result in a hydrophobic unit within the polypeptide.

A nucleic acid side chain is or comprises a purine or a pyrimidine side chain such as adenine, cytosine, guanine, thymine and uracil. In some embodiments, the nucleic acid side chain includes a nucleoside analog, such as 5-fluorouracil; 5-bromouracil, 5-chlorouracil, 5-iodouracil, hypoxanthine, xanthine, 4-acetylcytosine, 4-methylbenzimidazole, 5-(carboxyhydroxylmethyl) uracil, 5-carboxymethylaminomethyl-2-thiouridine, 5-carboxymethylaminomethyluracil, dihydrouracil, dihydrouridine, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, 3-nitropyrrole, inosine, thiouridine, queuosine, wyosine, diaminopurine, isoguanine, isocytosine, diaminopyrimidine, 2,4-difluorotoluene, isoquinoline, pyrrolo[2,3-β]pyridine, and any others that can base pair with a purine or a pyrimidine side chain.

Size

In some embodiments, a provided polypeptide has a size in the range of about 5 to about 500, e.g., 5-400, 5-300, 5-250, 5-200, 5-150, 5-100 amino acid units in length. The polypeptide may have a length in the range of about 5 to about 50 amino acids, about 5 to about 40 amino acids, about 5 to about 30 amino acids, about 5 to about 25 amino acids, or any other range. In some embodiments, the polypeptide has a length of about 10 amino acids. In some embodiments, the polypeptide has a length of about 15 amino acids. In some embodiments, the polypeptide has a length of about 20 amino acids. In some embodiments, the polypeptide has a length of about 25 amino acids. In some embodiments, the polypeptide has a length of about 30 amino acids.

Multimerization of Polypeptides

A composition according to the present disclosure may include a plurality (two or more) of polypeptides linked together, e.g., through a linker described herein.

A composition may include a plurality of polypeptides that are the same or different. In some embodiments, at least two of the plurality are identical in sequence and/or length. In some embodiments, at least two of the plurality are different in sequence and/or length. In some embodiments, a composition includes a plurality of polypeptides wherein at least two of the plurality are the same and at least 2 of the plurality are different. In some embodiments, the polypeptides in a composition are not identical in sequence or length or a combination thereof.

A composition comprising a plurality of polypeptides includes a polypeptide that is linked to another polypeptide, e.g., by a linker. In some embodiments, a composition includes two or more polypeptides linked by a linker. In some embodiments, a composition includes three or more polypeptides linked by linkers. In some embodiments, a composition includes four or more polypeptides linked by linkers. In some embodiments, a composition includes five or more polypeptides linked by linkers. A linker may be a chemical bond, e.g., one or more covalent bonds or non-covalent bonds, e.g., a flexible, rigid or cleavable peptide linker. Such a linker may be between 2-30 amino acids, or longer. Additional linkers are described in more detail elsewhere herein and are also applicable.

In some embodiments, two or more polypeptides are linked through a peptide bond, for example a carboxyl terminal of one polypeptide is bonded to the amino terminal of another polypeptide. In some embodiments, one or more amino acids on one polypeptide are linked with one or more amino acids on another polypeptide, such as through disulfide bonds between cysteine side chains. In some embodiments, one or more amino acids on one polypeptide are linked with a carboxyl or amino terminal on another polypeptide, such as to create a branched polypeptide.

In some embodiments, one or more nucleic acid side chains on one polypeptide may interact with one or more amino acid side chains on another polypeptide, such as through arginine forming a pseudo-pairing with guanosine. In some embodiments, one or more nucleic acid side chains on one polypeptide may interact with one or more nucleic acid side chains on another polypeptide, such as through hydrogen bonding. In some embodiments, multiple polypeptides interact to create a specific sequence in the arrangement of a nucleic acid side chains. In some embodiments, for example, a carboxy terminal nucleic acid side chain from one polypeptide may interact with an amino terminal nucleic acid side chain from another polypeptide to create a pseudo-5' to pseudo-3' nucleotide sequence. In some embodiments some embodiments, a polypeptide is linked with one or more polypeptides, such as through amino acids and/or terminus on each polypeptide, and their respective nucleic acid side chains align to create a pseudo-5' to pseudo-3' nucleotide sequence. A pseudo-sequence may bind a selected target sequence, such as a transcriptional control sequence, e.g., an enhancer or silencer. A pseudo-sequence may interfere with factor binding and transcription by binding to a target sequence. A pseudo-sequence may hybridize with a nucleic acid sequence, such as an mRNA to interfere with gene expression.

Polypeptides as described herein can be multimerized, e.g., linking two or more polypeptides, by employing standard ligation techniques. Such methods include, general native chemical ligation strategies (Siman, P. and Brik, A. Org. Biomol. Chem. 2012, 10:5684-5697; Kent, S. B. H. Chem. Soc. Rev. 2009, 38:338-351; and Hackenberger, C. P. R. and Schwarzer, D. Angew. Chem., Int. Ed. 2008, 47:10030-10074), click modification protocols (Tasdelen, M. A.; Yagci, Y. Angew. Chem., Int. Ed. 2013, 52:5930-5938; Palomo, J. M. Org. Biomol. Chem. 2012, 10:9309-9318; Eldijk, M. B.; van Hest, J. C. M. Angew. Chem., Int. Ed. 2011, 50:8806-8827; and Lallana, E.; Riguera, R.; Fernandez-Megia, E. Angew. Chem., Int. Ed. 2011, 50:8794-8804), and bioorthogonal reactions (King, M.; Wagner, A. Bioconjugate Chem. 2014, 25:825-839; Lang, K.; Chin, J. W. Chem. Rev. 2014, 114:4764-4806; Patterson, D. M.; Nazarova, L. A.; Prescher, J. A. ACS Chem. Biol. 2014, 9:592-605; Lang, K.; Chin, J. W. ACS Chem. Biol. 2014, 9:16-20; Takaoka, Y.; Ojida, A.; Hamachi, I. Angew. Chem., Int. Ed. 2013, 52:4088-4106; Debets, M. F.; van Hest, J. C. M.; Rutjes, F. P. J. T. Org. Biomol. Chem. 2013, 11:6439-6455; and Ramil, C. P.; Lin, Q. Chem. Commun. 2013, 49:11007-11022).

In some embodiments, ordering of polypeptides in a multimer is specific or it may be random, e.g., when the polypeptides are not identical. In some embodiments, for example, polypeptides as described herein may be multimerized by template driven synthesis or multimerization is ordered by physical constraints or hybridization to a provided template, e.g., DNA, protein, hybrid DNA-protein. In some embodiments, a template, e.g., a DNA sequence, specifically hybridizes to a polypeptide described herein. A polypeptide may be linked to another polypeptide via a method as described herein, e.g., general chemical ligation, and the choice of which polypeptide is linked may be constrained by the ability to hybridize to a given template. Thus, a specific polypeptide multimer may be generated by its ability to specifically hybridize to a given template.

In some embodiments, order of polypeptides in a provided multimer is determined by chemical ligation strategy used. In some embodiments, chemical ligation techniques, such as click chemistry and bioorthogonal reactions, direct which polypeptides are linked because a given chemical ligation strategy may require specific entities to react for a given ligation technique to proceed. In some embodiments, for example, one polypeptide may be labeled with a phenyl azide and another polypeptide is labeled with cyclooctyne. Cyclooctyne and phenyl azide react to link the two polypeptides.

In some embodiments, a provided polypeptide may have more than one sequence of ABX"C within its length. Each ABX"C sequence may be separated from another ABX"C sequence by one or more amino acids. In some embodiments, the polypeptide repeats the ABX"C sequence and separates the sequences by one or more amino acid units. In some embodiments, the polypeptide includes at least two (e.g., 2, 3, 4, 5, 6, 7, 8, 9, 10, 11, 12, 13, 14, 15 or more, e.g., between 2-20, between 2-10, between 2-5) ABX"C sequences and separates the sequences by one or more amino acid units. In some embodiments, the ABX"C sequences are separated by one (or more) hydrophobic amino acid, such as isoleucine or leucine.

A provided composition may include a plurality of ABX"C sequences that are the same or different. In some embodiments, at least two of a plurality are identical in sequence and/or length. In some embodiments, at least two of a plurality are different in sequence and/or length. In some embodiments, a composition includes a plurality of ABX"C sequences wherein at least two of a plurality are the same and at least 2 of a plurality are different. In some embodiments, the ABX"C sequences in the polypeptide are not identical in sequence or length or a combination thereof.

Hybridization

In certain embodiments where the polypeptide includes nucleic acid side chains (e.g., wherein the polypeptide is or comprises a PNA), it is capable of interacting with nucleic acids. In some embodiments, one or more nucleic acid side chains on the polypeptide hybridize with a nucleic acid sequence, e.g., a DNA such as genomic DNA, RNA such as siRNA or mRNA molecule. One or more of the nucleic acid side chains on the polypeptide specifically hybridize with one or more nucleic acid residues in a target nucleic acid sequence. In some embodiments, the polypeptides are linked to one another and the nucleic acid side chains are capable of hybridizing a nucleic acid sequence (e.g., gene locus, mRNA).

Nucleic acid side chains or pseudo-sequence of nucleic acid side chains may hybridize a target nucleic acid sequence that is substantially matched to hybridize or 100%, 95%, 90%, 85%, 80%, 75%, or 70% complementary to nucleic acid side chains or pseudo-sequence of nucleic acid side chains. Hybridization of nucleic acid side chains or pseudo-sequence of nucleic acid side chains with a target nucleic acid sequence may be carried out under suitable hybridization conditions routinely determined by optimization procedures. Conditions such as temperature, concentration of components, hybridization and washing times, buffer components, and their pH and ionic strength may be varied depending on various factors, including length and GC content of nucleic acid side chains or pseudo-sequence of nucleic acid side chains and complementary target nucleic acid sequence. In some embodiments, for example, when a relatively short length of nucleic acid side chains or pseudo-sequence of nucleic acid side chains is used, lower stringent conditions may be adopted. Detailed conditions for hybridization can be found in Molecular Cloning, A laboratory manual, fourth edition (Cold Spring Harbor Laboratory Press, 2012) or the like.

Production of Polypeptides

As one of skill in the art will appreciate, polypeptides of a compositions provided herein can be biochemically synthesized by employing standard solid phase techniques. Such methods include exclusive solid phase synthesis, partial solid phase synthesis methods, fragment condensation, classical solution synthesis. These methods can be used when the peptide is relatively short (i.e., 10 kDa) and/or when it cannot be produced by recombinant techniques (i.e., not encoded by a nucleic acid sequence) and therefore involves different chemistry.

Solid phase polypeptide synthesis procedures are well known in the art and further described by John Morrow Stewart and Janis Dillaha Young, *Solid Phase Peptide Syntheses,* 2nd Ed., Pierce Chemical Company, 1984; and Coin, I., et al., Nature Protocols, 2:3247-3256, 2007.

For longer peptides, recombinant methods may be used. Methods of making a recombinant therapeutic polypeptide are routine in the art. See, in general, Smales & James (Eds.), *Therapeutic Proteins: Methods and Protocols (Methods in Molecular Biology),* Humana Press (2005); and Crommelin, Sindelar & Meibohm (Eds.), *Pharmaceutical Biotechnology: Fundamentals and Applications,* Springer (2013).

Preferred methods for producing a therapeutic pharmaceutical polypeptide involve expression in mammalian cells, although recombinant proteins can also be produced using insect cells, yeast, bacteria, or other cells under the control of appropriate promoters. Mammalian expression vectors may comprise nontranscribed elements such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green & Sambrook, *Molecular Cloning: A Laboratory Manual (Fourth Edition),* Cold Spring Harbor Laboratory Press (2012).

Various mammalian cell culture systems may be employed to express and manufacture recombinant protein. Non-limiting examples of mammalian expression systems include CHO cells, COS cells, HeLA and BHK cell lines. Processes of host cell culture for production of protein therapeutics are described in Zhou and Kantardjieff (Eds.), *Mammalian Cell Cultures for Biologics Manufacturing (Advances in Biochemical Engineering/Biotechnology),* Springer (2014).

Purification of protein therapeutics is described in Franks, *Protein Biotechnology: Isolation, Characterization, and Stabilization,* Humana Press (2013); and in Cutler, Protein Purification Protocols (Methods in Molecular Biology), Humana Press (2010).

In cases where large amounts of a polypeptide are desired, it can be generated using techniques such as described by Brian Bray, Nature Reviews Drug Discovery, 2:587-593, 2003; and Weissbach & Weissbach, 1988, *Methods for Plant Molecular Biology,* Academic Press, NY, Section VIII, pp 421-463.

Heterologous Moiety

In some aspects, provided compositions as described herein also include one or more heterologous moiety(ies) linked to a polypeptide described herein. A heterologous moiety may comprise one or more of an effector (e.g., a drug, small molecule), a targeting agent (e.g., a DNA targeting agent, antibody, receptor ligand), or a tag (e.g., fluorophore, light sensitive agent such as KillerRed). In some embodiments, a polypeptide described herein is linked to two heterologous moieties.

In some embodiments, a heterologous moiety is or comprises an effector (e.g. drug, small molecule).

In some embodiments, a heterologous moiety is or comprises a targeting agent (e.g., a DNA targeting agent, antibody, receptor ligand).

In some embodiments, a heterologous moiety is or comprises a tag (e.g., fluorophore, light sensitive agent such as KillerRed).

In some embodiments, the heterologous moiety is or comprises one or more of a small molecule (e.g., a peptidomimetic or a small organic molecule with a molecular weight of less than 2000 daltons), a peptide or polypeptide (e.g., a non ABX"C polypeptide, e.g., an antibody or antigen-binding fragment thereof), a nucleic acid (e.g., siRNA, mRNA, RNA, DNA, an antisense RNA, a ribozyme, a therapeutic mRNA encoding a protein), a nanoparticle, an aptamer, and pharmacoagent with poor PK/PD.

In some embodiments, a heterologous moiety is or comprises a small molecule (e.g., a peptidomimetic or a small organic molecule with a molecular weight of less than 2000 daltons).

In some embodiments, a heterologous moiety is or comprises a peptide or polypeptide (e.g., a non ABX"C polypeptide, e.g., an antibody or antigen-binding fragment thereof).

In some embodiments, a heterologous moiety is or comprises a nucleic acid (e.g., siRNA, mRNA, RNA, DNA, an antisense RNA, a ribozyme, a therapeutic mRNA encoding a protein).

In some embodiments, a heterologous moiety is or comprises a nanoparticle.

In some embodiments, a heterologous moiety is or comprises an aptamer.

In some embodiments, a heterologous moiety is or comprises a pharmacoagent with poor PK/PD.

In some embodiments, the heterologous moiety may cleaved from the polypeptide (e.g., after administration) by specific proteolysis or enzymatic cleavage (e.g. by TEV protease, Thrombin, Factor Xa or Enteropeptidase). Effector activity A heterologous moiety may possess effector activity. In some embodiments, effector activities may be or comprise modulating a biological activity, for example increasing or decreasing enzymatic activity, gene expression, cell signaling, and cellular or organ function. In some embodiments, effector activities may be or comprise binding regulatory proteins to modulate activity of the regulator, such as transcription or translation. In some embodiments, effector activities may be or comprise activator or inhibitor functions. In some embodiments, the heterologous moiety may induce enzymatic activity by triggering increased substrate affinity in an enzyme, e.g., fructose 2,6-bisphosphate activates phosphofructokinase 1 and increases the rate of glycolysis in response to the insulin. In some embodiments, the heterologous moiety may inhibit substrate binding to a receptor and inhibit its activation, e.g., naltrexone and naloxone bind opioid receptors without activating them and block the receptors' ability to bind opioids. In some embodiments, effector activities may be or comprise modulating protein stability/degradation and/or transcript stability/degradation. In some embodiments, proteins may be targeted for degradation by the polypeptide co-factor, ubiquitin, onto proteins to mark them for degradation. In some embodiments, the heterologous moiety inhibits enzymatic activity by blocking the enzyme's active site, e.g., methotrexate is a structural analog of tetrahydrofolate, a coenzyme for the enzyme dihydrofolate reductase that binds to dihydrofolate reductase 1000-fold more tightly than the natural substrate and inhibits nucleotide base synthesis.

In some embodiments, the heterologous moiety with effector activity may be any one or more of small molecules, peptides, nucleic acids, nanoparticles, aptamers, and/or pharmacoagents with poor PK/PD described herein.

Targeted Function

A heterologous moiety may have targeted function. A targeted function may be or comprise modulating a specific function, modulating a specific molecule (e.g., enzyme, protein or nucleic acid), and specific binding for localization. A targeted function may act on a specific molecule, e.g. a molecular target. In some embodiments, a heterologous moiety may include a targeted therapeutic that interacts with a specific molecular target to increase, decrease or otherwise modulate its function.

A heterologous moiety with targeted function may be any one or more of small molecules, peptides, nucleic acids, nanoparticles, aptamers, and/or pharmacoagents with poor pharmacokinetics described herein.

Tagging or Monitoring

A heterologous moiety may be useful for as a tag to label or monitor the polypeptide described herein or another heterologous moiety linked to the polypeptide. A tag may be removable by chemical agents or enzymatic cleavage, such as proteolysis or intein splicing. An affinity tag may be useful to purify the tagged polypeptide using an affinity technique. In some embodiments, for example a tag may be or comprise, chitin binding protein (CBP), maltose binding protein (MBP), glutathione-S-transferase (GST), and poly (His) tag. A solubilization tag may be useful to aid recombinant proteins expressed in chaperone-deficient species such as E. coli to assist in the proper folding in proteins and keep them from precipitating. In some embodiments, for example a solubilization tag may be or comprise include thioredoxin (TRX) and poly(NANP). The tag may include a light sensitive tag, e.g., fluorescence. Fluorescent tags are useful for visualization. Green fluorescent protein (GFP) and its variants are some examples commonly used as fluorescent tags. Protein tags may allow specific enzymatic modifications (such as biotinylation by biotin ligase) or chemical modifications (such as reaction with FlAsH-EDT2 for fluorescence imaging) to occur. Often tags are combined, in order to connect proteins to multiple other components. Tags may also be removed by specific proteolysis or enzymatic cleavage (e.g. by TEV protease, Thrombin, Factor Xa or Enteropeptidase).

The heterologous moiety with targeted function may be a small molecule, peptide, nucleic acid, nanoparticle, aptamer, or other agent.

Small Molecules

A heterologous moiety may be a small molecule. Small molecule moieties include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heterorganic and organometallic compounds) generally having a molecular weight less than about 5,000 grams per mole (wherein those skilled in the art will understand that the unit "daltons" may be used interchangeably with "grams per mole" herein), e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds. Small molecules may include, but are not limited to, a neurotransmitter, a hormone, a drug, a toxin, a viral or microbial particle, a synthetic molecule, and agonists or antagonists. In some embodiments, for example, small molecules may be or comprise, prion drugs such as tacrolimus, ubiquitin ligase or HECT ligase inhibitors such as heclin, histone modifying drugs such as sodium butyrate, enzymatic inhibitors such as 5-aza-cytidine, anthracyclines such as doxorubicin, beta-lactams such as penicillin, anti-bacterials, chemotherapy agents, anti-virals, modulators from other organisms such as VP64, and drugs with insufficient bioavailability such as chemotherapeutics with deficient pharmacokinetics.

In some embodiments, a small molecule is an epigenetic modifying agent, for example such as those described in de Groote et al. Nuc. Acids Res. (2012):1-18. Exemplary small molecule epigenetic modifying agents are described, e.g., in Lu et al. J. Biomolecular Screening 17.5(2012):555-71, e.g., at Table 1 or 2, incorporated herein by reference. In some embodiments, an epigenetic modifying agent comprises vorinostat, romidepsin. In some embodiments, an epigenetic modifying agent comprises an inhibitor of class I, II, III, and/or IV histone deacetylase (HDAC). In some embodiments, an epigenetic modifying agent comprises an activator of SirTI. In some embodiments, an epigenetic modifying agent comprises Garcinol, Lys-CoA, C646, (+)-JQI, I-BET, BICI, MS120, DZNep, UNC0321, EPZ004777, AZ505, AMI-I, pyrazole amide 7b, benzo[d]imidazole 17b, acylated dapsone derivative (e.g., PRMTI), methylstat, 4,4'-dicarboxy-2,2'-bipyridine, SID 85736331, hydroxamate analog 8, tanylcypromie, bisguanidine and biguanide polyamine analogs, UNC669, Vidaza, decitabine, sodium phenyl butyrate (SDB), lipoic acid (LA), quercetin, valproic acid, hydralazine, bactrim, green tea extract (e.g., epigallocatechin gallate (EGCG)), curcumin, sulforphane and/or allicin/diallyl disulfide. In some embodiments, an epigenetic modifying agent inhibits DNA methylation, e.g., is an inhibitor of DNA methyltransferase (e.g., is 5-azacitidine and/or decitabine). In some embodiments, an epigenetic modifying agent modifies histone modification, e.g., histone acetylation, histone methylation, histone sumoylation, and/or histone phosphorylation. In some embodiments, the epigenetic modifying agent is an inhibitor of a histone deacetylase (e.g., is vorinostat and/or trichostatin A).

In some embodiments, an epigenetic modifying agent comprises a construct described in Koferle et al. 2015. Genome Medicine 7.59:1-3 (e.g., at Table 1), incorporated herein by reference.

Peptides or Proteins

A heterologous moiety may be a peptide or protein. Peptide moieties may be or comprise a peptide ligand or antibody fragment that binds a receptor such as an extracellular receptor, neuropeptide, hormone peptide, peptide drug, toxic peptide, viral or microbial peptide, synthetic peptide, and agonist or antagonist peptide.

Peptides moieties may be linear or branched. A peptide has a length from about 5 to about 200 amino acids, about 15 to about 150 amino acids, about 20 to about 125 amino acids, about 25 to about 100 amino acids, or any range therebetween.

Exemplary peptide or protein heterologous moieties used in provided methods and compositions as described herein include, but are not limited to, ubiquitin, bicyclic peptides as ubiquitin ligase inhibitors, transcription factors, DNA and protein modification enzymes such as topoisomerases, topoisomerase inhibitors such as topotecan, DNA methyltransferases such as the DNMT family, protein methyltransferases such as PRMT1 and G9a, DNA demethylases such as the TET family, protein demethylases such as KDM1A, helicases such as DHX9, acetyltransferases, deacetylases, kinases, phosphatases, DNA-intercalating agents such as, e.g., ethidium bromide, SYBR green, and proflavine efflux pump inhibitors such as, e.g., peptidomimetics such as phenylalanine arginyl 6-naphthylamide or quinoline derivatives, nuclear receptor activators and inhibitors, proteasome inhibitors, competitive inhibitors for enzymes such as those involved in lysosomal storage diseases, protein synthesis inhibitors, nucleases (e.g., Cpf1, Cas9, zinc finger nuclease, etc.), and specific domains from proteins, such as KRAB domain.

In some embodiments, a composition includes an epigenetic enzyme (e.g., an enzyme that generates or removes epigenetic marks, e.g., acetylation and/or methylation) linked to the polypeptide. Exemplary peptide moieties with epigenetic enzymatic activity that can be linked to the polypeptide include, but are not limited to, DNA methylases (e.g., DNMT3a, DNMT3b, DNMTL), DNA demethylases (e.g., TET family), histone methyltransferases, histone deacetylase (e.g., HDAC1, HDAC2, HDAC3), sirtuin 1, 2, 3, 4, 5, 6, or 7, lysine-specific histone demethylase 1 (LSD1), histone-lysine-N-methyltransferase (Setdb1), euchromatic histone-lysine N-methyltransferase 2 (G9a), histone-lysine N-methyltransferase (SUV39H1), enhancer of zeste homolog 2 (EZH2), viral lysine methyltransferase (vSET), histone methyltransferase (SET2), and protein-lysine N-methyltransferase (SMYD2).

In some embodiments, for example, peptides may be or comprise fluorescent tags or markers, antigens, antibodies, antibody fragments such as single domain antibodies, ligands and receptors such as glucagon-like peptide-1 (GLP-1), GLP-2 receptor 2, cholecystokinin B (CCKB) and somatostatin receptor, peptide therapeutics such as those that bind to specific cell surface receptors such as G protein-coupled receptors (GPCRs) or ion channels, synthetic or analog peptides from naturally-bioactive peptides, anti-microbial peptides, pore-forming peptides, tumor targeting or cytotoxic peptides, and degradation or self-destruction peptides such as an apoptosis-inducing peptide signal or photosensitizer peptide.

Peptides useful as heterologous moiety described herein also include small antigen-binding peptides, e.g., antigen binding antibody or antibody-like fragments, such as single chain antibodies, nanobodies (see, e.g., Steeland et al. 2016. Nanobodies as therapeutics: big opportunities for small antibodies. Drug Discov Today: 21(7):1076-113). Such small antigen binding peptides may bind a cytosolic antigen, a nuclear antigen, an intra-organellar antigen.

In some embodiments, a composition comprises a polypeptide linked to a ligand that is capable of targeting a specific location, tissue, or cell.

CRISPR

In some embodiments, methods and compositions described herein can be used to improve CRISP-based gene editing, whereby guide RNA (gRNA) are used in a clustered regulatory interspaced short palindromic repeat (CRISPR) system for gene editing. CRISPR systems are adaptive defense systems originally discovered in bacteria and archaea. CRISPR systems use RNA-guided nucleases termed CRISPR-associated or "Cas" endonucleases (e.g., Cas9 or Cpf1) to cleave foreign DNA. In a typical CRISPR/Cas system, an endonuclease is directed to a target nucleotide sequence (e.g., a site in the genome that is to be sequence-edited) by sequence-specific, non-coding "guide RNAs" that target single- or double-stranded DNA sequences. Three classes (I-III) of CRISPR systems have been identified. Class II CRISPR systems use a single Cas endonuclease (rather than multiple Cas proteins). One class II CRISPR system includes a type II Cas endonuclease such as Cas9, a CRISPR RNA ("crRNA"), and a trans-activating crRNA ("tracrRNA"). A crRNA contains a "guide RNA", typically an about 20-nucleotide RNA sequence that corresponds to a target DNA sequence. A crRNA also contains a region that binds to the tracrRNA to form a partially double-stranded structure which is cleaved by RNase III, resulting in a crRNA/tracrRNA hybrid. A crRNA/tracrRNA hybrid then directs the Cas9 endonuclease to recognize and cleave the target DNA sequence. A target DNA sequence must generally be adjacent to a "protospacer adjacent motif" ("PAM") that is specific for a given Cas endonuclease; however, PAM sequences appear throughout a given genome. CRISPR endonucleases identified from various prokaryotic species have unique PAM sequence requirements; examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), and 5'-NNNGATT (*Neisseria meningitidis*). Some endonucleases, e.g., Cas9 endonucleases, are associated with G-rich PAM sites, e.g., 5'-NGG, and perform blunt-end cleaving of the target DNA at a location 3 nucleotides upstream from (5' from) the PAM site. Another class II CRISPR system includes the type V endonuclease Cpf1, which is smaller than Cas9; examples include AsCpf1 (from Acidaminococcus sp.) and LbCpf1 (from Lachnospiraceae sp.). Cpf1-associated CRISPR arrays are processed into mature crRNAs without the requirement of a tracrRNA; in other words a Cpf1 system requires only the Cpf1 nuclease and a crRNA to cleave the target DNA sequence. Cpf1 endonucleases, are associated with T-rich PAM sites, e.g., 5'-TTN. Cpf1 can also recognize a 5'-CTA PAM motif. Cpf1 cleaves the target DNA by introducing an offset or staggered double-strand break with a 4- or 5-nucleotide 5' overhang, for example, cleaving a target DNA with a 5-nucleotide offset or staggered cut located 18 nucleotides downstream from (3' from) from the PAM site on the coding strand and 23 nucleotides downstream from the PAM site on the complimentary strand; the 5-nucleotide overhang that results from such offset cleavage allows more precise genome editing by DNA insertion by homologous recombination than by insertion at blunt-end cleaved DNA. See, e.g., Zetsche et al. (2015) Cell, 163:759-771.

For purposes of gene editing, CRISPR arrays can be designed to contain one or multiple guide RNA sequences corresponding to a desired target DNA sequence; see, for example, Cong et al. (2013) Science, 339:819-823; Ran et al. (2013) Nature Protocols, 8:2281-2308. At least about 16 or 17 nucleotides of gRNA sequence are required by Cas9 for DNA cleavage to occur; for Cpf1 at least about 16 nucleotides of gRNA sequence is needed to achieve detectable DNA cleavage. In practice, guide RNA sequences are generally designed to have a length of between 17-24 nucleotides (e.g., 19, 20, or 21 nucleotides) and complementarity to the targeted gene or nucleic acid sequence. Custom gRNA generators and algorithms are available commercially for use in the design of effective guide RNAs. Gene editing has also been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing). Chemically modified sgRNAs have also been demonstrated to be effective in genome editing; see, for example, Hendel et al. (2015) Nature Biotechnol., 985-991.

Whereas wild-type Cas9 generates double-strand breaks (DSBs) at specific DNA sequences targeted by a gRNA, a number of CRISPR endonucleases having modified functionalities are available, for example: a "nickase" version of Cas9 generates only a single-strand break; a catalytically inactive Cas9 ("dCas9") does not cut the target DNA but interferes with transcription by steric hindrance. dCas9 can further be fused with a heterologous effector to repress (CRISPRi) or activate (CRISPRa) expression of a target gene. In some embodiments, for example, Cas9 can be fused to a transcriptional repressor (e.g., a KRAB domain) or a transcriptional activator (e.g., a dCas9-VP64 fusion). A catalytically inactive Cas9 (dCas9) fused to FokI nuclease ("dCas9-FokI") can be used to generate DSBs at target sequences homologous to two gRNAs. See, e.g., the numerous CRISPR/Cas9 plasmids disclosed in and publicly available from the Addgene repository (Addgene, 75 Sidney St., Suite 550A, Cambridge, MA 02139; addgene.org/crispr/). A "double nickase" Cas9 that introduces two separate double-strand breaks, each directed by a separate guide RNA, is described as achieving more accurate genome editing by Ran et al. (2013) Cell, 154:1380-1389.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1.

In some embodiments, a desired genome modification involves homologous recombination, wherein one or more double-stranded DNA breaks in a target nucleotide sequence is generated by an RNA-guided nuclease and guide RNA(s), followed by repair of a break(s) using a homologous recombination mechanism ("homology-directed repair"). In such embodiments, a donor template that encodes a desired nucleotide sequence to be inserted or knocked-in at a double-stranded break is administered to a cell or subject; examples of suitable templates include single-stranded DNA templates and double-stranded DNA templates (e.g., linked to the polypeptide described herein). In general, a donor template encoding a nucleotide change over a region of less than about 50 nucleotides may be administered in a format comprising single-stranded DNA; larger donor templates (e.g., more than 100 nucleotides) are often administered in a format comprising double-stranded DNA plasmids. In some embodiments, a donor template is administered to a cell or subject in a quantity that is sufficient to achieve a desired homology-directed repair but that does not persist in a cell or subject after a given period of time (e.g., after one or more cell division cycles). In some embodiments, a donor template has a core nucleotide sequence that differs from a target nucleotide sequence (e.g., a homologous endogenous genomic region) by at least 1, at least 5, at least 10, at least 20, at least 30, at least 40, at least 50, or more nucleotides. This core sequence is flanked by "homology arms" or regions of high sequence identity with the targeted nucleotide sequence; in embodiments, the regions of high identity include at least 10, at least 50, at least 100, at least 150, at least 200, at least 300, at least 400, at least 500, at least 600, at least 750, or at least 1000 nucleotides on each side of the core sequence. In some embodiments where a donor template is in the form of a single-stranded DNA, the core sequence is flanked by homology arms including at least 10, at least 20, at least 30, at least 40, at least 50, at least 60, at least 70, at least 80, or at least 100 nucleotides on each side of a core sequence. In embodiments where a donor template is in the form of a double-stranded DNA, the core sequence is flanked by homology arms including at least 500, at least 600, at least 700, at least 800, at least 900, or at least 1000 nucleotides on each side of a core sequence. In some embodiments, two separate double-strand breaks are introduced into a cell or subject's target nucleotide sequence with a "double nickase" Cas9 (see Ran et al. (2013) Cell, 154: 1380-1389), followed by delivery of a donor template.

In some embodiments, a composition comprises a polypeptide described herein linked to a gRNA and a targeted nuclease, e.g., a Cas9, e.g., a wild type Cas9, a nickase Cas9 (e.g., Cas9 D10A), a dead Cas9 (dCas9), eSpCas9, Cpf1, C2C1, or C2C3, or a nucleic acid encoding such a nuclease. A choice of nuclease and gRNA(s) is determined by whether a targeted mutation is a deletion, substitution, or addition of nucleotides, e.g., a deletion, substitution, or addition of nucleotides to a targeted sequence. Fusions of a catalytically inactive endonuclease e.g., a dead Cas9 (dCas9, e.g., D10A; H840A) tethered with all or a portion of (e.g., biologically active portion of) an (one or more) effector domain create chimeric proteins that can be linked to the polypeptide to guide a composition to specific DNA sites by one or more RNA sequences (sgRNA) to modulate activity and/or expression of one or more target nucleic acids sequences (e.g., to methylate or demethylate a DNA sequence).

As used herein, a "biologically active portion of an effector domain" is a portion that maintains the function (e.g. completely, partially, minimally) of an effector domain (e.g., a "minimal" or "core" domain). In some embodiments, fusion of a dCas9 with all or a portion of one or more effector domains of an epigenetic modifying agent (such as a DNA methylase or demethylase) creates a chimeric protein that is linked to the polypeptide and useful in methods described herein. In some embodiments, all or a portion of one or more methyltransferase or demethylase effector domains are fused with an inactive nuclease, e.g., dCas9, and linked to the polypeptide. Exemplary dCas9 fusion methods and compositions that are adaptable to methods and compositions described herein are known and are described, e.g., in Kearns et al., Functional annotation of native enhancers with a Cas9-histone demethylase fusion. Nature Methods 12, 401-403 (2015); and McDonald et al., Reprogrammable CRISPR/Cas9-based system for inducing site-specific DNA methylation. Biology Open 2016: doi: 10.1242/bio.019067.

In other aspects, 1, 2, 3, 4, 5, 6, 7, 8, 9, 10, 11, 12, 13, 14, 15, 16, 17, 18, 19, 20, or more methyltransferase or demethylase effector domains (all or a biologically active portion) are fused with dCas9 and linked to the polypeptide. The chimeric proteins described herein may also comprise a linker as described herein, e.g., an amino acid linker.

In some aspects, a linker comprises 2 or more amino acids, e.g., one or more GS sequences. In some aspects, fusion of Cas9 (e.g., dCas9) with two or more effector domains (e.g., of a DNA methylkase or demethylase) comprises one or more interspersed linkers (e.g., GS linkers) between the domains and is linked to the polypeptide.

In some aspects, dCas9 is fused with a plurality (e.g., 2-5, e.g., 2, 3, 4, 5) effector domains with interspersed linkers and is linked to the polypeptide.

In embodiments, a heterologous moiety is one or more component of a CRISPR system described hereinabove. In embodiments, methods described herein include a method of delivering one or more CRISPR system component described hereinabove to a subject, e.g., to the nucleus of a cell or tissue of a subject, by linking such component to a polypeptide described herein.

Nucleic Acids

A heterologous moiety may be a nucleic acid. A nucleic acid heterologous moiety may include, but is not limited to, DNA, RNA, and artificial nucleic acids. A nucleic acid may include, but is not limited to, genomic DNA, cDNA, tRNA, mRNA, rRNA, modified RNA, miRNA, gRNA, and siRNA or other RNAi molecule. In some embodiments, the nucleic acid is an siRNA to target a gene expression product. In some embodiments, the nucleic acid includes one or more nucleoside analogs as described herein.

Nucleic acids have a length from about 2 to about 5000 nts, about 10 to about 100 nts, about 50 to about 150 nts, about 100 to about 200 nts, about 150 to about 250 nts, about 200 to about 300 nts, about 250 to about 350 nts, about 300 to about 500 nts, about 10 to about 1000 nts, about 50 to about 1000 nts, about 100 to about 1000 nts, about 1000 to about 2000 nts, about 2000 to about 3000 nts, about 3000 to about 4000 nts, about 4000 to about 5000 nts, or any range therebetween.

Some examples of nucleic acids include, but are not limited to, a nucleic acid that hybridizes to an endogenous gene, nucleic acid that hybridizes to an exogenous nucleic acid such as a viral DNA or RNA, nucleic acid that hybridizes to an RNA, nucleic acid that interferes with gene transcription, nucleic acid that interferes with RNA translation, nucleic acid that stabilizes RNA or destabilizes RNA such as through targeting for degradation, nucleic acid that interferes with a DNA or RNA binding factor through interference of its expression or its function, nucleic acid that is linked to a intracellular protein and modulates its function, and nucleic acid that is linked to an intracellular protein complex and modulates its function.

The present disclosure contemplates the use of RNA therapeutics (e.g., modified RNAs) as heterologous moieties useful in compositions described herein. In some embodiments, for example, a modified mRNA encoding a protein of interest may be linked to a polypeptide described herein and expressed in vivo in a subject.

In some embodiments, a modified RNA linked to a polypeptide described herein, has modified nucleosides or nucleotides. Such modifications are known and are described, e.g., in WO 2012/019168. Additional modifications are described, e.g., in WO2015038892; WO2015038892; WO2015089511; WO2015196130; WO2015196118 and WO2015196128A2.

In some embodiments, a modified RNA linked to the polypeptide described herein has one or more terminal modifications, e.g., a 5'Cap structure and/or a poly-A tail (e.g., of between 100-200 nucleotides in length). The 5' cap structure may be selected from the group consisting of Cap0, Cap1, ARCA, inosine, N1-methyl-guanosine, 2'fluoro-guanosine, 7-deaza-guanosine, 8-oxo-guanosine, 2-amino-guanosine, LNA-guanosine, and 2-azido-guanosine. In some cases, the modified RNAs also contains a 5' UTR comprising at least one Kozak sequence, and a 3' UTR. Such modifications are known and are described, e.g., in WO2012135805 and WO2013052523. Additional terminal modifications are described, e.g., in WO2014164253, WO2016011306, WO2012045075, and WO2014093924.

Chimeric enzymes for synthesizing capped RNA molecules (e.g., modified mRNA) which may include at least one chemical modification are described in WO2014028429.

In some embodiments, a modified mRNA may be cyclized, or concatemerized, to generate a translation competent molecule to assist interactions between poly-A binding proteins and 5'-end binding proteins. A mechanism of cyclization or concatemerization may occur through at least 3 different routes: 1) chemical, 2) enzymatic, and 3) ribozyme catalyzed. A newly formed 5'-/3'-linkage may be intramolecular or intermolecular. Such modifications are described, e.g., in WO2013151736.

Methods of making and purifying modified RNAs are known and disclosed in the art. In some embodiments, for example, modified RNAs are made using only in vitro transcription (IVT) enzymatic synthesis. Methods of making IVT polynucleotides are known in the art and are described in WO2013151666, WO2013151668, WO2013151663, WO2013151669, WO2013151670, WO2013151664, WO2013151665, WO2013151671, WO2013151672, WO2013151667 and WO2013151736. Methods of purification include purifying an RNA transcript comprising a polyA tail by contacting the sample with a surface linked to a plurality of thymidines or derivatives thereof and/or a plurality of uracils or derivatives thereof (polyT/U) under conditions such that the RNA transcript binds to the surface and eluting the purified RNA transcript from the surface (WO2014152031); using ion (e.g., anion) exchange chromatography that allows for separation of longer RNAs up to 10,000 nucleotides in length via a scalable method (WO2014144767); and subjecting a modified RMNA sample to DNAse treatment (WO2014152030).

Modified RNAs encoding proteins in fields of human disease, antibodies, viruses, and a variety of in vivo settings are known and are disclosed in for example, Table 6 of International Publication Nos. WO2013151666, WO2013151668, WO2013151663, WO2013151669, WO2013151670, WO2013151664, WO2013151665, WO2013151736; Tables 6 and 7 International Publication No. WO2013151672; Tables 6, 178 and 179 of International Publication No. WO2013151671; Tables 6, 185 and 186 of International Publication No WO2013151667. Any of the foregoing may be synthesized as an IVT polynucleotide, chimeric polynucleotide or a circular polynucleotide and linked to the polypeptide described herein, and each may comprise one or more modified nucleotides or terminal modifications.

Nanoparticles

A heterologous moiety may be a nanoparticle. Nanoparticles may be or comprise inorganic materials with a size between about 1 and about 1000 nanometers, 1 and about 500 nanometers in size, between about 50 nm and about 300 nm, between about 75 nm and about 200 nm, between about 100 nm and about 200 nm, and any range therebetween. In some embodiments, nanoparticles may have or comprise a composite structure of nanoscale dimensions. In some embodiments, nanoparticles are typically spherical although different morphologies are possible depending on the nanoparticle composition. A portion of A nanoparticle contacting an environment external to the nanoparticle is generally identified as the surface of the nanoparticle. In some embodiments, nanoparticles as described herein have or comprise a size limitation that maybe restricted to two dimensions and so that nanoparticles include composite structure having a diameter from about 1 to about 1000 nm, where a specific diameter depends on the nanoparticle composition and on an intended use of a nanoparticle according to the experimental design. In some embodiments, for example, nanoparticles used in therapeutic applications typically have a size of about 200 nm or below.

Additional desirable properties of the nanoparticle, such as surface charges and steric stabilization, can also vary in view of the specific application of interest. In some embodiments, exemplary properties that may be desirable in clinical applications such as cancer treatment are described in Davis et al, Nature 2008 vol. 7, pages 771-782; Duncan, Nature 2006 vol. 6, pages 688-701; and Allen, Nature 2002 vol. 2 pages 750-763, each incorporated herein by reference in its entirety. In some embodiments, additional properties are identifiable by a skilled person upon reading of the present disclosure. Nanoparticle dimensions and properties can be detected by techniques known in the art. In some embodiments, exemplary techniques to detect particles dimensions include but are not limited to dynamic light scattering (DLS) and a variety of microscopies such at transmission electron microscopy (TEM) and atomic force microscopy (AFM). In some embodiments, exemplary techniques to detect particle morphology include but are not limited to TEM and AFM. In some embodiments, exemplary techniques to detect surface charges of the nanoparticle include but are not limited to zeta potential method. In some embodiments, additional techniques suitable to detect other chemical properties comprise by $^1$H, $^{11}$B, and $^{13}$C and $^{19}$F NMR, UV/Vis and infrared/Raman spectroscopies and fluorescence spectroscopy (when nanoparticle is used in combination with fluorescent labels) and additional techniques identifiable by a skilled person.

Oligonucleotide Aptamers

A heterologous moiety may be an oligonucleotide aptamer. In some embodiments, aptamer moieties may be or comprise oligonucleotide or peptide aptamers. In some embodiments, oligonucleotide aptamers are single-stranded DNA or RNA (ssDNA or ssRNA) molecules that can bind to pre-selected targets including proteins and peptides with high affinity and specificity.

In some embodiments, oligonucleotide aptamers are nucleic acid species that may be engineered through repeated rounds of in vitro selection or equivalently, SELEX (systematic evolution of ligands by exponential enrichment) to bind to various molecular targets such as small molecules, proteins, nucleic acids, and even cells, tissues and organisms. In some embodiments, aptamers provide discriminate molecular recognition, and can be produced by chemical synthesis. In some embodiments, aptamers possess desirable storage properties, and elicit little or no immunogenicity in therapeutic applications.

In some embodiments, both DNA and RNA aptamers show robust binding affinities for various targets. In some embodiments, for example, DNA and RNA aptamers have been selected for lysozyme, thrombin, human immunodeficiency virus trans-acting responsive element (HIV TAR), available on the world wide web at en.wikipedia.org/wiki/Aptamer-cite_note-10 hemin, interferon γ, vascular endothelial growth factor (VEGF), prostate specific antigen (PSA), dopamine, and the non-classical oncogene, heat shock factor 1 (HSF1).

In some embodiments, diagnostic techniques for aptamer based plasma protein profiling may be or comprise aptamer plasma proteomics. This technology will enable future multi-biomarker protein measurements that can aid diagnostic distinction of disease versus healthy states.

Peptide Aptamers

A heterologous moiety may be a peptide aptamer. In some embodiments, peptide aptamers have one (or more) short variable peptide domains, including peptides having low molecular weight, 12-14 kDa. In some embodiments, peptide aptamers may be designed to specifically bind to and interfere with protein-protein interactions inside cells.

In some embodiments, peptide e aptamers are artificial proteins selected or engineered to bind specific target molecules. In some embodiments, these proteins include of one or more peptide loops of variable sequence. In some embodiments, they are typically isolated from combinatorial libraries and often subsequently improved by directed mutation or rounds of variable region mutagenesis and selection. In some embodiments, In vivo, peptide aptamers can bind cellular protein targets and exert biological effects, including interference with the normal protein interactions of their targeted molecules with other proteins. In some embodiments, for example, a variable peptide aptamer loop attached to a transcription factor binding domain is screened against the target protein attached to a transcription factor activating domain. In some embodiments, in vivo binding of the peptide aptamer to its target via this selection strategy is detected as expression of a downstream yeast marker gene. Such experiments identify particular proteins bound by the aptamers, and protein interactions that the aptamers disrupt, to cause the phenotype. In some embodiments, peptide aptamers derivatized with appropriate functional moieties can cause specific post-translational modification of their target proteins, or change the subcellular localization of the targets In some embodiments, peptide aptamers can also recognize targets in vitro. In some embodiments, peptide aptamers have found use in lieu of antibodies in biosensors and used to detect active isoforms of proteins from populations containing both inactive and active protein forms. In some embodiments, derivatives known as tadpoles, in which peptide aptamer "heads" are covalently linked to unique sequence double-stranded DNA "tails", allow quantification of scarce target molecules in mixtures by PCR (using, for example, the quantitative real-time polymerase chain reaction) of their DNA tails.

In some embodiments, peptide aptamer selection can be made using different systems, but the most used is currently the yeast two-hybrid system. Peptide aptamers can also be selected from combinatorial peptide libraries constructed by phage display and other surface display technologies such as mRNA display, ribosome display, bacterial display and yeast display. These experimental procedures are also known as biopannings. Among peptides obtained from biopannings, mimotopes can be considered as a kind of peptide aptamers. All the peptides panned from combinatorial peptide libraries have been stored in a special database with the name MimoDB.

Pharmacoagents

In some embodiments, the heterologous moiety is an agent with an undesirable pharmacokinetic or pharmacodynamics (PK/PD) parameter. Linking the heterologous moiety to the polypeptide may improve at least one PK/PD parameter, such as targeting, absorption, and transport of the heterologous moiety, or reduce at least one undesirable PK/PD parameter, such as diffusion to off-target sites, and toxic metabolism. For example, linking a polypeptide as described herein to an agent with poor targeting/transport, e.g., doxorubicin, beta-lactams such as penicillin, improves its specificity. In some embodiments, linking a polypeptide as described herein to an agent with poor absorption properties, e.g., insulin, human growth hormone, improves its minimum dosage. In some embodiments, linking a polypeptide as described herein to an agent that has toxic metabolic properties, e.g., acetaminophen at higher doses, improves its maximum dosage.

Linkers

In some embodiments, provided compositions may comprise a linker. In some embodiments, one or more polypeptides described herein are linked with a linker. In some embodiments, a polypeptide described herein is linked to a heterologous moiety with a linker. As described herein, in some embodiments, a linker may be present at the C-terminus of a polypeptide (e.g., of the polypeptide component of a composition as described herein and/or of a polypeptide payload); alternatively or additionally, in some embodiments, a linker may be present at an N-terminus of a polypeptide and/or to a side chain or other backbone moiety of a polypeptide.

A linker may be a chemical bond, e.g., one or more covalent bonds or non-covalent bonds. In some embodiments, a linker is or comprises a peptide linker (e.g., a non ABX"C peptide); in some such embodiments, a peptide linker may be between 2-30 amino acids, or longer.

Those skilled in the art, reading the present disclosure, will appreciate that a linker, in general, may be or comprise flexible, rigid or cleavable linkers. That is, in some embodiments or instances, a linker may be a flexible linker. In some embodiments or instances, a linker may be a rigid linker. In some embodiments or instances, a linker may be a cleavable linker.

The most commonly used flexible linkers have sequences consisting primarily of stretches of Gly and Ser residues ("GS" linker). Flexible linkers may be useful for joining domains that require a certain degree of movement or interaction and may include small, non-polar (e.g. Gly) or polar (e.g. Ser or Thr) amino acids. Incorporation of Ser or Thr can also maintain the stability of the linker in aqueous solutions by forming hydrogen bonds with the water molecules, and therefore reduce unfavorable interactions between the linker and the protein moieties.

Rigid linkers are useful to keep a fixed distance between domains and to maintain their independent functions. Rigid linkers may also be useful when a spatial separation of the domains is critical to preserve the stability or bioactivity of one or more components in the fusion. Rigid linkers may have an alpha helix-structure or Pro-rich sequence, $(XP)_n$, with X designating any amino acid, preferably Ala, Lys, or Glu.

Cleavable linkers may release free functional domains in vivo. In some embodiments, linkers may be cleaved under specific conditions, such as the presence of reducing reagents or proteases. In vivo cleavable linkers may utilize the reversible nature of a disulfide bond. One example includes a thrombin-sensitive sequence (e.g., PRS) between the two Cys residues. In vitro thrombin treatment of CPRSC results in the cleavage of the thrombin-sensitive sequence, while the reversible disulfide linkage remains intact. Such linkers are known and described, e.g., in Chen et al. 2013. Fusion Protein Linkers: Property, Design and Functionality. Adv Drug Deliv Rev. 65(10): 1357-1369. In vivo cleavage of linkers in fusions may also be carried out by proteases that are expressed in vivo under pathological conditions (e.g. cancer or inflammation), in specific cells or tissues, or constrained within certain cellular compartments. The specificity of many proteases offers slower cleavage of the linker in constrained compartments.

Examples of linking molecules include a hydrophobic linker, such as a negatively charged sulfonate group; lipids, such as a poly ($-CH_2-$) hydrocarbon chains, such as polyethylene glycol (PEG) group, unsaturated variants thereof, hydroxylated variants thereof, amidated or otherwise N-containing variants thereof, noncarbon linkers; carbohydrate linkers; phosphodiester linkers, or other molecule capable of covalently linking two or more polypeptides. Non-covalent linkers are also included, such as hydrophobic lipid globules to which the polypeptide is linked, for example through a hydrophobic region of the polypeptide or a hydrophobic extension of the polypeptide, such as a series of residues rich in leucine, isoleucine, valine, or perhaps also alanine, phenylalanine, or even tyrosine, methionine, glycine or other hydrophobic residue. The polypeptide may be linked using charge-based chemistry, such that a positively charged moiety of the polypeptide is linked to a negative charge of another polypeptide or nucleic acid.

Polypeptide Linked Heterologous Moiety

Compositions may include the heterologous moiety linked to the polypeptide, such as through covalent bonds or non-covalent bonds or a linker as described herein. In some embodiments, a composition comprises a heterologous moiety linked to the polypeptide through a peptide bond. That is, in some embodiments, a linker is or comprises a peptide bond. In some embodiments, for example, in some embodiments the amino terminal of a provided polypeptide may be linked to a heterologous moiety, such as through a peptide bond, optionally further including additional linker moiety(ies). Alternatively or additionally, in some embodiments, the carboxyl terminal of the polypeptide may be linked to a heterologous moiety.

In some embodiments, a composition comprises a polypeptide linked to two heterologous moieties. In some embodiments, for example, an amino terminal and a carboxyl terminal of a provided polypeptide are linked to heterologous moieties, which may be the same or different heterologous moieties. Some embodiments, a therapeutic, such as doxorubicin, is linked to the polypeptide, and a targeting molecule, such as a ligand for a receptor present only on target cancer tissues, is also linked to the polypeptide. Upon administration, the ligand targets a composition to a cancer tissue and doxorubicin acts to inhibit cell proliferation.

In some embodiments, one or more amino acids of the polypeptide are linked with the heterologous moiety, such as through disulfide bonds between cysteine side chains, hydrogen bonding, or any other known chemistry. One heterologous moiety may be an effector with biological activity and the other heterologous moiety may be a ligand or antibody to target a composition to a specific cell expressing the receptor. In some embodiments, for example, a chemotherapeutic agent, such as topotecan a topoisomerase inhibitor, is linked to one end of the polypeptide and a ligand or antibody is linked to the other end of the polypeptide to target a composition to a specific cell or tissue. In some embodiments, the heterologous moieties are both effectors with biological activity.

In some embodiments, a plurality of polypeptides, either the same or different polypeptides, are linked to a single heterologous moiety. Provided polypeptides may act as a coating that surrounds a large heterologous moiety and aids in its membrane penetration.

The heterologous moiety may have a molecular weight greater than about 500 grams per mole (wherein those skilled in the art will understand that the unit "daltons" may be used interchangeably with "grams per mole" herein), e.g., organic or inorganic compound has a molecular weight greater than about 1,000 grams per mole, e.g., organic or inorganic compound has a molecular weight greater than about 2,000 grams per mole, e.g., organic or inorganic compound has a molecular weight greater than about 3,000 grams per mole, e.g., organic or inorganic compound has a molecular weight greater than about 4,000 grams per mole, e.g., organic or inorganic compound has a molecular weight greater than about 5,000 grams per mole, and salts, esters, and other pharmaceutically acceptable forms of such compounds are included.

In some embodiments, a composition comprises a polypeptide linked to a heterologous moiety on one or both ends and another heterologous moiety linked to another site on the polypeptide. In some such embodiments, one or both the amino terminal and the carboxyl terminal of the polypeptide is linked to a heterologous moiety; alternatively or additionally, one or more non-terminal moieties (e.g., amino acid units, for example via linkage to an amino acid side chain and/or to any other appropriate moiety in or on the polypeptide, or elsewhere in the composition) may be linked to one or more heterologous moieties. In some embodiments, one or more such linkages is through disulfide bonds or hydrogen bonding. In some embodiments, ubiquitin and another heterologous moiety, such as an effector, are linked to the polypeptide. Upon administration, a composition penetrates the cell membrane and the effector performs a function. Then, ubiquitin targets a composition for degradation.

In some embodiments, a composition comprises a polypeptide described herein linked to two heterologous moieties. In some embodiments, for example, a protein synthesis inhibitor is covalently linked to the polypeptide, and an siRNA or other target specific nucleic acid is linked to the polypeptide. Upon administration, the siRNA targets a composition to an mRNA transcript and a protein synthesis inhibitor and siRNA act to inhibit expression of an mRNA.

The polypeptides described herein can be linked to a heterologous moiety by employing standard ligation techniques, such as those described herein to link polypeptides.

In some embodiments, a composition comprises a polypeptide linked to one or more heterologous moieties through covalent bonds and another heterologous moiety linked to nucleic acids in the polypeptide. In some embodiments, for example, a protein synthesis inhibitor is covalently linked to the polypeptide, and an siRNA or other target specific nucleic acid is hybridized to nucleic acids in the polypeptide. Upon administration, an siRNA targets a composition to an mRNA transcript and a protein synthesis inhibitor and siRNA act to inhibit expression of an mRNA.

Polypeptides described herein can be linked to a heterologous moiety by employing standard ligation techniques. In some embodiments, for example, methods include, general native chemical ligation strategies (Siman, P. and Brik, A. Org. Biomol. Chem. 2012, 10:5684-5697; Kent, S. B. H. Chem. Soc. Rev. 2009, 38:338-351; and Hackenberger, C. P. R. and Schwarzer, D. Angew. Chem., Int. Ed. 2008, 47:10030-10074), click modification protocols (Tasdelen, M. A.; Yagci, Y. Angew. Chem., Int. Ed. 2013, 52:5930-5938; Palomo, J. M. Org. Biomol. Chem. 2012, 10:9309-9318; Eldijk, M. B.; van Hest, J. C. M. Angew. Chem., Int. Ed. 2011, 50:8806-8827; and Lallana, E.; Riguera, R.; Fernandez-Megia, E. Angew. Chem., Int. Ed. 2011, 50:8794-8804), and bioorthogonal reactions (King, M.; Wagner, A. Bioconjugate Chem. 2014, 25:825-839; Lang, K.; Chin, J. W. Chem. Rev. 2014, 114:4764-4806; Patterson, D. M.; Nazarova, L. A.; Prescher, J. A. ACS Chem. Biol. 2014, 9:592-605; Lang, K.; Chin, J. W. ACS Chem. Biol. 2014, 9:16-20; Takaoka, Y.; Ojida, A.; Hamachi, I. Angew. Chem., Int. Ed. 2013, 52:4088-4106; Debets, M. F.; van Hest, J. C. M.; Rutjes, F. P. J. T. Org. Biomol. Chem. 2013, 11:6439-6455; and Ramil, C. P.; Lin, Q. Chem. Commun. 2013, 49:11007-11022).

In some embodiments, introducing small mutations or a single-point mutation, a homologous recombination (HR) template may be linked to the polypeptide. In some embodiments, an HR template is a single stranded DNA (ssDNA) oligo or a plasmid. For ssDNA oligo design, in some embodiments, one may use around 100-150 bp total homology with the mutation introduced roughly in the middle, giving 50-75 bp homology arms.

Those skilled in the art, reading the present disclosure, will appreciate that, in various embodiments, any of the linkers described herein may be included to covalently or noncovalently link the polypeptide and the heterologous moiety. In some embodiments, a linker can be used, e.g., to space the polypeptide from the heterologous moiety. In some embodiments, for example, a linker can be positioned between the polypeptide and the heterologous moiety, e.g., to provide molecular flexibility of secondary and tertiary structures. In some embodiments, a linker includes at least one glycine, alanine, and/or serine amino acids to provide for flexibility. In some embodiments, a linker is a hydrophobic linker, such as including a negatively charged sulfonate group, polyethylene glycol (PEG) group, or pyrophosphate diester group. In some embodiments, a linker is cleavable to selectively release the heterologous moiety from the polypeptide, but sufficiently stable to prevent premature cleavage.

In some embodiments, a linker is used to connect a peptide of the present disclosure with an SNA.

In some embodiments, a peptide of the present disclosure may be connected to an SNA via a thioester bond.

In some embodiments, a peptide of the present disclosure is connected to an SNA of the present disclosure by a bond that includes one or more glycine residues. In some embodiments, presence of one or more glycine residues increases flexibility of the connection between the peptide and SNA.

Linkage After Administration

In some embodiments, polypeptides described herein (e.g., a plurality of linked polypeptides) have capacity to form linkages, e.g., after administration, to other polypeptides, to a heterologous moiety as described herein, e.g., an effector molecule, e.g., a nucleic acid, protein, peptide or other molecule, or other agents, e.g., intracellular molecules, such as through covalent bonds or non-covalent bonds. In some embodiments, one or more amino acids on the polypeptide are capable of linking with a nucleic acid, such as through arginine forming a pseudo-pairing with guanosine or an internucleotide phosphate linkage or an interpolymeric linkage. In some embodiments, a nucleic acid is a DNA such as genomic DNA, RNA such as tRNA or mRNA molecule. In some embodiments, one or more amino acids on the polypeptide are capable of linking with a protein or peptide.

Methods of Use

The present disclosure also includes methods of delivering a composition described herein to a subject. In embodiments, a composition is delivered across a cellular membrane, e.g., a plasma membrane, a nuclear membrane, an organellar membrane. Current polymeric delivery technologies increase endocytic rates in certain cell types, usually cells that preferentially utilize endocytosis, such as macrophages and cancer cells that rely on calcium influx to trigger endocytosis. Although not bound by any particular theory, the polypeptide described herein is believed to aid movement of a composition across membranes typically inaccessible by most agents.

In some embodiments, methods described herein comprise delivering a composition at doses sufficient to increase penetration of the heterologous moiety across a membrane described herein into cells with low endocytic rates. In some embodiments, methods described herein do not significantly increase endocytosis in a target cell. In some embodiments, delivering a composition described herein at doses sufficient to increase penetration of the heterologous moiety across a membrane does not significantly increase endocytosis, e.g., exhibits an increase of less than about 50%, 40%, 20%, 15%, 10%, 5%, 4%, 3%, 2%, 1%, or any percentage therebetween of endocytosis as compared to delivery of the heterologous moiety alone.

In some embodiments, methods described herein do not significantly increase calcium influx. In some embodiments, methods comprise delivering a composition described herein at doses sufficient to increase penetration of the heterologous moiety across a membrane does not significantly increase calcium influx, e.g., an increase of no more than about 50%, 40%, 20%, 15%, 10%, 5%, 4%, 3%, 2%, 1%, or any percentage therebetween of calcium influx as compared to delivery of the heterologous moiety alone. In some embodiments, provided methods comprise delivering a composition described herein at doses sufficient to increase penetration of the heterologous moiety across a membrane with less compartmentalized calcium movement, e.g., less than about 50%, 40%, 20%, 15%, 10%, 5%, 4%, 3%, 2%, 1%, or any percentage therebetween of compartmentalized calcium movement as compared to delivery of the heterologous moiety alone.

In some embodiments, methods described herein deliver a composition described herein across a membrane independent of endosomes. In some embodiments, delivering a composition described herein at doses sufficient to increase penetration of the heterologous moiety across a membrane does not significantly increase endosomal activity, e.g., an increase of less than 50%, 40%, 20%, 15%, 10%, 5%, 4%, 3%, 2%, 1%, or any percentage therebetween of endosomal activity as compared to delivery of the heterologous moiety alone.

In some aspects, the present disclosure includes methods of delivering a composition, where a composition includes a therapeutic heterologous moiety, e.g., a drug, and a composition increases intracellular delivery of a therapeutic as compared to a therapeutic alone. In some embodiments, for example, a composition described herein can penetrate at least a blood-brain barrier, a placental membrane separating maternal and fetal blood, and/or a blood-testis barrier between Sertoli cells in seminiferous tubules and blood. When a composition of the present disclosure includes a polypeptide linked to a therapeutic agent that has poor penetrance or bioavailability, a provided composition of the present disclosure may increase penetrance or bioavailability of a therapeutic. In some embodiments, a composition comprises a polypeptide linked to a heterologous moiety that may inhibit a blood-brain barrier efflux pump, e.g., phenylalanine-arginine β-naphthylamide (PAβN), verapamil, tricyclic chemosensitizers such as, e.g. phenothiazines. Administration of a composition may aid in blood-brain barrier penetration by, e.g. selectively inhibiting blood-brain barrier efflux pumps, such as, for example, P-glycoprotein and Oat3.

In some aspects, the present disclosure provides methods of delivering a composition to a target tissue or cell, where a composition comprises a targeting heterologous moiety, e.g., a ligand (e.g. receptor ligand) that targets one or more specific tissues or cells, and a therapeutic heterologous moiety. Upon administration, a composition may increase targeted delivery of a therapeutic as compared to a therapeutic alone. When a composition of the present disclosure is used in combination with an existing therapeutic that suffers from diffusion or off-target effects, specificity of an existing therapeutic may be increased. In some embodiments, for example, a composition described herein comprises a polypeptide linked to a chemotherapeutic agent and a ligand moiety that specifically binds a receptor on cancer cells. In some embodiments, administration of a composition may increase specificity of a chemotherapeutic agent to cancer cells through, e.g. a ligand-receptor interaction.

In some embodiments, methods described herein deliver a composition described herein across a membrane independent of endosomes. In some embodiments, delivering a composition described herein at doses sufficient to increase penetration of the heterologous moiety across a membrane does not significantly increase endosomal activity, e.g., an increase of less than 50%, 40%, 20%, 15%, 10%, 5%, 4%, 3%, 2%, 1%, or any percentage therebetween of endosomal activity as compared to delivery of the heterologous moiety alone.

As will be appreciated by one of skill in the art, currently available delivery technologies may have inadvertent effects, e.g., genome wide removal of transcription factors from DNA. In some embodiments, methods described herein modulate transcription of a gene by delivering a composition described herein across a membrane without off-target, e.g., widespread or genome-wide, effects, e.g., removal of transcription factors. In some embodiments, delivering a composition described herein at doses sufficient to increase penetration of the heterologous moiety across a membrane does not significantly alter off-target transcriptional activity, e.g., an increase of less than 50%, 40%, 20%, 15%, 10%, 5%, 4%, 3%, 2%, 1%, or any percentage therebetween of transcriptional activity of one or more off-targets as compared to activity after delivery of the heterologous moiety alone.

In some aspects, the present disclosure includes methods of delivering a composition, where a composition comprises a heterologous moiety that is or comprises a therapeutic, e.g., a drug, and a composition increases intracellular delivery of a therapeutic as compared to a therapeutic alone. In some embodiments, for example, a composition described herein may penetrate at least a blood-brain barrier, a placental membrane separating maternal and fetal blood, and/or a blood-testis barrier between Sertoli cells in seminiferous tubules and blood. When a composition of the present disclosure includes a polypeptide linked to a therapeutic agent that has poor penetrance or bioavailability, a provided composition may increase penetrance or bioavailability of a therapeutic. In some embodiments, a composition includes a polypeptide linked to a heterologous moiety that is an inhibitor of a blood-brain barrier efflux pump, e.g., phenylalanine-arginine β-naphthylamide (PAβN), verapamil, tricyclic chemosensitizers such as, e.g., phenothiazines. In some embodiments, administration of a composition aids in blood-brain barrier penetration by selectively inhibiting blood-brain barrier efflux pumps, such as, e.g. P-glycoprotein and Oat3.

In some aspects, the present disclosure provides methods of delivering a composition to a target tissue or cell, where a composition includes a targeting heterologous moiety, e.g., a ligand that targets one or more specific tissues or cells and a therapeutic heterologous moiety. Upon administration, a composition (comprising a therapeutic) increases targeted delivery of a therapeutic as compared to a therapeutic alone. When a composition of the present disclosure is used in combination with an existing therapeutic that suffers from diffusion or off-target effects, specificity of a therapeutic is increased. In some embodiments, for example, a composition described herein is or comprises a polypeptide linked to a chemotherapeutic agent and a ligand moiety that specifically binds a receptor on cancer cells. In some embodiments, administration of a composition increases specificity of a chemotherapeutic agent to cancer cells through, e.g., a ligand-receptor interaction.

In some aspects, the present disclosure provides methods of intracellular delivery of a therapeutic comprising contacting a cell or tissue with a composition described herein. In some embodiments, a therapeutic is the heterologous moiety linked to the polypeptide described herein, and a composition (comprising a therapeutic) increases intracellular delivery of a therapeutic as compared to a therapeutic alone.

In some aspects, the present disclosure includes methods of inducing cell death comprising contacting a cell with a composition described herein. In some embodiments, a composition comprises a polypeptide linked to topoisomerase inhibitor such as topotecan as described herein and a nucleic acid sequence specific for a target cell, such as a viral DNA sequence or a mutation in a gene, etc. The polypeptide translocates into a nucleus of a cell and specifically binds a viral DNA sequence or a gene mutation. A topoisomerase inhibitor prevents the DNA replication machinery from repairing double strand breaks in a genome and a cell ultimately induces apoptosis. In some embodiments, a composition comprises a polypeptide linked to topoisomerase inhibitor such as topotecan as described herein and a heterologous moiety that specifically binds a necrotic cell marker, such as cyclophilin A (CypA), a cytosolic peptidyl-prolyl cis-trans isomerase released early in necrosis, etc. A provided polypeptide targets cells in early stages of necrosis by binding a necrotic cell marker and a topoisomerase inhibitor ultimately induces apoptosis to clear necrotic cells more efficiently.

In some aspects, the present disclosure provides methods of modulating a membrane protein by contacting a cell with a composition described herein. In some embodiments, a membrane protein modulator is the heterologous moiety linked to the polypeptide described herein, and contacting a composition with a cell results in membrane protein modulation.

In some aspects, the present disclosure provides methods of administering a composition described herein to a subject to modulate a membrane protein, such as, e.g. an ion channel, a cell surface receptor, a synaptic receptor. In some embodiments, a membrane protein modulator is or comprises the heterologous moiety linked to the polypeptide described herein, and administration of a composition results in membrane protein modulation.

In some aspects, the present disclosure provides methods of non-parenteral administration of a composition described herein to a subject to increase efficacy and decrease toxicity of a parenteral therapeutic. In some embodiments, a parenteral therapeutic is the heterologous moiety linked to the polypeptide described herein, and administration of a composition results in increased efficacy and decreased toxicity of a parenteral therapeutic. In some embodiments, methods comprise oral delivery of a composition. In some embodiments, a parenteral therapeutic treats a mucosal indication.

In some aspects, the present disclosure provides methods of contacting a composition described herein with a bacteria or pathogen to decrease infectious capacity, toxicity or viability of a bacteria or pathogen.

In some aspects, the present disclosure provides methods of inducing apoptosis in a cell harboring a mutation comprising providing a composition described herein. In some embodiments, polypeptides as described herein may be linked to one heterologous moiety that is or comprises a nucleic acid that specifically binds a mutation sequence in a cell and another heterologous moiety that induces apoptosis, such as, e.g., Fas, Fas ligand, neurotrophin receptor, FADD, BID, TPEN, BAM7, cisplatin, cladribine, puromycin, monensin, sulindac sulfone, triptolide, betulinic acid, bufalin, gambogic acid, apicidin, and other known agents.

Therapies

Compositions and methods described herein may be used to treat disease in human and non-human animals.

In some aspects, methods of treating a disease and/or condition comprises administering one or more provided compositions as described herein to a subject.

Bioavailability

In some embodiments, administration of provided compositions as described herein improves at least one pharmacokinetic or pharmacodynamic parameter of the heterologous moiety, such as targeting, absorption, and transport, as compared to the heterologous moiety alone, or reduces at least one toxicokinetic parameter, such as diffusion to non-target location, off-target activity, toxic metabolism, and toxic excretion, as compared to the heterologous moiety alone (e.g., by at least 5%, 10%, 20%, 25%, 30%, 40%, 50%, 60%, 70%, 80% or more). In some embodiments, administration of a composition described herein increases a therapeutic range of the heterologous moiety (e.g., by at least 5%, 10%, 20%, 25%, 30%, 40%, 50%, 60%, 70%, 80% or more). In some embodiments, administration of a composition described herein reduces the minimum effective dose, as compared to the heterologous moiety alone (e.g., by at least 5%, 10%, 20%, 25%, 30%, 40%, 50%, 60%, 70%, 80% or more). In some embodiments, administration of a composition described herein increases the maximum tolerated dose, as compared to the heterologous moiety alone (e.g., by at least 5%, 10%, 20%, 25%, 30%, 40%, 50%, 60%, 70%, 80% or more). In some embodiments, administration of a composition increases efficacy or decreases toxicity of the therapeutic, such as non-parenteral administration of a parenteral therapeutic. In some embodiments, administration of a composition described herein increases the therapeutic range of the heterologous moiety while decreasing toxicity, as compared to the heterologous moiety alone (e.g., by at least 5%, 10%, 20%, 25%, 30%, 40%, 50%, 60%, 70%, 80% or more).

Cancer Therapies

Compositions and methods described herein may be used to treat cancer. Methods described herein may also improve existing cancer therapeutics to increase bioavailability and/or reduce toxicokinetics. Cancer or neoplasm includes solid or liquid cancer and includes benign or malignant tumors, and hyperplasias, including gastrointestinal cancer (such as non-metastatic or metastatic colorectal cancer, pancreatic cancer, gastric cancer, esophageal cancer, hepatocellular cancer, cholangiocellular cancer, oral cancer, lip cancer); urogenital cancer (such as hormone sensitive or hormone refractory prostate cancer, renal cell cancer, bladder cancer, penile cancer); gynecological cancer (such as ovarian cancer, cervical cancer, endometrial cancer); lung cancer (such as small-cell lung cancer and non-small-cell lung cancer); head and neck cancer (e.g. head and neck squamous cell cancer); CNS cancer including malignant glioma, astrocytomas, retinoblastomas and brain metastases; malignant mesothelioma; non-metastatic or metastatic breast cancer (e.g. hormone refractory metastatic breast cancer); skin cancer (such as malignant melanoma, basal and squamous cell skin cancers, Merkel Cell Carcinoma, lymphoma of the skin, Kaposi Sarcoma); thyroid cancer; bone and soft tissue sarcoma; and hematologic neoplasias (such as multiple myeloma, acute myelogenous leukemia, chronic myelogenous leukemia, myelodysplastic syndrome, acute lymphoblastic leukemia, Hodgkin's lymphoma).

In some aspects, the present disclosure provides methods of treating a cancer with a pharmaceutical composition described herein. In some embodiments, for example, a heterologous moiety of a composition described herein may be an anti-neoplastic agent, chemotherapeutic agent or other anti-cancer therapeutic agent. In some embodiments, administration of a composition described herein modulates gene expression of one or more genes, such as, for example, inhibiting gene expression of an oncogene, to, e.g. treat cancer.

In some embodiments, for example, oncology indications may be targeted by use of embodiments of the present disclosure to repress oncogenes (e.g., MYC, RAS, HER1, HER2, JUN, FOS, SRC, RAF, etc.) and/or activate tumor suppressors (e.g., P16, P53, P73, PTEN, RB1, BRCA1, BRCA2, etc.).

In some embodiments, administration of a composition described herein targets a cancer cell for cell death. The polypeptide is linked to a topoisomerase inhibitor such as, e.g., topotecan and linked to a nucleic acid, such as through, e.g., hybridization to nucleic acid side chains in the polypeptide. In some embodiments a nucleic acid sequence comprises complementary sequences that specifically bind a cancer mutation. In some embodiments, upon administration, the polypeptide translocates into a nucleus to specifically bind a cancer mutation and a topotecan prevents DNA replication machinery from repairing double strand breaks in a genome. In some embodiments, a cell ultimately induces apoptosis concomitant with or after administration of a composition as described herein.

Neurological Diseases or Disorder

Methods described herein may also treat a neurological disease. A "neurological disease" or "neurological disorder" as used herein, is a disease or disorder that affects a nervous system of a subject including a disease that affects brain, spinal cord, and/or peripheral nerves. In some embodiments, a neurological disease or disorder may affect nerve cells and/or supporting cells of a nervous system, such as, e.g. glial cells. In some embodiments, causes of neurological disease or disorder comprise infection, inflammation, ischemia, injury, tumor, or inherited illness. In some embodiments, neurological diseases or disorders comprise neurodegenerative diseases and myodegenerative diseases. In some embodiments, for example, neurodegenerative diseases comprise one or more of amyotrophic lateral sclerosis, Alzheimer's disease, frontotemporal dementia, frontotemporal dementia with TDP-43, frontotemporal dementia linked to chromosome-17, Pick's disease, Parkinson's disease, Huntington's disease, Huntington's chorea, mild cognitive impairment, Lewy Body disease, multiple system atrophy, progressive supranuclear palsy, an α-synucleinopathy, a tauopathy, a pathology associated with intracellular accumulation of TDP-43, and cortico-basal degeneration in a subject. In some embodiments, for example, neurological diseases or disorders may comprise tinnitus, epilepsy, depression, stroke, multiple sclerosis, migraines, and anxiety.

As will be appreciated by those of skill in the art, many bacterial (e.g. Mycobacterial tuberculosis, *Neisseria meningitides*), viral (e.g. Human Immunodeficiency Virus (HIV), Enteroviruses, West Nile Virus, Zika), fungal (e.g. *Cryptococcus, Aspergillus*), and parasitic (e.g., malaria, Chagas) infections can affect the nervous system. In some embodiments, neurological symptoms may occur due to an infection itself, or due to an immune response.

In some aspects, the present disclosure provides methods of treating a neurological disease or disorder with a pharmaceutical composition described herein. In some embodiments, for example, a heterologous moiety of a composition described herein may be, e.g., a corticosteroid, an anti-inflammatory, a dopamine-affecting drug, or an acetylcholine inhibitor. In some embodiments, administration of a composition described herein modulates activation of, e.g., a neurotransmitter, neuropeptide, or neuroreceptor.

In some embodiments, compositions of the present disclosure may be used to modulate neuroreceptor activity (e.g., adrenergic receptor, GABA receptor, acetylcholine receptor, dopamine receptor, serotonin receptor, cannabinoid receptor, cholecystokinin receptor, oxytocin receptor, vasopressin receptor, corticotropin receptor, secretin receptor, somatostatin receptor, etc.) with a neurotransmitter, neuropeptide, agonist or antagonist thereof (e.g., acetylcholine, dopamine, norepinephrine, epinephrine, serotonin, melatonin, cirodhamine, oxytocin, vasopressin, cholecystokinin, neurophysins, neuropeptide Y, enkephalin, orexins, somatostatin, etc.).

Treatments for Acute and Chronic Infections

Methods as described herein may improve existing acute and chronic infection therapeutics to increase bioavailability and reduce toxicokinetics. As used herein, "acute infection" refers to an infection that is characterized by a rapid onset of disease or symptoms. As used herein, by "persistent infection" or "chronic infection" is meant an infection in which the infectious agent (e.g., virus, bacterium, parasite, mycoplasm, or fungus) is not cleared or eliminated from the infected host, even after the induction of an immune response. In some embodiments, persistent infections may be chronic infections, latent infections, or slow infections. As will be recognized by those of skill in the art, acute infections may be relatively brief (lasting a few days to a few weeks) and resolved by the immune system and persistent infections may last for months, years, or even a lifetime. In some embodiments, infections may also recur frequently over a long period of time, involving stages of silent and productive infection without cell killing or even producing excessive damage to host cells. As will be appreciated by those of skill in the art, mammals may be diagnosed as having a persistent infection according to any standard method known in the art as described, for example, in U.S. Pat. Nos. 6,368,832, 6,579,854, and 6,808,710.

In some embodiments, an infection may be caused by a pathogen from one of the following major categories:

i) viruses, including members of the Retroviridae family such as the lentiviruses (e.g. Human immunodeficiency virus (HIV) and deltaretroviruses (e.g., human T cell leukemia virus I (HTLV-I), human T cell leukemia virus II (HTLV-II)); Hepadnaviridae family (e.g. hepatitis B virus (HBV)), Flaviviridae family (e.g. hepatitis C virus (HCV)), Adenoviridae family (e.g. Human Adenovirus), Herpesviridae family (e.g. Human cytomegalovirus (HCMV), Epstein-Barr virus, herpes simplex virus 1 (HSV-1), herpes simplex virus 2 (HSV-2), human herpesvirus 6 (HHV-6), varicella-zoster virus), Papillomaviridae family (e.g. Human Papillomavirus (HPV)), Parvoviridae family (e.g. Parvovirus B19), Polyomaviridae family (e.g. JC virus and BK virus), Paramyxoviridae family (e.g. Measles virus), Togaviridae family (e.g. Rubella virus) as well as other viruses such as hepatitis D virus;

ii) bacteria, such as, e.g. those from the following families: *Salmonella* (e.g. *S. enterica Typhi*), *Mycobacterium* (e.g. *M. tuberculosis* and *M. leprae*), *Yersinia* (*Y. pestis*), *Neisseria* (e.g. *N. meningitides*, N. gonorrhea), *Burkholderia* (e.g. *B. pseudomallei*), *Brucella*, *Chlamydia*, *Helicobacter*, *Treponema*, *Borrelia*, *Rickettsia*, and *Pseudomonas*;

iii) parasites, such as, e.g., *Leishmania*, *Toxoplasma*, *Trypanosoma*, *Plasmodium*, *Schistosoma*, or Encephalitozoon; and iv) prions, such as, e.g. prion protein.

In some embodiments, administration of a composition described herein suppresses transcription or activates transcription of one or more genes to treat an infection such as a viral infection. In some embodiments, a polypeptide linked to an inhibitor of viral DNA transcription, e.g., nucleoside analogs such as acyclovir, valaciclovir, penciclovir, denavir, famciclovir, bromovinyldeoxiuridine, ganciclovir; product analogs such as hydroxycarbamide or pyrophosphate analogs like foscarnet, allosteric inhibitors or inhibitors that intercalate or directly interact with nucleic acids, is administered to treat the viral infection. The polypeptide may further comprise a cell targeting ligand for targeted delivery of an anti-viral therapeutic.

In some embodiments, administration of a composition described herein targets a virally infected cell for cell death. The polypeptide is linked to a topoisomerase inhibitor such as, e.g. topotecan and linked to a nucleic acid that specifically binds, e.g. a viral sequence, such as through, e.g. hybridization to nucleic acid side chains in the polypeptide. A nucleic acid sequence may include complementary sequences that specifically bind viral DNA integrated into a genome. Upon administration, the polypeptide translocates into a nucleus to specifically bind integrated viral DNA and topotecan prevents DNA replication machinery from repairing double strand breaks in the genome. In some embodiments, a cell ultimately induces apoptosis.

Treatments of Other Diseases/Disorders/Conditions

In some aspects of the present disclosure, diseases that may be treated by a composition described herein include one or more of imprinted or hemizygous mono-allelic diseases, bi-allelic diseases, autosomal recessive disorders, autosomal dominant disorders, and diseases characterized by nucleotide repeats, e.g., trinucleotide repeats in which silencing of a gene through methylation drives symptoms, can be targeted by use of the present disclosure to modulate expression of the affected gene. In some embodiments, for example, diseases that may be treated by a composition as described herein comprise: Jacobsen syndrome, cystic fibrosis, sickle cell anemia, and Tay Sachs disease, tuberous sclerosis, Marfan syndrome, neurofibromatosis, retinoblastoma, Waardenburg syndrome, familial hypercholesterolemia, DRPLA (Dentatorubropallidoluysian atrophy), HD (Huntington's disease), Beckwith-Wiedemann syndrome, Silver-Russell syndrome, SBMA (Spinal and bulbar muscular atrophy), SCA1 (Spinocerebellar ataxia Type 1), SCA2 (Spinocerebellar ataxia Type 2), SCA3 (Spinocerebellar ataxia Type 3 or Machado-Joseph disease), SCA6 (Spinocerebellar ataxia Type 6), SCA7 (Spinocerebellar ataxia Type 7), SCA17 (Spinocerebellar ataxia Type 17), FRAXA (Fragile X syndrome), FXTAS (Fragile X-associated tremor/ataxia syndrome), FRAXE (Fragile XE mental retardation), FRDA (Friedreich's ataxia) FXN or X25, DM (Myotonic dystrophy), SCA8 (Spinocerebellar ataxia Type 8), and SCA12 (Spinocerebellar ataxia Type 12).

In some aspects, the present disclosure provides methods of treating a genetic disease/disorder/condition with a pharmaceutical composition described herein. In some embodiments, administration of a provided composition described herein may modulate gene expression of one or more genes that are implicated in a genetic disease/disorder/condition, such as. for example, activating, suppressing, and/or modulating expression of a gene.

In some aspects, the present disclosure provides methods of treating a disease/disorder/condition with a pharmaceutical composition described herein. In some embodiments, administration of a composition described herein may modulate gene expression of one or more genes to treat a disease/disorder/condition, such as, for example. activating, suppressing, and/or modulating expression of a gene.

Administration and Formulation

In various embodiments, the present disclosure provides pharmaceutical compositions as described herein further comprising a pharmaceutically acceptable excipient. Pharmaceutically acceptable excipient is or comprises an excipient that is useful in preparing a pharmaceutical composition that is generally safe, non-toxic, and desirable, and includes excipients that are acceptable for veterinary use as well as for human pharmaceutical use. In some embodiments, such excipients may be solid, liquid, semisolid, or, in the case of an aerosol composition, gaseous.

In various embodiments, pharmaceutical compositions described herein may be formulated for delivery via any route of administration. In some embodiments, modes of administration include injection, infusion, instillation, or ingestion. In some embodiments, injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, administration includes aerosol inhalation, e.g., with nebulization. In some embodiments, administration may be systemic (e.g., oral, rectal, nasal, sublingual, buccal, or parenteral), enteral (e.g., system-wide effect, but delivered through the gastrointestinal tract), and/or local (e.g., local application on the skin, intravitreal injection). In some embodiments, a composition is administered systemically. In some embodiments, administration is non-parenteral and a therapeutic is a parenteral therapeutic.

Pharmaceutical compositions described herein may also be tableted or prepared in an emulsion or syrup for oral administration. Pharmaceutically acceptable solid and/or liquid carriers may be added to enhance or stabilize a composition, or to facilitate preparation of a composition. Liquid carriers may be or comprise, e.g., syrup, peanut oil, olive oil, glycerin, saline, alcohols, and/or water. Solid carriers may be or comprise, e.g. starch, lactose, calcium sulfate, dihydrate, terra alba, magnesium stearate or stearic acid, talc, pectin, acacia, agar and/or gelatin. A carrier may be or comprise a sustained release material such as, e.g., glyceryl monostearate or glyceryl distearate, alone or with a wax.

As will be appreciated by one of skill in the art, pharmaceutical preparations are made following conventional techniques of pharmacy involving milling, mixing, granulation, and compressing, when necessary, for tablet forms; or milling, mixing and filling for hard gelatin capsule forms. In some embodiments, when a liquid carrier is used, a preparation may be in a form of a syrup, elixir, emulsion or an aqueous or non-aqueous suspension. In some embodiments, a liquid formulation may be administered directly per os (e.g., orally).

Pharmaceutical compositions according to the present disclosure may be delivered in a therapeutically effective amount. A precise therapeutically effective amount is an amount of a composition that will yield most efficacy of treatment in a given subject. In some embodiments, a therapeutically effective amount may vary depending upon a variety of factors, including but not limited to characteristics of a therapeutic compound (including, e.g. activity, pharmacokinetics, pharmacodynamics, and bioavailability), physiological condition of the subject (including, e.g. age, sex, disease type and stage, general physical condition, responsiveness to a given dosage, and type of medication), nature of a pharmaceutically acceptable carrier or carriers in a formulation, and a route of administration. One skilled in the clinical and pharmacological arts will be able to determine a therapeutically effective amount through routine experimentation, for instance, by monitoring a subject's response to administration of a compound and adjusting the dosage accordingly. For additional guidance, see Remington: The Science and Practice of Pharmacy (Gennaro ed. 22.sup.nd edition, Williams & Wilkins PA, USA) (2012).

In some aspects, the present disclosure provides methods of delivering a therapeutic by administering a provided composition described herein. In some embodiments, the heterologous moiety is a therapeutic and a composition increases intracellular delivery of the therapeutic as compared to the therapeutic alone.

All references and publications cited herein are hereby incorporated by reference.

The following examples are provided to further illustrate some embodiments of the present disclosure, but are not intended to limit scope of the present disclosure; it will be understood by their exemplary nature that other procedures, methodologies, or techniques known to those skilled in the art may alternatively be used.

EXAMPLES

Example 1: Producing a Polypeptide with Solid Phase Synthesis

This example demonstrates solid phase synthesis of an exemplary polypeptide alpha.

Therapeutic design: Polypeptide: PFDILYQLLRGQGDC (SEQ ID NO:1)

Experimental design: An exemplary polypeptide alpha, as described herein, is synthesized automatically (MilliGen 9050 peptide synthesizer) by a solid-phase method using standard Fmoc (N-(9-fluorenyl)methoxycarbonyl) chemistry in a continuous flow mode.

Polypeptide purification is performed by reversed-phase high-performance liquid chromatography (RP-HPLC) with UV detection at 260 nm using a semi-prep column C18 (10 μm, 300×7.7 mm, Xterra Waters, 300 Å), eluting with water containing 0.1% TFA (eluent A) and acetonitrile containing 0.1% TFA (eluent B); elution gradient: from 100% A to 50% B in 30 min, flow: 4 ml/min. The purity and identity of the purified polypeptides are examined by ultra-performance liquid chromatography tandem mass-spectrometry (UPLC-MS; Waters Acquity equipped with ESI-Q analyzer) using an Acquity UPLC BEH C18; 2.1×50 MM, 1.7 μm column. Expected mass peaks are observed for amino acid and nucleic acid sequences corresponding to SEQ ID NO: 1.

Example 2: Ligation of Multiple Polypeptides

This example demonstrates ligating two or more exemplary polypeptide alphas through click chemistry.

Exemplary polypeptide alphas may comprise, e.g., two or more instances of the same polypeptide alpha, at least one instance of each of two distinct polypeptide alphas, etc.

Click chemistry involves rapid generation of compounds by joining small units together via heteroatom links (e.g. C-X-C). A main objective of click chemistry is to develop a set of powerful, selective, and modular blocks that are useful for small- and large-scale applications. Click reactions are bio-orthogonal, i.e. can occur within organisms without interfering with native biochemical processes. Reaction of a dibenzylcyclooctyne (DBCO) linker with an azide linker forms a stable triazole. This click reaction (between DBCO and azide) is very fast at room temperature, does not require a cytotoxic Cu(I) catalyst, and creates stable triazoles. A covalent bond is created when DBCO, incorporated into one type of biomolecule, reacts with an azide linker, incorporated into a second biomolecule. DBCO strain-promoted or Cu(I)-free [2+3] cycloaddition strategy relies on use of strained dibenzylcyclooctynes. Use of strained dibenzylcyclooctynes decreases activation energy required for a cycloaddition click reaction, allowing it to be carried out without need for catalysis at low temperatures with an efficiency greater than that of a Cu(I)-catalyzed ligation.

Therapeutic design: Polypeptide alpha with dibenzylcyclooctyne (DBCO) modification and polypeptide alpha with azide modification.

Experimental design: To prepare for a click reaction, exemplary polypeptide alphas are labeled with DBCO (Glen Research, Sterling, VA). DBCO-sulfo-NHS ester is dissolved at a concentration of 5.2 mg per 60 µL in water or anhydrous DMSO. This stock solution is used to conjugate amino-modified polypeptide alphas in sodium carbonate/bicarbonate conjugation buffer, pH=~9.

For a 0.2 µmol synthesis of DBCO-conjugated polypeptide alpha, exemplary polypeptide alphas are dissolved in 500 µL of conjugation buffer. Approx. a 6 fold excess (6 µL) of DBCO-sulfo-NHS ester solution is added to the solution of dissolved polypeptides. The mixture is vortexed and incubated at room temperature for about 2-4 hours or up to about overnight. DBCO-conjugated polypeptide alphas are desalted on a desalting column (Glen Research, Sterling, VA) to remove salts and organics.

For a 0.2 µmol synthesis of azide-conjugated polypeptide alpha, exemplary polypeptide alphas are dissolved in 500 µL of conjugation buffer. Approx. a 6 fold excess (6 µL) of azide solution is added to the solution of dissolved polypeptides. The mixture is vortexed and incubated at room temperature for about 2-4 hours or up to about overnight. Azide-conjugated polypeptide-alphas are desalted on a desalting column (Glen Research, Sterling, VA) to remove salts and organics.

To perform a click reaction, 1 mg of azide is dissolved in 150 µL of DMSO. Azide-conjugated polypeptide alpha solution is added to 10 OD of DBCO-conjugated polypeptide alphas in 100 µL of water. The mixture is incubated at room temperature overnight. Ligated polypeptides (comprised of DBCO-conjugated polypeptide alphas ligated to azide-conjugated polypeptide alphas) are desalted on a desalting column (Glen Research, Sterling, VA) to remove salts and organics.

In another click reaction, succinimidyl esters, (5/6-carboxyfluorescein succinimidyl ester and succinimidyl-2-(biotinamido)ethyl-1,3-dithiopropionate, Thermo Fisher Scientific, Waltham, USA) are dissolved in dry DMSO (Acros, Geel, Belgium). Primary amine labeling is carried out at 4° C. for 1 hour in 20 mM Na Phosphate buffer pH 7.2 containing 0.05% dodecyl maltoside.

Maleimides, dibenzylcyclooctyne-PEG4-maleimide and azido-PEG3-maleimide (Jena Bioscience), are dissolved in dry DMSO. Sulfhydryl labeling is performed at 25° C. for 2 hours in 20 mM Na Phosphate buffer pH 7.2 containing 0.05% dodecyl maltoside. Copper-free coupling by click chemistry is performed in the same buffer for 10 hours at 4° C.

After a reaction with 5/6-carboxyfluorescein succinimidyl ester and maleimides, labeled protein is separated from unreacted label using spin columns (Micro Biospin TM6 columns, Bio-Rad, Hercules, USA), according to manufacturer's instructions.

Reaction products after coupling are analyzed by HPLC. 20-40 µl samples are injected and separated on a chromatography system equipped with an analytical column (300 mm×4.60 mm) eluted with 20 mM Na Phosphate buffer pH 7.2 containing 0.05% dodecyl maltoside at a flow rate of 0.5 ml/min and followed by absorption at 280 nm. Absorption spectra of peaks are obtained from an integrated spectral detector (Agilent technologies G1315D diode array detector).

Example 3: Click Chemistry to Link a Polypeptide and a Heterologous Moiety

This example demonstrates joining one or more multimerized polypeptide alphas from Example 2 to one or more heterologous moieties through click chemistry.

Therapeutic design: Polypeptide alpha with dibenzylcyclooctyne (DBCO) modification and penicillin with azide modification.

Experimental design: To prepare for a click reaction, polypeptide alphas are labeled with DBCO (Glen Research, Sterling, VA). DBCO-sulfo-NHS ester is dissolved at a concentration of 5.2 mg per 60 µL in water or anhydrous DMSO. This stock solution is used to conjugate amino-modified polypeptides in sodium carbonate/bicarbonate conjugation buffer, pH=~9.

For a 0.2 µmol synthesis of DBCO-conjugated polypeptide alphas, polypeptide alphas are dissolved in 500 µL of conjugation buffer. Approx. a 6 fold excess (6 µL) of DBCO-sulfo-NHS ester solution is added to the solution of dissolved polypeptides. The mixture is vortexed and incubated at room temperature for about 2-4 hours or up to about overnight. DBCO-conjugated polypeptide alpha is desalted on a desalting column (Glen Research, Sterling, VA) to remove salts and organics.

Penicillin is dissolved in 500 µL of conjugation buffer. Approx. a 6 fold excess (6 µL) of azide solution is added to the solution of dissolved penicillin. The mixture is vortexed and incubated at room temperature for about 24 hours or up to about overnight. Azide-conjugated penicillin is desalted on a desalting column (Glen Research, Sterling, VA) to remove salts and organics.

To perform a click reaction, 1 mg of azide is dissolved in 150 µL of DMSO. Azide-conjugated penicillin is added to 10 OD of DBCO-conjugated polypeptide alphas in 100 µL of water. The mixture is incubated at room temperature overnight. Ligated polypeptides (comprising DBCO-conjugated polypeptide alphas ligated to azide-conjugated penicillin) are desalted on a desalting column (Glen Research, Sterling, VA) to remove salts and organics.

Example 4: Method of Treating Listeriosis

This example demonstrates in vitro efficacy of polypeptides for (systemic) intracellular delivery of β-lactams for treatment of listeriosis.

Listeriosis is a serious infection usually affecting older adults, pregnant women, newborns, and individuals with weakened immune systems. Listeriosis is caused by eating food contaminated with *Listeria* bacteria. Treatments typically include prolonged administration of antibiotics, primarily ampicillin and gentamicin, to which the bacteria are usually susceptible. β-lactam is a four-membered lactam ring that is the core structure of several antibiotic families, in particular penicillins. β-lactams are effective in solution but have poor cell penetrating properties, requiring high minimum effective doses than other treatments (e.g. other classes of antibiotics) with increased potential for toxicity. By conjugating a β-lactam to polypeptide alpha, e.g. as in Examples 1-3, one or more cell penetrating properties of β-lactam may be increased, potentially lowering minimum effective dose required for treatment and/or decreasing toxicity associated with higher doses.

Therapeutic design: An exemplary polypeptide alpha is linked to penicillin as described herein (e.g., in Example 3), for example to the amino or carboxy terminus of the polypeptide. See FIG. 1.

Experimental design: Cell type: Caco-2 cell line infected with *listeria*

Method: Semiconfluent monolayers of Caco-2 cells are inoculated with bacterial suspensions adjusted to obtain a multiplicity of infection (MOI) of 100 bacteria per cell. Penetration is allowed to proceed for 1 h at 37° C. Infected cells are then washed three times with Earle's balanced salt solution (EBSS) (GIBCO) and covered with 2 ml of DMEM containing penicillin, polypeptide conjugated penicillin at various concentrations (0, 0.5 mg/L, 1 mg/L, 5 mg/L or 10 mg/L) to kill extracellular bacteria. Cells are incubated for an additional period of 18 h, the starting point of which is defined as time zero. At various times during this 18-h period, cells are washed three times with EBSS and lysed by cold distilled water before viable intracellular bacteria are counted. Experiments are carried out in duplicate and repeated three times for each bacterial strain tested. Results are expressed as the mean log 10 viable bacteria per well. Penicillin-conjugated polypeptide alpha clears infection at 1, 5, and 10 mg/L and/or slows growth of bacteria as compared to treatment with antibiotic alone.

Example 5: Using Polypeptides for Tissue Specific Delivery of Pharmacological Agents This example demonstrates in vivo tissue targeting of polypeptides for intracellular delivery. Such delivery may reduce effective doses and side effects/adverse effects normally seen with systemic administration of a given pharmacological agent.

ADPKD (autosomal dominant polycystic kidney disease) is the fourth leading cause of renal failure. It is the most prevalent monogenic human condition. ADPKD is an autosomal dominant disease, characterized by the presence of fluid-filled cysts in the kidneys, which disrupt renal function and eventually lead to complete organ failure. There is currently no cure for ADPKD, and treatments are mostly directed at reduction of cyst number and size. CFTR (Cystic Fibrosis Transmembrane Conductance Regulator) is an ABC transporter class expressed in the cytoplasmic membrane of epithelial cells in kidneys, lungs and other tissues. CFTR is a membrane protein and an ion channel that regulates flux of chloride ions, and in this way, determines rate and amount of fluid transported across epithelial cellular membranes. Small molecule CFTR inhibitors have a beneficial effect in models of ADPKD, as they decrease the expansion rate of fluid-filled cysts. Since CFTR is expressed in cells other than renal epithelial cells, a tissue specific delivery approach could be beneficial in the reduction of effective doses and side effects caused by systemic administration.

Figure 2:
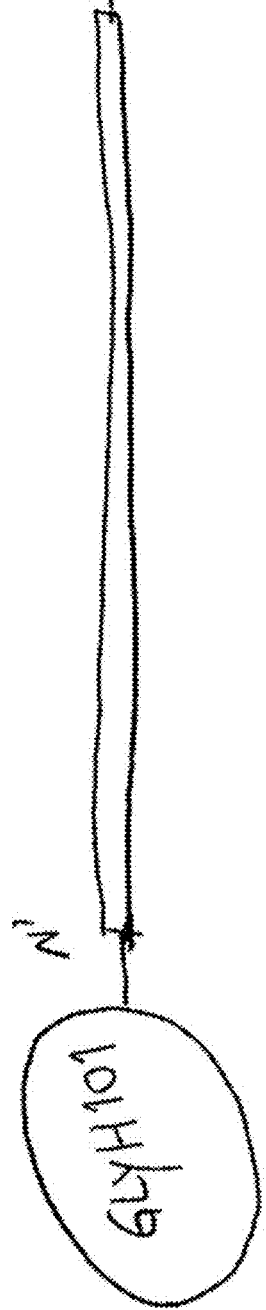
FIG. 2 is an illustration of a polypeptide alpha linked to GlyH101 and the AQP2 ligand (SEQ ID NO: 2).
Figure 3:
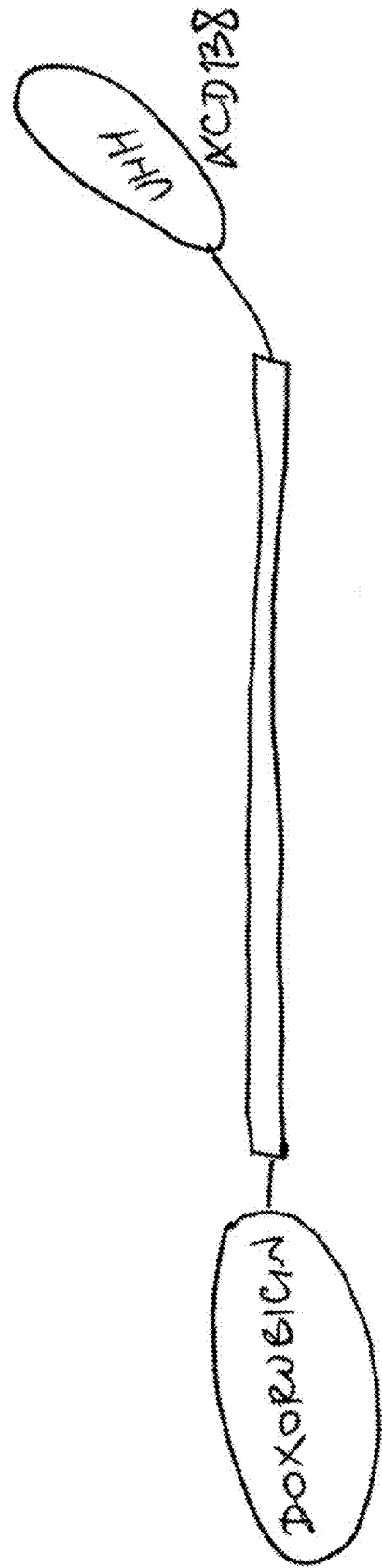
FIG. 3 is an illustration of a polypeptide alpha linked to doxorubicin and a single domain antibody (sdAb) to CD138.

Therapeutic design: Delivery of CFTR inhibitors is achieved by utilization of a provided polypeptide as produced, e.g. in Example 1 or 2, bound to effector cargo (e.g. small molecule inhibitors of thiazolidinone and glycine hydrazide classes, such as GlyH101 and tetrazolo-CFTRi$_{nh}$-172), by means of a covalent bond linking to an effector to either a carboxyl or amino terminal of a provided polypeptide. Tissue specificity is achieved by fusing, e.g. a protein that binds to another protein, for example, a ligand that binds to a transmembrane protein, which transmembrane protein is preferentially expressed in a particular cell type. In the present example, an exemplary AQP2 ligand (whose amino acid sequence is CKRVTGRPC (SEQ ID NO: 2)); hereinafter "CKRVTGRPC ligand) is fused to a free terminus of a polypeptide. See FIG. 2. AQP2 is an aquaporin transmembrane protein expressed preferentially in renal epithelium, and an exemplary peptide such as, e.g., a peptide represented by SEQ ID NO: 2, may be or comprise a ligand of AQP2. The presence of a ligand (e.g. ligand of SEQ ID NO: 2;), via fusion to a provided polypeptide, tethers a polypeptide with its effector cargo to a particular cell type, e.g. renal epithelial cells, therefore increasing tissue specific absorption of the effector cargo.

Experimental design: To test efficacy of an exemplary polypeptide (e.g. CKRVTGRPC ligand-polypeptide-effector cargo; in this example, effector cargo is or comprises an inhibitor of CFTR; hereinafter "CFTR inhibitor") molecule on cyst size in vitro, an MDCK cell model of ADPKD is used. Type I MDCK cells (ATCC No. CCL-34) are cultured at 37° C. in a humidified 95% air/5% $CO_2$ atmosphere in a 1:1 mixture of DMEM and Ham's F-12 nutrient medium supplemented with 10% FBS (Hyclone, Logan, UT), 100 U/ml penicillin, and 100 µg/ml streptomycin. For generation of cysts, 400 MDCK cells are suspended in 0.4 ml of ice-cold Minimum Essential Medium containing 2.9 mg/ml collagen (PureCol; (named Biomaterials, Fremont CA), 10 mM HEPES, 27 mM $NaHCO_3$, 100 U/ml penicillin, and 100 µg/ml streptomycin (pH 7.4). The cell suspension is then plated onto 24-well plates. After gel formation, 1.5 ml of MDCK cell medium containing 10 µM forskolin is added to each well, and plates are maintained at 37° C. in a 5% $CO_2$ humidified atmosphere.

To test CFTR inhibitors, compounds (e.g. CKRVTGRPC ligand-polypeptide-CFTR inhibitor or CFTR inhibitor alone) are included in culture medium in the continued presence of forskolin from day 0 onward. Medium containing forskolin and test compounds is changed every 12 h. At day 6, cysts (with diameters >50 µm) and noncyst cell colonies are counted by phase-contrast light microscopy at ×20 magnification (546 nm monochromatic illumination) using a Nikon TE 2000-S inverted microscope (Nikon Corporation, Tokyo, Japan). Cysts are measured every two days using micrographs showing the same cysts in collagen gels (cysts identified by markings on plates). To determine extent of cyst growth, cyst diameters are measured using Image J software. At least 10 cysts per well and three wells per group are measured for each condition.

To determine whether a provided composition, e.g. CKRVTGRPC ligand-polypeptide-CFTR inhibitor e is absorbed preferentially by kidney cells, and/or is efficacious in reducing cyst growth rate in vivo, a Pkd1$^{flox/-}$;Ksp-Cre mouse model of ADPKD is used. Compounds (e.g., CKRVTGRPC ligand-polypeptide-CFTR inhibitor or CFTR inhibitor alone) are administered subcutaneously or orally, and effective doses are determined experimentally. CFTR inhibitor compound is effective in a range of about 5 to about 10 mg/kg. CKRVTGRPC ligand-polypeptide-CFTR inhibitor may be effective at a lower dose range than a dose range of CFTR inhibitor alone.

Blood and urine samples are collected for measurement of CFTR inhibitor concentration and renal function. Kidneys are removed and weighed and fixed for histologic examination or homogenized for determination of CFTR inhibitor content.

To determine effective CFTR inhibition and preferential adsorption in kidneys, mice are sacrificed and histological sections are made from kidneys, lungs, pancreas, and colon. These tissues express CFTR but, with the exception of the kidneys, do not express AQP2. Cyst size is measured. Tissues are fixed with Bouin's fixative and embedded in paraffin. Three-micrometer-thick sections are cut serially every 200 μm and stained with hematoxylin and eosin. Sections are imaged using a Leica inverted epifluorescence microscope (DM 4000B, Wetzlar, Germany) equipped with ×2.5 objective lens and color CCD camera (Spot, model RT KE; Diagnostic Instruments, Sterling Heights, MI).

Quantification of Cyst Growth: Cyst sizes in micrographs of metanephron and kidney sections are determined using MATLAB 7.0 software (Natick, MA). A masking procedure is used to highlight all pixels of similar intensity within each cyst. Fractional cyst area is calculated as total cyst area divided by total kidney area. Cysts with diameters >50 μm are included in the analysis.

Provided compounds (e.g. a heterologous moiety (e.g. CKRVTGRPC ligand) linked to a provided polypeptide with CFTR inhibitor) localize to renal epithelial cells, therefore increasing tissue specific absorption of a provided drug (e.g. CFTR inhibitor as delivered by a composition comprising CKRVTGRPC ligand-polypeptide-CFTR inhibitor), as well as showing efficacy at a lower dose range than CFTR inhibitor alone.

Example 6: Reducing Drug Toxicity by Targeted Delivery

This example demonstrates in vivo targeted drug delivery by exemplary polypeptides to reduce concentrations of effective doses and side effects/adverse effects caused by drug administration, e.g. chemotherapy.

Doxorubicin hydrochloride is a medication used in cancer chemotherapy. It is commonly used in treatment of a wide range of cancers, including hematological malignancies such as lymphoma and leukemia. Doxorubicin intercalates between base pairs in DNA helices, thereby preventing DNA replication and ultimately inhibiting protein synthesis. Doxorubicin inhibits topoisomerase II which results in an increased and stabilized cleavable enzyme-DNA linked complex during DNA replication and subsequently prevents ligation of nucleotide strands after double-strand breakage. Doxorubicin also forms oxygen free radicals resulting in cytotoxicity secondary to lipid peroxidation of cell membrane lipids. Unfortunately, efficacy of doxorubicin and other anthracyclines in treating cancer can be limited by a cumulative dose-dependent cardiotoxicity, which can cause irreversible heart failure.

Therapeutic design: In this example, doxorubicin ($C_{27}H_{29}NO_{11}$) is linked to the carboxyl or amino terminus of a provided polypeptide as produced, e.g. in Example 1 or 2, fused to a single domain antibody against CD138 ("polypeptide alpha-anti-CD138"). See FIG. 3. This fusion polypeptide is expected to increase an amount of polypeptide (and, accordingly, doxorubicin) incorporated by CD138-expressing cells, and decrease translocation of polypeptide (and doxorubicin) into non-CD138 expressing cells.

Experimental design: This is tested in a xenograft mouse of acute myeloid leukemia ("AML"): To study influence of doxorubicin-polypeptide-anti-CD138 on outcomes of AML progression in mice, a chemotherapy regimen involving intraperitoneal (i.p.) injection of an exemplary doxorubicin-polypeptide-anti-CD138 or doxorubicin alone at 5 dose ranges (about 0.5, 1, 2, 2.5, and 3 mg/kg per day over 3 d) is used. This regimen mimics standard induction therapy used to treat AML in human patients.

Primary leukemia is transplanted into 20-30 6- to 8-wk-old sublethally irradiated recipient mice (4.5 Gy, 24 h prior to transplantation) by tail-vein injection of $1\times10^6$ viable $GFP^+$ cells (e.g. $GFP^+$ Kasumi-1 cells, $GFP^+$ KG-1 cells) per recipient. Sublethal irradiation is used to achieve a more uniform disease onset in recipient animals. Recipient mice are maintained on ciprofloxacin-supplemented drinking water (ciprofloxacin 125 mg/L, sucrose 20 g/L; both Sigma) until 2 weeks after the end of chemotherapy. This antibiotic regimen has been shown to efficiently decontaminate aerobic Gram-negative pathogens without major effects on hematopoiesis). Mice are monitored by bioluminescent imaging every 4 d, starting 10 d after transplantation.

Chemotherapy is initiated upon detection of clear signals in pelvis, tail, and both femurs, and initial stage of hepatosplenic infiltration, which correlates with 30%-60% bone marrow infiltration as assessed by flow cytometry. Mice are treated for five consecutive days every 24 h with i.p. injections of test agents. Immediate response and long-term treatment effects are monitored by weekly luciferase imaging starting the first day after treatment and by histopathological analysis of representative mice at various time points. Cardiomyopathy, toxicity and efficacy are assessed in a dose-dependent manner to determine the performance of polypeptide-alpha-anti-CD138 as compared to doxorubicin alone.

Doxorubicin-polypeptide-anti-CD138 increases amount of doxorubicin incorporated by CD138-expressing cells, and decreases translocation of doxorubicin-polypeptide-anti-CD138 into non-CD138 expressing cells at doses of doxorubicin lower than doxorubicin alone.

Example 7: Producing a Nucleic Acid-Polypeptide with Solid Phase Synthesis

This example demonstrates solid phase synthesis of an exemplary polypeptide beta.

Therapeutic design: Polypeptide: PFDILYQ-CG-RGQGDC (SEQ ID NO: 3)

Experimental design: An exemplary polypeptide beta, as described herein, is synthesized automatically (MilliGen 9050 peptide synthesizer) by the solid-phase method using standard Fmoc (N-(9-fluorenyl)methoxycarbonyl) chemistry in a continuous flow mode.

Polypeptide purification is performed by reversed-phase high-performance liquid chromatography (RP-HPLC) with UV detection at 260 nm using a semi-prep column C18 (10 μm, 300×7.7 mm, Xterra Waters, 300 Å), eluting with water containing 0.1% TFA (eluent A) and acetonitrile containing 0.1% TFA (eluent B); elution gradient: from 100% A to 50% B in 30 min, flow: 4 ml/min. The purity and identity of the purified polypeptide are examined by ultra-performance liquid chromatography tandem mass-spectrometry (UPLC-MS; Waters Acquity equipped with ESI-Q analyzer) using an Acquity UPLC BEH C18; 2.1×50 MM, 1.7 μm column. Expected mass peaks are observed for amino acid and nucleic acid sequences corresponding to SEQ ID NO: 3.

Example 8: Click Chemistry to Link Polypeptide Beta and a Heterologous Moiety

This example demonstrates joining one or more exemplary polypeptide betas to one or more heterologous moieties through click chemistry.

Click chemistry involves rapid generation of compounds by joining small units together via heteroatom links (e.g. C-X-C). A main objective of click chemistry is to develop a set of powerful, selective, and modular blocks that are useful for small- and large-scale applications. Click reactions are bio-orthogonal, i.e. can occur within organisms without interfering with native biochemical processes. Reaction of a dibenzylcyclooctyne (DBCO) linker with an azide linker forms a stable triazole. This click reaction (between DBCO and azide) is very fast at room temperature, does not require a cytotoxic Cu(I) catalyst, and creates stable triazoles. This unique covalent bond is created when DBCO, incorporated into one type of biomolecule, reacts with an azide linker, incorporated into a second biomolecule. DBCO strain-promoted or Cu(I)-free [2+3] cycloaddition strategy relies on the use of strained dibenzylcyclooctynes. Use of strained dibenzylcyclooctynes decreases activation energy required for a cycloaddition click reaction, allowing it to be carried out without need for catalysis at low temperatures with an efficiency greater than that of a Cu(I)-catalyzed ligation.

Therapeutic design: Polypeptide beta with dibenzylcyclooctyne (DBCO) modification and penicillin with azide modification.

Experimental design: To prepare for a click reaction, polypeptide betas are labeled with DBCO (Glen Research, Sterling, VA). DBCO-sulfo-NHS ester is dissolved at a concentration of 5.2 mg per 60 μL in water or anhydrous DMSO. This stock solution is used to conjugate the amino-modified polypeptides in sodium carbonate/bicarbonate conjugation buffer, pH=~9.

For a 0.2 μmol synthesis of DBCO-conjugated polypeptide betas, polypeptide betas are dissolved in 500 μL of conjugation buffer. Approx. a 6 fold excess (6 μL) of DBCO-sulfo-NHS ester solution is added to the solution of dissolved polypeptide. The mixture is vortexed and incubated at room temperature for 2-4 hours up to about overnight. DBCO-conjugated polypeptide betas are desalted on a desalting column (Glen Research, Sterling, VA) to remove salts and organics.

Penicillin is dissolved in 500 μL of conjugation buffer. Approx. a 6 fold excess (6 μL) of azide solution is added to the solution of dissolved penicillin. The mixture is vortexed and incubated at room temperature for 2-4 hours up to about overnight. Azide-conjugated penicillin is desalted on a desalting column (Glen Research, Sterling, VA) to remove salts and organics.

Figure 4:
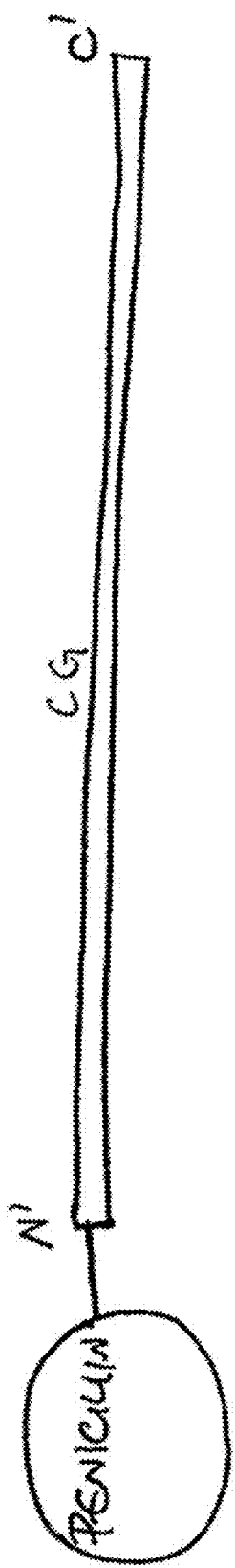
FIG. 4 is an illustration of a polypeptide beta linked to penicillin.

To perform a click reaction, 1 mg of azide is dissolved in 150 μL of DMSO. The azide solution is added to 10 OD of DBCO-conjugated polypeptide betas in 100 μL of water. The mixture is incubated at room temperature overnight. The ligated polypeptides (comprising DBCO-conjugated polypeptide betas ligated to azide-conjugated penicillin) are desalted on a desalting column (Glen Research, Sterling, VA) to remove salts and organics. See FIG. 4.

In another click reaction, succinimidyl esters, (5/6-carboxyfluorescein succinimidyl ester and succinimidyl-2-(biotinamido)ethyl-1,3-dithiopropionate, Thermo Fisher Scientific, Waltham, USA) are dissolved in dry DMSO (Acros, Geel, Belgium). Primary amine labeling is carried out at 4° C. for 1 hour in 20 mM Na Phosphate buffer pH 7.2 containing 0.05% dodecyl maltoside.

Maleimides, dibenzylcyclooctyne-PEG4-maleimide and azido-PEG3-maleimide (Jena Bioscience), are dissolved in dry DMSO. Sulfhydryl labeling is performed at 25° C. for 2 hours in 20 mM Na Phosphate buffer pH 7.2 containing 0.05% dodecyl maltoside. Copper-free coupling by click chemistry is performed in the same buffer for 10 hours at 4° C.

After a reaction with 5/6-carboxyfluorescein succinimidyl ester and maleimides, labeled protein is separated from unreacted label using spin columns (Micro Biospin TM6 columns, Bio-Rad, Hercules, USA), according to the manufacturer's instructions.

Reaction products after coupling are analyzed by HPLC. 20-40 μl samples are injected and separated on a chromatography system equipped with an analytical column (300 mm×4.60 mm) eluted with 20 mM Na Phosphate buffer pH 7.2 containing 0.05% dodecyl maltoside at a flow rate of 0.5 ml/min and followed by absorption at 280 nm. Absorption spectra of peaks are obtained from an integrated spectral detector (Agilent technologies G1315D diode array detector).

Example 9: Nuclear Suppression of Transcription by Physical Interference and Prevention of Interaction Between Target Promoters and Transcriptional Machinery This example demonstrates inhibition of gene expression with exemplary polypeptides that target a promoter region of a gene in a nucleus of a given cell.

ELANE-related neutropenia includes severe congenital neutropenia (SCN) and cyclic neutropenia, both of which are primary hematologic disorders characterized by recurrent fever, skin and oropharyngeal inflammation (e.g., mouth ulcers, gingivitis, sinusitis, and pharyngitis), and cervical adenopathy. Infectious complications are generally more severe in congenital neutropenia than in cyclic neutropenia and can lead to death if untreated. Most cases of SCN respond to treatment with granulocyte colony-stimulating factor, which increases neutrophil count and decreases severity and frequency of infections. However, after 15 years with granulocyte colony stimulating factor treatment, risk of developing myelodysplasia (MDS) or acute myelogenous leukemia AML is approximately 15%-25%.

Figure 5:
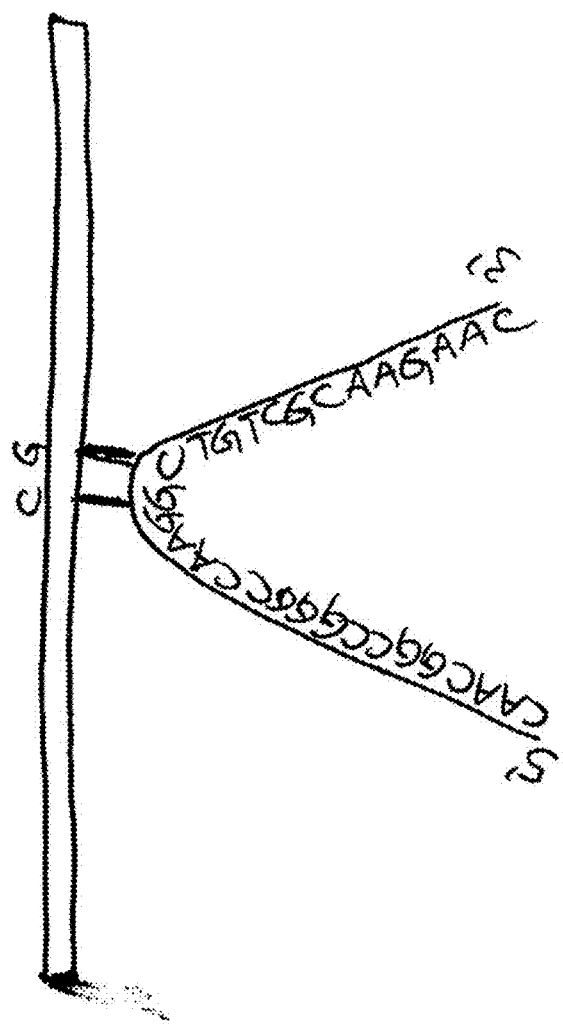
FIG. 5 is an illustration of a polypeptide beta hybridized to the promoter of the ELANE gene (SEQ ID NO: 4: CAACGGCCGGGCCAAGGCTGTCGCAAGAAC).

Mutations in the neutrophil elastase gene, ELANE, are the most common causes of severe congenital neutropenia as well as of cyclic neutropenia. ELANE maps to 19p13.31 of the human genome and mutations in the ELANE gene are identified in approximately 35-84% of individuals with SCN. SCN and cyclic neutropenia secondary to mutations in ELANE are inherited as autosomal dominant conditions. ELANE has five exons and encodes a 218 amino acid protein known as neutrophil elastase (NE). NE belongs to a class of serine proteases and is expressed exclusively in mature myelomonocytic cells and their committed immature precursors (promyelocytes and promonocytes). Stored as an active protease in azurophilic granules, NE is released upon exposure of neutrophils to inflammatory stimuli. In an extracellular environment, NE cleaves extracellular matrix proteins, while serine protease inhibitors antagonize proteinase activity Therapeutic design: In this example, an SCN phenotype may be reversed by reducing transcription of the ELANE gene in neutrophil precursors. In order to achieve reduction in expression of the ELANE gene and/or reversal of an SCN phenotype, a provided polypeptide as produced, e.g., in Example 7, is hybridized to an oligonucleotide with an exemplary nucleic acid sequence complimentary to the promoter of the ELANE gene (e.g. caacggccgggc-caaggctgtcgcaagaac; SEQ ID NO: 4) to produce a polypeptide-oligonucleotide complex; see FIG. 5, and delivered to myelomonocytes, promyelocytes, and promonocytes. A provided polypeptide-oligonucleotide complex passes through cell and nuclear membranes to hybridize to a target on the ELANE promoter (and e.g. may physically interfere with assembly of a transcription initiation complex), thereby reducing expression of ELANE.

Experimental design: This approach is tested in iPSCs-derived from SCN patients. To determine if gene correction of ELANE mutations restores granulopoietic differentiation, SCN iPSCs are exposed to polypeptides linked to either an oligonucleotide (polypeptide-oligonucleotide complex) that complements the ELANE ORF, or a scrambled sequence (as a control), and selected for incorporation of the polypeptide-oligonucleotide complex. iPSCs are differentiated into CD45+CD34+ hematopoietic progenitors by 10 days of culture in myeloid expansion medium (IMDM+Ham's F12 at 3:1 ratio) containing 0.5% N2 supplement, 1% B27 supplement without vitamin A, 0.5% human serum albumin, 100 µM monothioglycerol, 50 µg/ml ascorbic acid, 100 ng/ml recombinant SCF, 10 ng/ml IL-3, and 10 ng/ml GM-CSF. Cultures are further differentiated using granulopoietic culture conditions (IMDM+Ham's F12 at 3:1 ratio) containing 0.5% N2 supplement, 1% B27 supplement without vitamin A, 0.5% human serum albumin, 100 µM monothioglycerol, 50 µg/ml ascorbic acid, and 50 ng/ml G-CSF (Neupogen filgrastim) for 5 days. At the granulopoietic differentiation stage, cells are cultured at low (50 ng/ml) or high (1,000 ng/ml) G-CSF doses. During myeloid expansion and granulopoietic differentiation, cells are cultured in presence or absence of Sivelestat (Sigma-Aldrich) at a concentration of 230 nM (~5 times the IC50 for NE). At the end of granulopoietic differentiation, cells are cytospun onto a Superfrost Plus Microscope slide (Fisher Scientific). Cells are then Wright-Giemsa stained and scored to characterize myeloid cell phenotypes (promyelocytes, myelocytes, metamyelocytes, bands, neutrophils, and monocytes) using an upright microscope (Motic BA310). For sorting promyelocytes, cells at the end of myeloid expansion are stained for CD45-Pacific Blue, CD34-PECy7, CD33-APC, CD11b-APCCy7 (catalog 557754, clone ICRF44, BD Biosciences), and CD15-FITC (catalog 562370, clone W6D3, BD Biosciences). Promyelocytes/myelocyte populations (defined as CD45$^+$/CD34$^-$/CD33$^+$/CD11b$^-$/CD15$^{dim}$) are selected by FACS.

Expression of ELANE is quantitatively measured by PCR and determined to be greater in treated than in untreated cells.

Example 10: Producing a Nucleic Acid-Polypeptide with Solid Phase Synthesis

This example demonstrates solid phase synthesis of one or more exemplary polypeptides.

Therapeutic design: Polypeptide 1: PFDILYQ-TG-RGQGDC (SEQ ID NO: 5); polypeptide 2: PFDILYQ-TC-RGQGDC (SEQ ID NO: 6); polypeptide 3: PFDILYQ-CC-RGQGDC (SEQ ID NO: 7); polypeptide 4: PFDILYQ-GG-RGQGDC (SEQ ID NO: 8).

Experimental design: Certain exemplary polypeptides (each of which is an exemplary polypeptide beta), as shown herein, are synthesized automatically (MilliGen 9050 peptide synthesizer) by the solid-phase method using standard Fmoc (N-(9-fluorenyl)methoxycarbonyl) chemistry in a continuous flow mode. the two or more polypeptides (e.g., two or more instances of the same polypeptide or at least one instance of each of two of the polypeptides) are associated with one another, e.g., multimerized via ligation or click chemistry, to produce a gamma polypeptide. Optionally, one or more heterologous moieties (e.g., a therapeutic cargo such as, for example, one or more of penicillin, GlyH101, AQP2 ligand, doxorubicin, anti-CD138, etc., may be associated with such gamma polypeptides).

Polypeptide purification is performed by reversed-phase high-performance liquid chromatography (RP-HPLC) with UV detection at 260 nm using a semi-prep column C18 (10 µm, 300×7.7 mm, Xterra Waters, 300 Å), eluting with water containing 0.1% TFA (eluent A) and acetonitrile containing 0.1% TFA (eluent B); elution gradient: from 100% A to 50% B in 30 min, flow: 4 ml/min. The purity and identity of the purified PNA are examined by ultra-performance liquid chromatography tandem mass-spectrometry (UPLC-MS; Waters Acquity equipped with ESI-Q analyzer) using an Acquity UPLC BEH C18; 2.1×50 MM, 1.7 µm column. Expected mass peaks are observed for amino acid and nucleic acid sequences corresponding to SEQ ID NO: 5-SEQ ID NO: 8.

Example 11: Nuclear Suppression of Transcription by Physical Interference and Prevention of Interactions Between Target Promoters and Transcriptional Machinery This example demonstrates inhibition of gene expression with exemplary polypeptide gammas that target a promoter region of a gene in a nucleus of a given cell.

ELANE-related neutropenia includes severe congenital neutropenia (SCN) and cyclic neutropenia, both of which are primary hematologic disorders characterized by recurrent fever, skin and oropharyngeal inflammation (e.g., mouth ulcers, gingivitis, sinusitis, and pharyngitis), and cervical adenopathy. Infectious complications are generally more severe in congenital neutropenia than in cyclic neutropenia and can lead to death if untreated. Most cases of SCN respond to treatment with granulocyte colony-stimulating factor, which increases neutrophil count and decreases severity and frequency of infections. However, after 15 years with granulocyte colony stimulating factor treatment, risk of developing myelodysplasia (MDS) or acute myelogenous leukemia AML is approximately 15%-25%.

Figure 6:
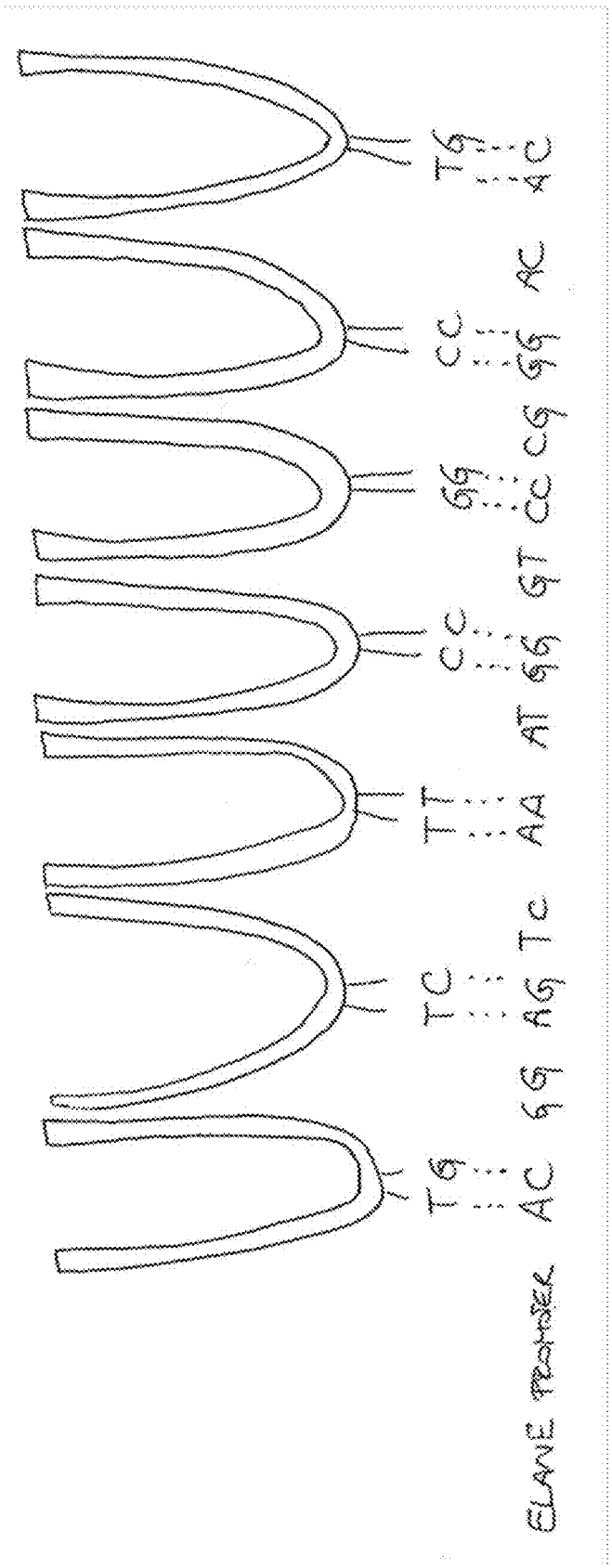
FIG. 6 is an illustration of a polypeptide gamma hybridized to the promoter of the ELANE gene (SEQ ID NO: 34: ACGGAGTCAAATGGGTCCCGGGACAC).
Figure 7:
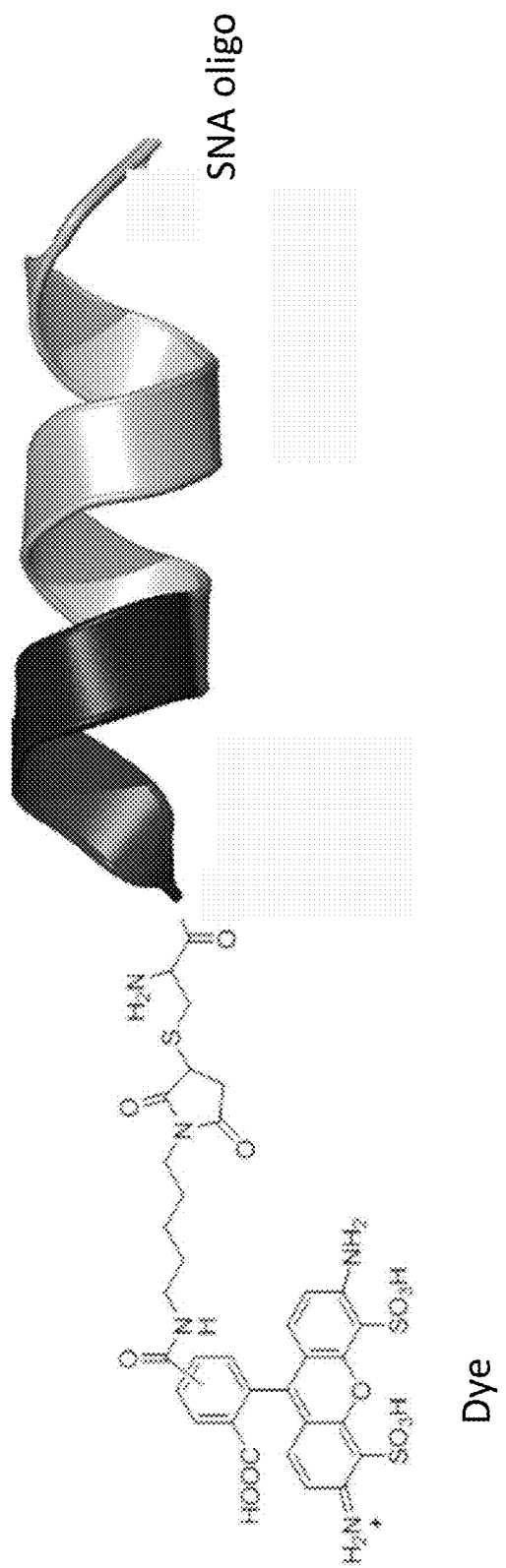
FIG. 7 is an illustration of an exemplary view of a three dimensional structure of a polypeptide of SEQ ID NO: 9.
Figure 8:
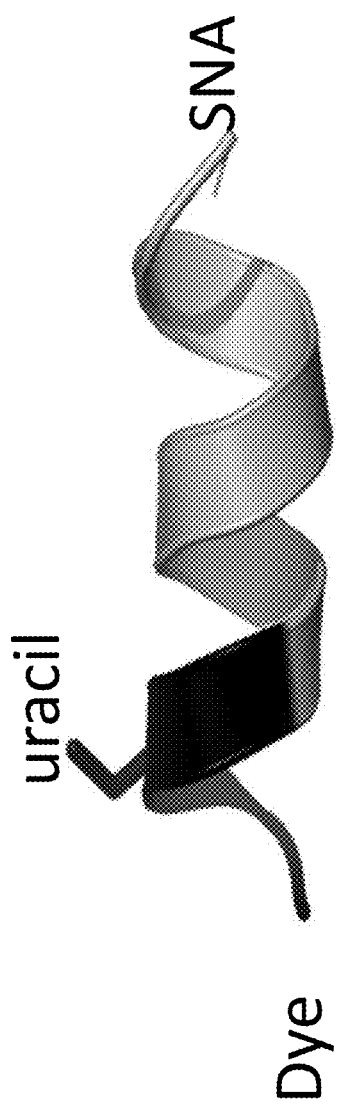
FIG. 8 is an illustration of an exemplary view of a three dimensional structure of a polypeptide of SEQ ID NO: 11.
Figure 9:
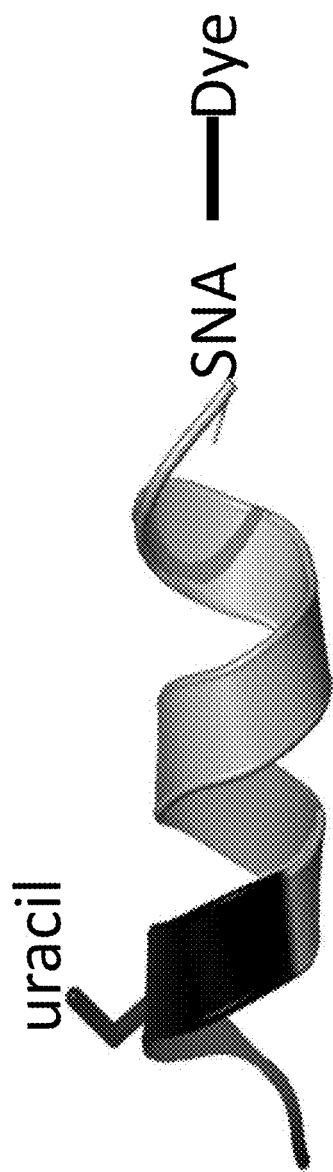
FIG. 9 is an illustration of an exemplary view of a three dimensional structure of a polypeptide of SEQ ID NO: 12.
Figure 10:
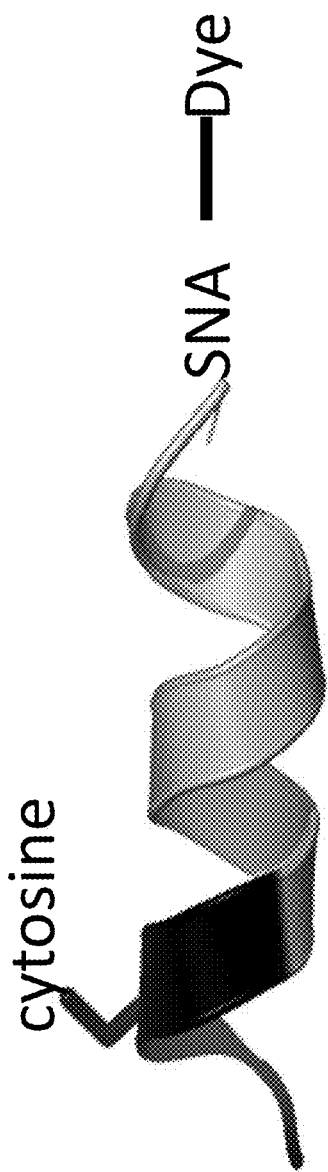
FIG. 10 is an illustration of an exemplary view of a three dimensional structure of a polypeptide of SEQ ID NO: 13.
Figure 11:
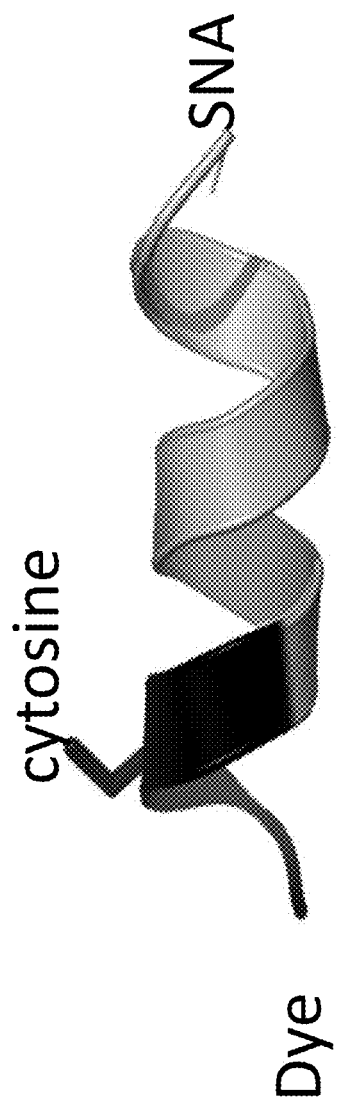
FIG. 11 is an illustration of an exemplary view of a three dimensional structure of a polypeptide of SEQ ID NO: 14.
Figure 12:
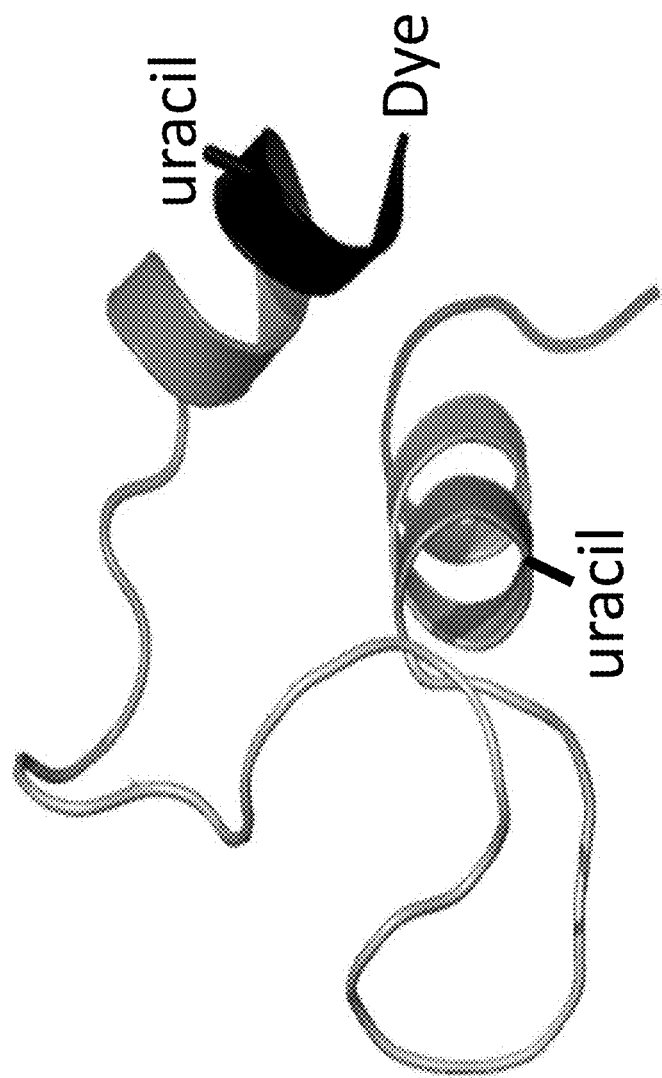
FIG. 12 is an illustration of an exemplary view of a three dimensional structure of a polypeptide of SEQ ID NO: 15.
Figure 13:
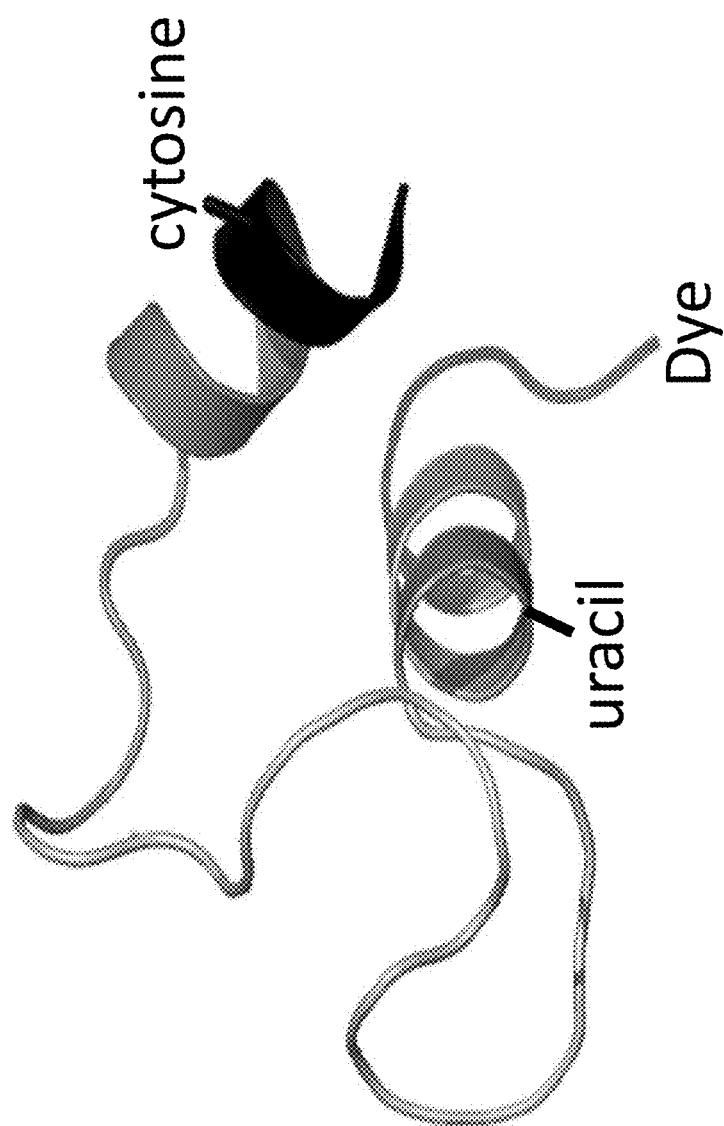
FIG. 13 is an illustration of an exemplary view of a three dimensional structure of a polypeptide of SEQ ID NO: 16.
Figure 14:
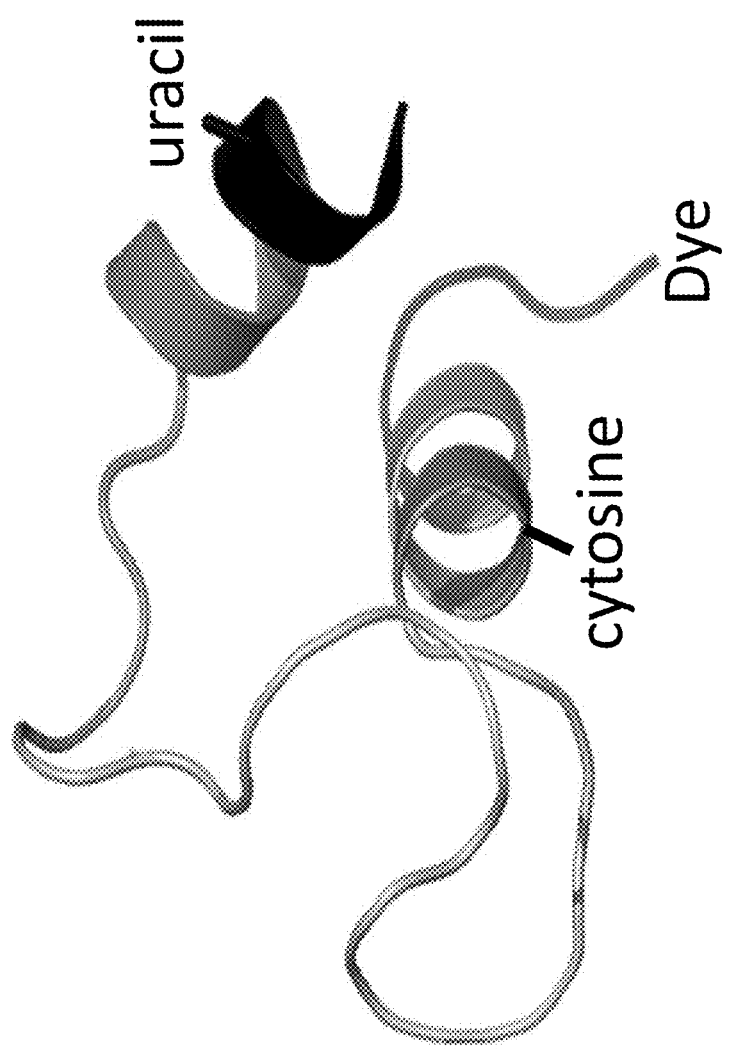
FIG. 14 is an illustration of an exemplary view of a three dimensional structure of a polypeptide of SEQ ID NO: 17.
Figure 15:
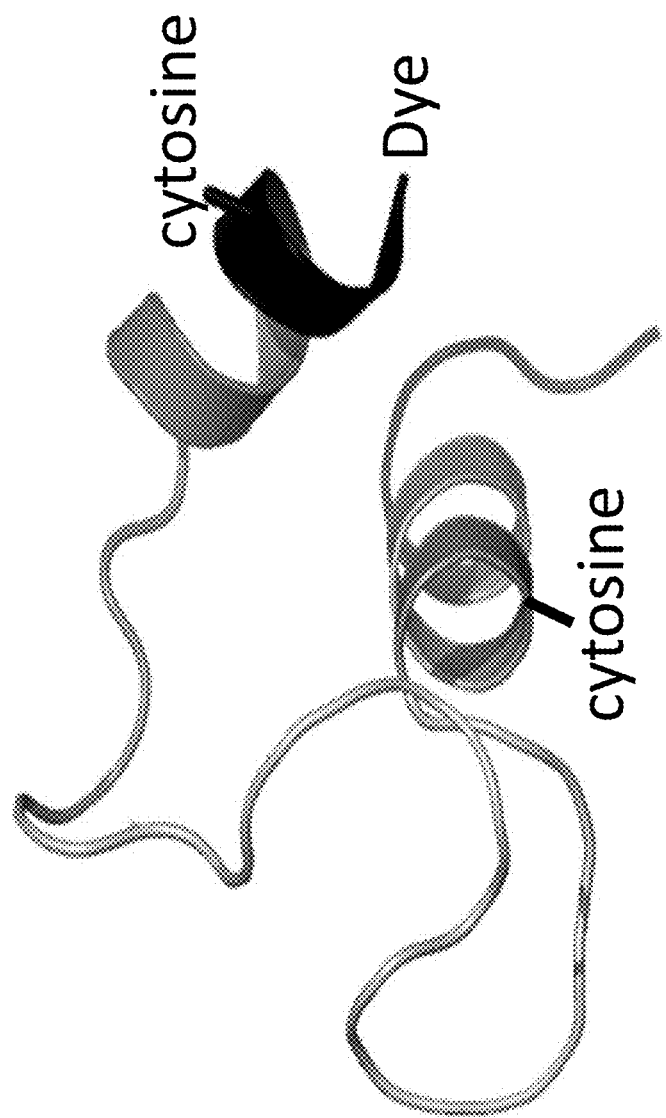
FIG. 15 depicts an exemplary view of a three dimensional structure of a polypeptide of SEQ ID NO: 18.

Mutations in the neutrophil elastase gene, ELANE, are the most common causes of severe congenital neutropenia as well as of cyclic neutropenia. ELANE maps to 19p13.31 of the human genome and mutations in the ELANE gene are identified in approximately 35-84% of individuals with SCN. SCN and cyclic neutropenia secondary to mutations in ELANE are inherited as autosomal dominant conditions. ELANE has five exons and encodes a 218 amino acid protein known as neutrophil elastase (NE). NE belongs to a class of serine proteases and is expressed exclusively in mature myelomonocytic cells and their committed immature precursors (promyelocytes and promonocytes). Stored as an active protease in azurophilic granules, NE is released upon exposure of neutrophils to inflammatory stimuli. In the extracellular environment, NE cleaves extracellular matrix proteins, while serine protease inhibitors antagonize proteinase activity Therapeutic design: In this example, an SCN phenotype may be reversed by reducing transcription of the ELANE gene in neutrophil precursors. In order to achieve reduction in expression of the ELANE gene and/or reversal of an SCN phenotype, a provided polypeptide gamma as produced, e.g., in Examples 13-15, is hybridized to an oligonucleotide with an exemplary nucleic acid sequence complimentary to the promoter of the ELANE gene (e.g. caacggccgggccaaggctgtcgcaagaac, SEQ ID NO: 4) to produce a polypeptide-oligonucleotide complex; see FIG. 6, and delivered to myelomonocytes, promyelocytes and promonocytes. A provided polypeptide-oligonucleotide complex passes through cell and nuclear membranes to hybridize to a target on the ELANE promoter (and e.g. may physically interfere with assembly of a transcription initiation complex), thereby reducing expression of ELANE.

Experimental design: This approach is tested in iPSCs derived from SCN patients. To determine if gene correction of ELANE mutations restores granulopoietic differentiation, SCN iPSCs are exposed to polypeptides linked to either an oligonucleotide (polypeptide-oligonucleotide complex) that complements the ELANE ORF, or a scrambled sequence (as a control), and selected for incorporation of the polypeptide-oligonucleotide complex. iPSCs are differentiated into CD45$^+$CD34$^+$ hematopoietic progenitors by 10 days of culture in myeloid expansion medium (IMDM+Ham's F12 at 3:1 ratio) containing 0.5% N2 supplement, 1% B27 supplement without vitamin A, 0.5% human serum albumin, 100 μM monothioglycerol, 50 μg/ml ascorbic acid, 100 ng/ml recombinant SCF, 10 ng/ml IL-3, and 10 ng/ml GM-CSF. Cultures are further differentiated using granulopoietic culture conditions (IMDM+Ham's F12 at 3:1 ratio) containing 0.5% N2 supplement, 1% B27 supplement without vitamin A, 0.5% human serum albumin, 100 μM monothioglycerol, 50 μg/ml ascorbic acid, and 50 ng/ml G-CSF (Neupogen filgrastim) for 5 days. At the granulopoietic differentiation stage, cells are cultured at low (50 ng/ml) or high (1,000 ng/ml) G-CSF doses. During myeloid expansion and granulopoietic differentiation, cells are cultured in presence or absence of Sivelestat (Sigma-Aldrich) at a concentration of 230 nM (~5 times the IC50 for NE). At the end of granulopoietic differentiation, cells are cytospun onto a Superfrost Plus Microscope slide (Fisher Scientific). Cells are then Wright-Giemsa stained and scored to characterize myeloid cell phenotypes (promyelocytes, myelocytes, metamyelocytes, bands, neutrophils, and monocytes) using an upright microscope (Motic BA310). For sorting promyelocytes, cells at the end of myeloid expansion are stained for CD45-Pacific Blue, CD34-PECy7, CD33-APC, CD11b-APCCy7 (catalog 557754, clone ICRF44, BD Biosciences), and CD15-FITC (catalog 562370, clone W6D3, BD Biosciences). Promyelocytes/myelocyte populations (defined as CD45$^+$/CD34$^-$/CD33$^+$/CD11b$^-$/CD15$^{dim}$) are selected by FACS.

Expression of ELANE is quantitatively measured by PCR and determined to be greater in treated than in untreated cells.

Example 12: Exemplary Alpha, Beta, and Gamma Peptides

This example demonstrates exemplary polypeptides as described herein, each linked to a heterologous moiety, e.g., a synthetic nucleic acid.

All peptides and synthetic nucleic acids ("SNA"s) have been chemically synthesized from commercially available vendors. All agents were reconstituted in sterile dimethylsulfoxide (DMSO) solution. All sequences are provided herein.

TABLE 1

Sequences of exemplary polypeptides linked to SNAs, optionally, with or without a linked fluorescent dye.

| Exemplary Polypeptide | (Optional Fluorescent dye)-Polypeptide-SNA Sequence (5'-3') (* = phosphorothioate linkage) | ABX"C (N and C terminus orientation) |
|---|---|---|
| Alpha1-SNA (SEQ ID NO: 9) | (Fluorescent dye)-PLIYLRLLRGQF (SEQ ID NO: 9)- *G*G*A*A*AAAGCGGTCAACTTTCACGTGGGCAAGTTGTTTTACGGC CACAAGGTGGC*G*C*A*G*A*A (SEQ ID NO: 10) | LRLLR (SEQ ID NO: 33) (N to C) |
| Alpha2-SNA (SEQ ID NO: 10) | FQGRLLRLYILP (SEQ ID NO: 19)- A*A*G*T*A*AGTGTGCCCTCTACTGGCAGCAGAG*A*T*C*A*T (SEQ ID NO: 10) | RLLRL (SEQ ID NO: 33) (C to N) |
| Beta1-SNA (SEQ ID NO: 11) | (Fluorescent dye)-FQ-(uracil)-RLLRNYILP (SEQ ID NO: 11)- *G*G*A*A*AAAGCGGTCAACTTTCACGTGGGCAAGTTGTTTTACGGC CACAAGGTGGC*G*C*A*G*A*A (SEQ ID NO: 10) | FQ-(uracil)-R (N to C) |
| Beta2-SNA (SEQ ID NO: 12) | IR-(uracil)-QLLRQFSIP (SEQ ID NO: 13)- *G*G*A*A*AAAGCGGTCAACTTTCACGTGGGCAAGTTGTTTTACGGC CACAAGGTGGC*G*C*A*G*A*A (SEQ ID NO: 10)- (Fluorescent dye) | IR-(uracil)-Q (N to C) |
| Beta3-SNA (SEQ ID NO: 13) | YK-(cytosine)-KWWRNYGLP (SEQ ID NO: 15)- *G*G*A*A*AAAGCGGTCAACTTTCACGTGGGCAAGTTGTTTTACGGC CACAAGGTGGC*G*C*A*G*A*A (SEQ ID NO: 10)- (Fluorescent dye) | YK-(cytosine)-K (N to C) |

TABLE 1-continued

Sequences of exemplary polypeptides linked to SNAs, optionally, with or without a linked fluorescent dye.

| Exemplary Polypeptide | (Optional Fluorescent dye)-Polypeptide-SNA Sequence (5'-3') (* = phosphorothioate linkage) | ABX"C (N and C terminus orientation) |
|---|---|---|
| Beta4-SNA (SEQ ID NO: 14) | (Fluorescent dye)-FN-(cytosine)-NWWRQFSIP- (SEQ ID NO: 17) *G*G*A*A*AAAGCGGTCAACTTTCACGTGGGCAAGTTGTTTTACGGC CACAAGGTGGC*G*C*A*G*A*A (SEQ ID NO: 10) | FN-(cytosine)-N (N to C) |
| Gamma1-SNA (SEQ ID NO: 15) | (Fluorescenta dye)-FQ-(uracil)-RLLRNYILP- (SEQ ID NO: 11) *G*G*A*A*AAAGCGGTCAACTTTCACGTGGGCAAGTTGTTTTACGGC CACAAGGTGGC*G*C*A*G*A*A-IK-(uracil)-NLLRQYILP (SEQ ID NO: 10) | FQ-(uracil-R (N to C) IK-(uracil)-N (N to C) |
| Gamma2-SNA (SEQ ID NO: 16) | IR-(cytosine)-QLLRQFSIP (SEQ ID NO: 24)- *G*G*A*A*AAAGCGGTCAACTTTCACGTGGGCAAGTTGTTTTACGGC CACAAGGTGGC*G*C*A*G*A*A (SEQ ID NO: 10)-YQ- (uracil)-K-LLRNFSIP (SEQ ID NO: 26) (Fluorescent dye) | IR-(cytosine)-Q (N to C) YQ-(uracil)-K (N to C) |
| Gamma3-SNA (SEQ ID NO: 17) | YK-(uracil)-KWWRNYGLP (SEQ ID NO: 27)- *G*G*A*A*AAAGCGGTCAACTTTCACGTGGGCAAGTTGTTTTACGGC CACAAGGTGGC*C*G*C*A*G*A*A (SEQ ID NO: 10)-FN- (cytosine)-Q-WWRQYGLP (SEQ ID NO: 29) (Fluorescent dye) | YK-(uracil)-K (N to C) FN-(cytosine)-Q (N to C) |
| Gamma4-SNA (SEQ ID NO: 18) | (Fluorescent dye)-FN-(cytosine)-NWWRQFSIP (SEQ ID NO: 30)- *G*G*A*A*AAAGCGGTCAACTTTCACGTGGGCAAGTTGTTTTACGGC CACAAGGTGGC*G*C*A*G*A*A (SEQ ID NO: 10)-IQ- (cytosine)-RWWRNFSIP (SEQ ID NO: 32) | FN-(cytosine)-N (N to C) IQ-(cytosine)-R (N to C) |

Certain three dimensional structures of exemplary peptides of Table 1 are modeled in FIGS. 7-15.

Example 13: Translocation of Exemplary Beta and/or Gamma Polypeptides

In this example, exemplary beta and/or gamma polypeptides as provided herein may be labeled with one or more heterologous moiety(ies).

Provided polypeptides are labeled with an N-terminal heterologous moiety (e.g. fluorescent dye (AlexaFluor)). Fluorescent dyes (including Alexa Fluor) are typically membrane impermeant in live cells (as opposed to, e.g. fixed cells used for immunocytochemistry). However, the present disclosure encompasses a recognition that, when linked to a provided polypeptide, a dye (e.g. heterologous moiety) may cross a cellular membrane (e.g. plasma membrane, nuclear membrane, etc.). Furthermore, use of a bright, easily visualizable fluorophore e.g. dye), can facilitate tracking translocation across cellular membranes, e.g., by imaging with fluorescence microscopy.

Chinese hamster ovary (CHO) cells are seeded on coverglass slides with 4 chambers. Typical seeding densities of CHO cells range from $1 \times 10^4$ to $1 \times 10^5$ cells per chamber with a 1.7 cm² seeding area. Cells are grown in 500 µl complete media at 37° C. with 5% $CO_2$ for 24-48 hours prior to experimentation.

To perform translocation experiments, slides with adherent cells are removed from an incubator. Cells are then washed with 37° C. PBS, then with room temperature (22° C.) PBS and allowed to incubate at room temperature for 30 minutes after washing. Next, fluorescein dextran 3000 Da (FD3) is added as an aqueous phase marker to a final concentration of 10 µg/ml. Dye-labeled peptides are added from stock dimethylsulfoxide (DMSO)-containing peptide solutions. to a final peptide concentration of 2 µM. Final DMSO concentration in the cell culture is 1% or less, which does not affect cells.

Cells are imaged using a 488 nm laser and 520 nm bandpass filter for FD3 and a 543 nm laser with a 580 nm bandpass filter for fluorescence. Under these conditions, bleed-through between channels is negligible. Focal plane is always adjusted to give the maximum cell diameter in the FD3 detection mode, thus avoiding focal planes too near the top or the bottom of the cell.

Peptide translocation across a cell membrane is assessed using laser scanning confocal fluorescence microscopy. Soluble, polar probes such as free dye and fluorescein dextran 3,000 Da (FD3) are excluded.

Peptides and their attached fluorescent dyes are expected to equilibrate across a bilayer membrane indicating translocation.

Example 14: Alpha Polypeptides do not Affect Function of SNAs

HEK293T cells were treated with an exemplary polypeptide alpha (FQGRLLRLYILP; SEQ ID NO: 19) linked to an exemplary SNA (e.g. 5'-AAGTAAGTGTGCCCTC-TACTGGCAGCAGAGATCAT-3'; SEQ ID NO: 20 resulting in a polypeptide-SNA of, e.g. SEQ ID NO: 10) engineered to bind to sequences flanking a MYC gene sequence (with or without fluorescent dye). Additional exemplary polypeptides are listed in Table 1. At 72 hours post-treatment, cells were harvested for RNA extraction and cDNA was synthesized (Thermo Fisher Scientific) according to manufacturer's protocols. cDNA was used as a template for quantitative real-time PCR.

MYC-specific quantitative PCR probes/primers were multiplexed with internal control quantitative PCR probes/primers and gene expression was subsequently analyzed by a real time PCR kit (Applied Biosystems, Thermo Fisher Scientific).

Cells treated with SNAs that are complementary to sequences proximal to the MYC gene showed reduction in MYC expression indicating translocation of a provided polypeptide and linked SNA.

Preliminary studies with an exemplary polypeptide alpha conjugated to SNAs indicate no adverse effects of peptides on ability of SNAs to reduce MYC expression levels.

Example 15: Beta and Gamma Peptides do not Affect Function of SNAs

HEK293T cells are treated with exemplary polypeptide betas and/or gammas linked to SNAs (exemplary peptides are listed in Table 1) engineered to bind to sequences flanking a MYC gene (with or without fluorescent dye). At 72 hours post-treatment, cells are harvested for RNA extraction and cDNA is synthesized (Thermo Fisher Scientific) according to manufacturer's protocols. cDNA is used as a template for quantitative real-time PCR.

MYC-specific quantitative PCR probes/primers are multiplexed with internal control quantitative PCR probes/primers and gene expression is subsequently analyzed by a real time PCR kit (Applied Biosystems, Thermo Fisher Scientific).

Cells treated with SNAs proximal to the MYC gene are expected to show reduction in MYC expression indicating translocation of the peptide and linked SNA.

Results of studies using exemplary polypeptide betas or gammas conjugated to SNAs will indicate no adverse effects of provided polypeptides on ability of SNAs to reduce MYC expression levels.

EQUIVALENTS

It is to be understood that while the present disclosure has been described in conjunction with the detailed description thereof, the foregoing description is intended to illustrate and not limit the scope of the present disclosure, which is defined by the scope of the appended claims. Other aspects, advantages, and modifications are within the scope of the following claims.

---

What is claimed is:

1. A method of delivering a therapeutic comprising: administering a composition to a subject, the composition comprising: a polypeptide comprising at least one sequence of ABX"C, wherein A is selected from a hydrophobic amino acid or an amide containing backbone, with a nucleic acid side chain; B and C may be the same or different, and are independently selected from arginine, asparagine, glutamine, lysine, and analogs thereof; X is an amide containing backbone, with a nucleic acid side chain; and n is an integer from 1 to 4; and at least one heterologous moiety, wherein the heterologous moiety is the therapeutic, and wherein the composition increases intracellular delivery of the therapeutic as compared to the therapeutic alone.

2. The method of claim 1, wherein:
the composition is targeted to a specific cell, or a specific tissue; or
(ii) the amide containing backbone is aminoethyl-glycine.

3. The method of claim 1, wherein the composition crosses a blood-brain-barrier, a placental membrane, or a blood-testis barrier.

4. The method of claim 1, wherein the composition is administered systemically.

5. The method of claim 1, wherein the composition has differential pharmacokinetics or pharmacodynamics (PK/PD) as compared to the therapeutic alone.

6. The method of claim 1, wherein the composition has reduced toxicokinetics as compared to the therapeutic alone.

7. The method of claim 1, wherein the administration is non-parenteral and the therapeutic is a parenteral therapeutic.

8. The method of claim 1, wherein the composition increases efficacy and/or decreases toxicity of the therapeutic as compared to the therapeutic alone.

9. The method of claim 1, wherein the hydrophobic amino acid is selected from alanine, valine, isoleucine, leucine, methionine, phenylalanine, tyrosine, tryptophan, and analogs thereof.

10. The method of claim 1, wherein B is selected from arginine or glutamine.

11. The method of claim 1, wherein C is arginine.

12. The method of claim 1, wherein n is 2.

13. The method of claim 1, wherein the heterologous moiety is selected from the group consisting of a small molecule, a peptide, a peptide nucleic acid (PNA), siRNA, DNA, modified RNA, and RNA.

14. The method of claim 1, wherein the heterologous moiety possesses at least one effector activity selected from the group consisting of modulates a biological activity, binds a regulatory protein, modulates enzymatic activity, modulates substrate binding, modulates receptor activation, modulates protein stability/degradation, and modulates transcript stability/degradation.

15. The method of claim 1, wherein the heterologous moiety:
i) possesses at least one targeted function selected from the group consisting of modulates a function, modulates a molecule, and is localized to a specific location;
ii) is or comprises a tag or label;
iii) is selected from the group consisting of an epigenetic modifying agent, epigenetic enzyme, a bicyclic peptide, a transcription factor, a DNA or protein modification enzyme, a DNA-intercalating agent, an efflux pump inhibitor, a nuclear receptor activator or inhibitor, a proteasome inhibitor, a competitive inhibitor for an enzyme, a protein synthesis inhibitor, a nuclease, a protein fragment or domain, a tag or marker, an antigen, an antibody or antibody fragment, a ligand or a receptor, a synthetic or analog peptide from a naturally-bioactive peptide, an anti-microbial peptide, a pore-forming peptide, a targeting or cytotoxic peptide, a degradation or self-destruction peptide, a CRISPR component system or component thereof, DNA, RNA, artificial nucleic acids, a nanoparticle, an oligonucleotide aptamer, a peptide aptamer, and an agent with poor pharmacokinetics or pharmacodynamics (PK/PD); or
iv) is linked, via a linker or directly, to the polypeptide on an N terminus, a C terminus, both termini, or one or more amino acids of the polypeptide.

16. The method of claim 1, wherein the polypeptide comprises at least two ABX"C sequences.

17. The method of claim 1, wherein the polypeptide has a size in the range of about 5 to about 50 amino acid units in length.

18. The method of claim 1, wherein the nucleic acid side chain is independently selected from the group consisting of a purine side chain, a pyrimidine side chain, and a nucleic acid analog side chain.

19. The method of claim 1, wherein the nucleic acid side chain hybridizes to the heterologous moiety, wherein the heterologous moiety comprises a nucleic acid side chain.

* * * * *

UNITED STATES PATENT AND TRADEMARK OFFICE
CERTIFICATE OF CORRECTION

PATENT NO. : 11,951,154 B2
APPLICATION NO. : 17/835659
DATED : April 9, 2024
INVENTOR(S) : Laura Gabriela Lande et al.

It is certified that error appears in the above-identified patent and that said Letters Patent is hereby corrected as shown below:

In the Claims

At Column 77, Claim number 1, Line number 65, delete "$ABX''C$," and insert -- $ABX^nC$, --.

At Column 77, Claim number 1, Line number 66, delete "backbone," and insert -- backbone --.

At Column 78, Claim number 1, Line number 63, delete "backbone," and insert -- backbone --.

At Column 78, Claim number 1, Line number 64, delete "moiety," and insert -- moiety --.

At Column 79, Claim number 2, Line number 2, delete "the composition" and insert -- (i) the composition --.

At Column 80, Claim number 16, Line number 28, delete "$ABX''C$" and insert -- $ABX^nC$ --.

Signed and Sealed this
Twenty-fifth Day of June, 2024

Katherine Kelly Vidal
*Director of the United States Patent and Trademark Office*

SEQUENCE LISTING

```
<160> NUMBER OF SEQ ID NOS: 34

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Phe Asp Ile Leu Tyr Gln Leu Leu Arg Gly Gln Gly Asp Cys
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Lys Arg Val Thr Gly Arg Pro Cys
1               5

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Phe Asp Ile Leu Tyr Gln Cys Gly Arg Gly Gln Gly Asp Cys
1               5                   10                  15

<210> SEQ ID NO 4
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 4
caacggccgg gccaaggctg tcgcaagaac                                        30

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Phe Asp Ile Leu Tyr Gln Thr Gly Arg Gly Gln Gly Asp Cys
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Phe Asp Ile Leu Tyr Gln Thr Cys Arg Gly Gln Gly Asp Cys
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Phe Asp Ile Leu Tyr Gln Cys Cys Arg Gly Gln Gly Asp Cys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Phe Asp Ile Leu Tyr Gln Gly Gly Arg Gly Gln Gly Asp Cys
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Pro Leu Ile Tyr Leu Arg Leu Leu Arg Gly Gln Phe
1               5                   10
```

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ggaaaaagcg gtcaactttc acgtgggcaa gttgttttac ggccacaagg tggcgcagaa    60

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Uracil side chain

<400> SEQUENCE: 11

Phe Gln Arg Leu Leu Arg Asn Tyr Ile Leu Pro
1               5                   10

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggaaaaagcg gtcaactttc acgtgggcaa gttgttttac ggccacaagg tggcgcagaa    60

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Uracil side chain

<400> SEQUENCE: 13

Ile Arg Gln Leu Leu Arg Gln Phe Ser Ile Pro
1               5                   10

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggaaaaagcg gtcaactttc acgtgggcaa gttgttttac ggccacaagg tggcgcagaa    60

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cytosine side chain

<400> SEQUENCE: 15

Tyr Lys Lys Trp Trp Arg Asn Tyr Gly Leu Pro
1               5                   10

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggaaaaagcg gtcaactttc acgtgggcaa gttgttttac ggccacaagg tggcgcagaa    60

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cytosine side chain

<400> SEQUENCE: 17

Phe Asn Asn Trp Trp Arg Gln Phe Ser Ile Pro
1               5                   10

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggaaaaagcg gtcaactttc acgtgggcaa gttgttttac ggccacaagg tggcgcagaa    60

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Gln Gly Arg Leu Leu Arg Leu Tyr Ile Leu Pro
1               5                   10

<210> SEQ ID NO 20
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
aagtaagtgt gccctctact ggcagcagag atcat    35

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Uracil side chain

<400> SEQUENCE: 21

Phe Gln Arg Leu Leu Arg Asn Tyr Ile Leu Pro
1               5                   10

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggaaaaagcg gtcaactttc acgtgggcaa gttgttttac ggccacaagg tggcgcagaa    60

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Uracil side chain

<400> SEQUENCE: 23

Ile Lys Asn Leu Leu Arg Gln Tyr Ile Leu Pro
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cytosine side chain

<400> SEQUENCE: 24

Ile Arg Gln Leu Leu Arg Gln Phe Ser Ile Pro
1               5                   10

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 25
ggaaaaagcg gtcaactttc acgtgggcaa gttgttttac ggccacaagg tggcgcagaa    60

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Uracil side chain

<400> SEQUENCE: 26

Tyr Gln Lys Leu Leu Arg Asn Phe Ser Ile Pro
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Uracil side chain

<400> SEQUENCE: 27

Tyr Lys Lys Trp Trp Arg Asn Tyr Gly Leu Pro
1               5                   10

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggaaaaagcg gtcaactttc acgtgggcaa gttgttttac ggccacaagg tggcgcagaa    60

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cytosine side chain

<400> SEQUENCE: 29

Phe Asn Gln Trp Trp Arg Gln Tyr Gly Leu Pro
1               5                   10

<210> SEQ ID NO 30
<211> LENGTH: 11
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cytosine side chain

<400> SEQUENCE: 30

Phe Asn Asn Trp Trp Arg Gln Phe Ser Ile Pro
1               5                   10

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggaaaaagcg tcaactttc acgtgggcaa gttgttttac ggccacaagg tggcgcagaa    60

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cytosine side chain

<400> SEQUENCE: 32

Ile Gln Arg Trp Trp Arg Asn Phe Ser Ile Pro
1               5                   10

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Arg Leu Leu Arg
1               5

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
acggagtcaa atgggtcccg ggacac                                        26
```